US008350041B2

(12) United States Patent  
Carson et al.

(10) Patent No.: US 8,350,041 B2  
(45) Date of Patent: Jan. 8, 2013

(54) TRICYCLIC δ-OPIOID MODULATORS

(75) Inventors: John R. Carson, Norristown, PA (US);
Ellen Codd, Blue Bell, PA (US);
Christine M. Razler, Yardley, PA (US);
Andrea Works, Morgantown, WV (US);
Mark McDonnell, Lansdale, PA (US);
James J. McNally, Souderton, PA (US)

(73) Assignee: Janssen Pharmaceutica, NV (BE)

( * ) Notice: Subject to any disclaimer, the term of this patent is extended or adjusted under 35 U.S.C. 154(b) by 0 days.

(21) Appl. No.: 13/334,374

(22) Filed: Dec. 22, 2011

(65) Prior Publication Data

US 2012/0095010 A1 Apr. 19, 2012

Related U.S. Application Data

(62) Division of application No. 13/157,846, filed on Jun. 10, 2011, now Pat. No. 8,106,207, which is a division of application No. 12/536,635, filed on Aug. 6, 2009, now Pat. No. 7,982,042, which is a division of application No. 10/873,527, filed on Jun. 22, 2004, now Pat. No. 7,589,103.

(60) Provisional application No. 60/483,389, filed on Jun. 27, 2003.

(51) Int. Cl.
*A61K 31/4535* (2006.01)
*C07D 409/04* (2006.01)
(52) U.S. Cl. ........................... 546/202; 514/324
(58) Field of Classification Search ............... 546/202; 514/324
See application file for complete search history.

(56) References Cited

U.S. PATENT DOCUMENTS

| 2,368,006 | A | 1/1945 | Cusic |
| 2,784,185 | A | 3/1957 | Schuler |
| 2,901,478 | A | 8/1959 | Schuler |
| 3,179,665 | A | 4/1965 | Schmutz |
| 3,305,547 | A | 2/1967 | Stach et al. |
| 3,470,188 | A | 9/1969 | Kaiser et al. |
| 3,557,287 | A | 1/1971 | Berde et al. |
| 3,931,232 | A | 1/1976 | Bender et al. |
| 3,987,042 | A | 10/1976 | Gueremy et al. |
| 4,086,350 | A | 4/1978 | Zirkle |
| 4,275,209 | A | 6/1981 | Lassen et al. |
| 4,356,184 | A | 10/1982 | Deason et al. |
| 4,666,907 | A | 5/1987 | Fortin et al. |
| 4,777,177 | A | 10/1988 | Traber et al. |
| 5,502,049 | A | 3/1996 | Garret et al. |
| 6,004,983 | A | 12/1999 | Andersen et al. |
| 6,114,354 | A | 9/2000 | Andersen et al. |
| 6,153,626 | A | 11/2000 | Pelcman et al. |
| 7,060,711 | B2 | 6/2006 | Lubbert et al. |
| 7,432,257 | B2 | 10/2008 | Coats et al. |
| 7,439,239 | B2 | 10/2008 | Coats et al. |
| 7,553,850 | B2 | 6/2009 | Dax et al. |
| 2003/0018447 | A1 | 1/2003 | Florschuetz |
| 2003/0166672 | A1 | 9/2003 | Lubbert et al. |
| 2005/0009860 | A1 | 1/2005 | Carson et al. |
| 2006/0030585 | A1 | 2/2006 | Dax et al. |
| 2006/0135522 | A1 | 6/2006 | Carson et al. |
| 2006/0135524 | A1 | 6/2006 | Carson et al. |
| 2006/0135763 | A1 | 6/2006 | Coats et al. |
| 2006/0148823 | A1 | 7/2006 | Coats et al. |
| 2006/0287297 | A1 | 12/2006 | DeCorte et al. |
| 2008/0318937 | A1 | 12/2008 | Coats et al. |
| 2009/0042871 | A1 | 2/2009 | Coats et al. |

FOREIGN PATENT DOCUMENTS

| DE | 2009555 | 10/1970 |
| EP | 5607 B1 | 11/1979 |
| EP | 1049676 B1 | 11/2000 |
| EP | 1306376 A1 | 5/2003 |
| EP | 1321169 A1 | 6/2003 |
| FR | 2290202 A1 | 6/1976 |
| GB | 1128734 | 7/1966 |
| WO | WO 9828275 A1 | 7/1998 |
| WO | WO 9900376 A1 | 1/1999 |
| WO | WO 0146191 A1 | 6/2001 |
| WO | WO 0166543 A2 | 9/2001 |
| WO | WO 0172303 A1 | 10/2001 |
| WO | WO 0236573 A2 | 5/2002 |
| WO | WO 0248122 A2 | 6/2002 |
| WO | WO 03035646 A2 | 5/2003 |
| WO | WO 2004026030 A2 | 4/2004 |
| WO | WO 2004035541 A1 | 4/2004 |
| WO | WO 2004092165 A1 | 10/2004 |
| WO | WO 2005003131 A1 | 1/2005 |

OTHER PUBLICATIONS

Ananthan, S.: The AAPS Journal 2006, 8(1): E118-E125. (*in U.S. Appl. No. 10/873,527*).
Berge, S.M. et al.: Pharmaceutical Salts; J. of Pharmaceutical Sciences (1977) 66(1): 1-19.
Bidlack, J.M. et al.: 8-Carboxamidocyclazocine: A Long-Acting, Novel Benzomorphan; The J. of Pharm. & Exper. Therapeutics (2002) 302(1): 374-380.
Biemans et al.: Journal of Organic Chemistry, 1996, 61:9012-9015(*in U.S. Appl. No. 10/873,527*).
Boyd, R.E. et al.: Synthesis and Binding Affinities of 4-Diarylaminotropanes, a New Class of Delta Opioid Agonists; Bioorg. & Med. Chem. Letters (2000) 10: 1109-1111.
Calderon, S.N. et al: "SNC 80 and Related Opioid Agonists", Current Pharmaceutical Design, 2004 10:733-742(*in U.S. Appl. No. 11/195,231*).
Calo, et al.: British Journal of Pharmacology 2002, 136:303-311(*in U.S. Appl. No. 10/873,527*). Carson, J.R. et al., N-Alkyl-4-[(8-azabicyclo[3.2.1]-oct-3-ylidene)phenylmethyl]-benzamides, μ and δ opioid agonists: a μ address; Bioorganic & Med. Chem. Letters (2004) 14:2113-2116(*in U.S. Appl. No. 10/873,527*).
Chang et al.: Molecular Pharmacology, 1984, 26:484-488(*in U.S. Appl. No. 10/873,527*).
Commercial 2-Bromo-Phenols from Sigma-Aldrich. (*Created in U.S. Appl. No. 11/326,084.*).
Commercial 4-piperidinones. (*Created in U.S. Appl. No. 11/326,084.*).
Connor, M. et al.: Opioid Receptor Signalling Mechanisms; Clinical and Exper. Pharmacology and Physiology (1999) 26: 493-499. (*First in U.S. Appl. No. 10/873,527.*).

(Continued)

Primary Examiner — David K O'Dell

(57) ABSTRACT

The invention is directed to delta opioid receptor modulators. More specifically, the invention relates to tricyclic δ-opioid modulators. Pharmaceutical and veterinary compositions and methods of treating mild to severe pain and various diseases using compounds of the invention are also described.

22 Claims, No Drawings

OTHER PUBLICATIONS

Dorwald, F.Z.: Side Reactions in Organic Synthesis (2005) Wiley: VCH, Weinheim p. 1X of Preface: 1-15. (*in U.S. Appl. No. 10/873,527*).

Dörwald, F.Z.: Side Reactions in Organic Synthesis (2005) Wiley: VCH, Weinheim p. 1X of Preface & Chapter 8: 279-308. (*in U.S. Appl. No. 11/326,084*.).

Erchegyi et al.: Journal of Medicinal Chemistry, 2003, 46:5587-5596(*in U.S. Appl. No. 10/873,527*).

Frontier Scientific Catalog (Logan, UT) Advanced Discovery Chemicals Pure (*and not so*) Simple 2006; Discover Chemicals A-F, H-I, M-N, P-Q and T. (*in U.S. Appl. No. 11/314,300*.).

Frontier Scientific Catalog (Logan, UT) online http://www.frontiersci.com/browse.php?browse=Boronic%20acid Apr. 28, 2007 (in U.S. Appl. No. 11/195,231).

Furness, M.S. et al.: Probes and Narcotic Receptor-Mediated Phenomena. 27.[1] Synthesis and Pharmacological Evaluation of Selective δ-Opioid Receptor Agonists from 4-[α$R$)-α-(2S,5R)-4-Substituted-2,5-demethyl-1-piperazinyl-3-methoxybenzyl-]-$N,N$-diethylbenzamides and Their Enantiomers; J. Med. Chem. (2000) 43:3193-3196(*in U.S. Appl. No. 10/873,527*).

Gilbert, P.E. et al.: The Effects of Morphine- and Nalorphine-Like Drugs in the Nondependent, Morphine-Dependent and Cyclazocine-Dependent Chronic Spinal Dog; The J. of Pharm. and Exp. Thera. (1976) 198(1): 66-82.

Gould, P.L.: Salt selection for basic drugs; Intl J. of Pharmaceutics (1986) 33: 201-217.

Gribble, G.W. et al.: Sodium Triacetoxyborohydride1; Encyclopedia of Reagents for Organic Synthesis online @ http://www.mrw.interscience.wiley.com/eros/articles/rs112/sect0.html Apr. 24, 2007. (in U.S. Appl. No. 11/424,311.).

Gross, R.A. et al.: Dynorphin A and cAMP-dependent protein kinase independently regulate neuronal calcium currents; Proc. Natl. Acad. Sci. (1990) 87: 7025-7029.

Hancock, B.C. et al.: Characteristics and Significance of the Amorphous State in Pharmaceutical Systems; J. of Pharm. Sciences (1997) 86(1): 1-12.

Hutchins, R.O. et al.: Selective Reductive Displacement of Alkyl Halides and Sulfonate Esters with Cyanoborohydride Reagents in Hexamethylphosphoramide; J. Org. Chem. (1977) 42(1): 82-91. (*in U.S. Appl. No. 10/873,527*.).

Jones, M. Jr.: Organic Chemistry Norton, New York (1997):578-591(*in U.S. Appl. No. 11/424,311*).

Kenakin, T. et al.: The ligand paradox between affinity and efficacy: can you be there and not make a difference?; TRENDS in Pharm. Sciences (2002) 23(6): 275-280. (*in U.S. Appl. No. 11/326,084*.).

Kaiser, C. et al,: "Analogs of Phenothiazines. 5. Synthsis and Neuropharmacological Activity of Some Piperidylidene Derivatives of Thioxanthenes, Xanthenes, Dibenzoxepins, and Acridans." J. Med. Chem., 1974:57-61, vol. 17, No. 1.

Kruzsynski et al.: Journal of Peptide Research, 2005, 66:125-131(*in U.S. Appl. No. 10/873,527*).

Le Bars, D. et al.: Animal Models of Nociception; Pharmacological Reviews (2001) 53: 597-652. (*in U.S. Appl. No. 10/873,527*.).

Lord, John A.H. et al.: Endogenous opioid peptides: multiple agonists and receptors; Nature (1977) 267: 495-499.

Loughhead, David G.: Tetrahedron Letters, 1998, 5701-5702(*in U.S. Appl. No. 10/873,527*).

Mansour, A. et al.: Anatomy of CNS opioid receptors; TRENDS in Neuroscience (1988) 11(7): 308-314.

Nies and Speilberg, Goodman & Gilman, The Pharmacological Basis of Therapeutics, 1996, pp. 47, 58, Ninth Edition, vol. 1, McGraw-Hill, Interamericana, Mexico.

Nieschulz, O. et al.: "Pharmacological studies on 10-(1-methyl-3-piperidyl)-2 methoxyphenothiazine and related compounds"; Arzneimittel-Forschung 1960, 10, 156-165. (*in U.S. Appl. No. 11/326,084*.).

Pert, C.B. et al.: Opiate Receptor: Demonstration in Nervous Tissue; Science (1973) 179: 1011-1014.

Pozharskii et al.: Heterocycles in Life and Society, Wiley, 1997, pp. 1-6(*first in U.S. Appl. No. 11/195,231*).

Quock, R.M. et al.: The δ-Opioid Receptor: Molecular Pharmacology, Signal Transduction, and the Determination of Drug Efficacy; Pharmacological Reviews (1999) 51(3): 503-532. (*in U.S. Appl. No. 10/873,527*).

Sharma, S.K. et al.: Dual regulation of adenylate cyclase accounts for narcotic dependence and tolerance; Proc. Natl. Acad. Sci. (1975) 72(8): 3092-3096.

Still, W. Clark et al.: Rapid Chromatographic Technique for Preparative Separations with Moderate Resolution; J. Org. Chem. (1978) 43(14): 2923-2925.

Structures in copending U.S. Appl. No. 11/195,231. (*in U.S. Appl. No. 11/424,311*).

Sun, X. et al.: Synthesis and Opioid Receptor Binding Properties of Conformation-Rigidified Analogues of 8-Carboxamidocyclazocine and 8-Formamidocyclazocine; Abstract of Papers 229th ACS Natl Meeting NY 2005.

Tao, et al.: Bioorganic & Medicinal Chemistry Letters, 2006, 16:938-942(*in U.S. Appl. No. 10/873,527*).

Thomas, J.B. et al.: 4-[(8-Alkyl-8-azabicyclo[3.2.1]octyl-3-yl)-3-arylanilino]-$N,N$-diethylbenzamides: High Affinity, Selective Ligands for the Delta Opioid Receptor Illustrate Factors Important to Antagonist Activity; Bioorg. & Med. Chem. Letters (2000) 10(11): 1281-1284.

Thomas, J.B. et al.: (±)-4-[(N-Allyl-*CIS*-3-Methyl-4-Piperidinyl)Phenylamino]-$N,N$-Diethylbenzamide Displays Selective Binding for the Delta Opioid Receptor; Bioorg. & Med. Chem. Letters (1999) 9(20): 3053-3056.

Thomas, J.B. et al.: Factors Influencing Agonist Potency and Selectivity for the Opioid δ Receptor are Revealed in Structure—Activity Relationship Studies of the 4-[($N$-Substituted-4-piperidinyl)arylamino]-$N,N$-diethylbenzamides; J. Med. Chem. (2001) 44(6): 972-987.

Truce, W. E. et al.: The Smiles and Related Rearrangements of Aromatic Systems; Organic Reactions (1970) 18: 99-215.

Van Alstine, M.A. et al.: Synthesis and evaluation of novel N-substituted derivatives of 8-carboxamidocyclazocine; Abstract of Papers 231st ACS National Meeting, Atlanta, GA 2006, MEDI-009.

Walpole, C.S.J. et al.: The Discovery of Capsazepine, the First Competitive Antagonist of the Sensory Neuron Excitants Capsaicin and Resiniferatoxin; J. Med. Chem. (1994) 37: 1942-1954. (*in U.S. Appl. No. 11/314,300*.).

Wentland, M.P. et al.: 8-Aminocyclazocine Analogues: Synthesis and Structure—Activity Relationships[†]; Bioorg. & Med. Chem. Letters (2000) 10(2): 183-187.

Wentland, M.P. et al.: Selective Protection and Functionalization of Morphine: Synthesis and Opioid Receptor Binding Properties of 3-Amino-3-desoxymorphine Derivatives[†,1]; J. Med. Chem. (2000) 43(19): 3558-3565.

Wentland, M.P. et al.: 3-Carboxamido Analogues of Morphine and Naltrexone: Synthesis and Opioid Receptor Binding Properties; Bioorg. & Med. Chem. Letters (2001) 11: 1717-1721.

Wentland, M.P. et al.: 8-Carboxamidocyclazocine Analogues: Redefining the Structure—Activity Relationships of 2,6-Methano-3-benzazocines; Bioorg. & Med. Chem. Letters (2001) 11: 623-626.

Wentland, M.P. et al.: Syntheses and Opioid Receptor Binding Affinities of 8-Amino-2,6-methano-3-benzazocines; J. Med. Chem. (2003) 46: 838-849.

Wentland, M.P. et al.: Redefining the Structure—Activity Relationships of 2,6-Methano-3-benzazocines. Part 2: 8-Formamidocyclazocine Analogues; Bioorg. & Med. Chem. Letters (2003) 13: 1911-1914.

Wentland, M.P. et al.: Thioformamido and Thiocarboxamido Derivatives of Cyclazocine: Syntheses and Opioid Receptor Binding Properties; Abstract of Papers 226th ACS Natl. Meeting NY 2003.

Wentland, M.P. et al.: Redefining the structure—activity relationships of 2,6-methano-3-benzazocines. Part 3: 8-Thiocarboxamido and 8-thioformamido derivatives of cyclazocine; Bioorg. & Med. Chem. Letters (2005) 15: 2547-2551.

Wentland, M.P. et al.: Synthesis and opioid receptor binding properties of a highly potent 4-hydroxy analogue of naltrexone; Bioorg. & Med. Chem. Letters (2005) 15: 2107-2110.

West, A.R.: Solid State Chemistry and its Applications, Wiley, New York, 1988, pp. 358 & 365(*in U.S. Appl. No. 10/873,527*).

Wollemann, M.: Recent Developments in the Research of Opioid Receptor Subtype Molecular Characterization; J. of Neurochemistry (1990) 54(4): 1095-1101.

Zhang, A. et al.: 10-Ketomorphinan and 3-Substituted-3-desoxymorphinan Analogues as Mixed κ and μOpioid Ligands: Synthesis and Biological Evaluation of Their Binding Affinity at Opioid Receptors; J. Med. Chem. (2004) 47(1):165-174.

Zhang et al.,: Journal of Medicinal Chemistry, 1999, 42:5455-5463(*in U.S. Appl. No. 10/873,527*).

Sindelar, K., et al: Aminoalkylidene and Aminoalkyl Derivatives of 6,11-Dihydrodibenzo[be,e]Thiepin-2-and-9-Carbonitrile and 4,10-Dihydrothieno[2,3-e]-1-Benzothiepin-6-Carbonitrile; Antipressants with a New Activity Profile, Collection of Czechoslovak Chemical Communications (1988), vol. 63, No. 2, pp. 340-360.

PCT International Search Report, PCT/US2004/019911, Dec. 9, 2004, which relates to U.S. Appl. No. 10/873,527.

TRICYCLIC δ-OPIOID MODULATORS

CROSS REFERENCE TO RELATED APPLICATIONS

This Application is a divisional of application Ser. No. 13/157,846, filed Jun. 10, 2011 now U.S. Pat. No. 8,106,207, which is a divisional of application Ser. No. 12/536,635, filed Aug. 6, 2009 now U.S. Pat. No. 7,982,042, which is a divisional of application Ser. No. 10/873,527 filed Jun. 22, 2004, which issued as U.S. Pat. No. 7,589,103, which in turn claims priority to U.S. Provisional Patent Application No. 60/483,389, filed Jun. 27, 2003, now abandoned, which are hereby incorporated by reference in their entirety.

STATEMENT REGARDING FEDERALLY SPONSORED RESEARCH OR DEVELOPMENT

The research and development of the invention described below was not federally sponsored.

BACKGROUND OF THE INVENTION

The term "opioid" generically refers to all drugs, natural and synthetic, that have morphine-like actions. Formerly, the term "opiate" was used to designate drugs derived from opium, e.g., morphine, codeine, and many semi-synthetic congeners of morphine. After the isolation of peptide compounds with morphine-like actions, the term opioid was introduced to refer generically to all drugs with morphine-like actions. Included among opioids are various peptides that exhibit morphine-like activity, such as endorphins, enkephalins and dynorphins. However, some sources have continued to use the term "opiate" in a generic sense, and in such contexts, opiate and opioid are interchangeable. Additionally, the term opioid has been used to refer to antagonists of morphine-like drugs as well as to characterize receptors or binding sites that combine with such agents.

Opioids are generally employed as analgesics, but they may have many other pharmacological effects as well. Morphine and related opioids produce their major effects on the central nervous and digestive systems. The effects are diverse, including analgesia, drowsiness, mood changes, respiratory depression, dizziness, mental clouding, dysphoria, pruritus, increased pressure in the biliary tract, decreased gastrointestinal motility, nausea, vomiting, and alterations of the endocrine and autonomic nervous systems.

A significant feature of the analgesia produced by opioids is that it occurs without loss of consciousness. When therapeutic doses of morphine are given to patients with pain, they report that the pain is less intense, less discomforting, or entirely gone. In addition to experiencing relief of distress, some patients experience euphoria. However, when morphine in a selected pain-relieving dose is given to a pain-free individual, the experience is not always pleasant; nausea is common, and vomiting may also occur. Drowsiness, inability to concentrate, difficulty in mentation, apathy, lessened physical activity, reduced visual acuity, and lethargy may ensue.

Two distinct classes of opioid molecules can bind opioid receptors: the opioid peptides (e.g., the enkephalins, dynorphins, and endorphins) and the alkaloid opiates (e.g., morphine, etorphine, diprenorphine and naloxone). Subsequent to the initial demonstration of opiate binding sites (Pert, C. B. and Snyder, S. H., Science (1973) 179:1011-1014), the differential pharmacological and physiological effects of both opioid peptide analogues and alkaloid opiates served to delineate multiple opioid receptors. Accordingly, three anatomically and pharmacologically distinct opioid receptor types have been described: delta, kappa and mu. Furthermore, each type is believed to have sub-types (Wollemann, M., J Neurochem (1990) 54:1095-1101; Lord, J. A., et al., Nature (1977) 267:495-499).

All three of these opioid receptor types appear to share the same functional mechanisms at a cellular level. For example, the opioid receptors cause inhibition of adenylate cyclase, and inhibition of neurotransmitter release via both potassium channel activation and inhibition of $Ca^{2+}$ channels (Evans, C. J., In: Biological Basis of Substance Abuse, S. G. Korenman & J. D. Barchas, eds., Oxford University Press (in press); North, A. R., et al., Proc Natl Acad Sci USA (1990) 87:7025-29; Gross, R. A., et al., Proc Natl Acad Sci USA (1990) 87:7025-29; Sharma, S. K., et al., Proc Natl Acad Sci USA (1975) 72:3092-96). Although the functional mechanisms are the same, the behavioral manifestations of receptor-selective drugs differ greatly (Gilbert, P. E. & Martin, W. R., J Pharmacol Exp Ther (1976) 198:66-82). Such differences may be attributable in part to the anatomical location of the different receptors.

Delta receptors have a more discrete distribution within the mammalian CNS than either mu or kappa receptors, with high concentrations in the amygdaloid complex, striatum, substantia nigra, olfactory bulb, olfactory tubercles, hippocampal formation, and the cerebral cortex (Mansour, A., et al., Trends in Neurosci (1988) 11:308-14). The rat cerebellum is remarkably devoid of opioid receptors including delta opioid receptors.

D. Delorme, E. Roberts and Z. Wei, World Patent WO/28275 (1998) discloses diaryl methylidenylpiperidines that are opioid analgesics, but does not disclose or suggest the compounds of the present invention.

L. Hermann, C. Ullmer, E. Bellott and others, U.S. Pat. No. 0,166,672 (2003), World Patent WO/035646 (2003), and EP 1321169 (2003) disclose 4-(thio- or selenoxanthene-9-ylidene)-piperidines or acridines that are $5\text{-}HT_{2B}$ receptor antagonists, but do not disclose compounds of the present invention.

C. Kaiser, and others in J. Med. Chem. 1974, Volume 17, pages 57-61 disclose some piperidylidene derivatives of thioxanthenes, xanthenes, dibenoxepins and acridans that are neuroleptic agents. These authors, however, do not disclose or suggest either the structure or the activity of the compounds of the present invention.

British Patent GB 1128734 (1966) discloses derivatives of 6,11-dihydrodibenzo[b,e]oxepine that are anticholinergic, anti-convulsive, muscle-relaxing, sedating, diuretic, and/or circulatory-active agents. These, agents, however, differ significantly from the compounds of the present invention both structurally and pharmacologically.

There is a continuing need for new delta-opioid receptor modulators as analgesics. There is a further need for delta-opioid receptor selective agonists as analgesics having reduced side-effects. There is also a need for delta-opioid receptor antagonists as immunosuppressants, antiinflammatory agents, agents for the treatment of neurological and psychiatric conditions, medicaments for drug and alcohol abuse, agents for treating gastritis and diarrhea, cardiovascular agents and agents for the treatment of respiratory diseases, having reduced side-effects.

SUMMARY OF THE INVENTION

The present invention is directed to compositions comprising a compound of Formula (I):

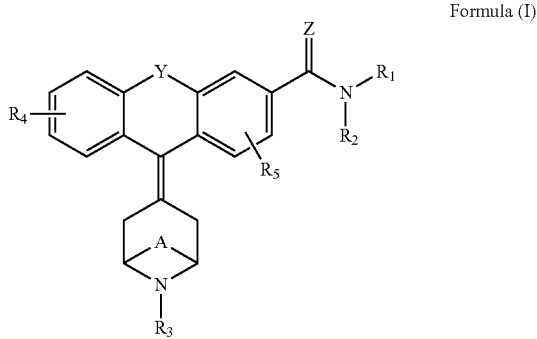

Formula (I)

wherein:
$R_1$ and $R_2$ are substituents independently selected from the group consisting of hydrogen and $C_{1-8}$alkanyl;
$R_3$ is selected from the group consisting of hydrogen, $C_{1-8}$alkanyl, halo$_{1-3}$($C_{1-8}$)alkanyl, $C_{2-8}$alkenyl, $C_{2-8}$alkynyl, $C_{3-8}$cycloalkanyl, cycloalkanyl($C_{1-8}$)alkanyl, $C_{1-8}$alkanyloxy($C_{1-8}$)alkanyl, $C_{1-8}$alkanylthio ($C_{1-8}$) alkanyl, hydroxy$C_{1-8}$alkanyl, $C_{1-8}$alkanyloxycarbonyl, halo$_{1-3}$($C_{1-8}$)alkanylcarbonyl, formyl, thioformyl, carbamimidoyl, phenylimino($C_{1-8}$)alkanyl, phenyl($C_{1-8}$)alkanyl, phenyl($C_{1-8}$)alkenyl, phenyl($C_{1-8}$)alkynyl, naphthyl($C_{1-8}$)alkanyl and heteroaryl($C_{1-8}$)alkanyl; wherein phenyl, naphthyl and heteroaryl are optionally substituted with one to three substituents independently selected from the group consisting of $C_{1-6}$alkanyl, $C_{2-6}$alkenyl, $C_{1-6}$alkanyloxy, amino, $C_{1-6}$alkanylamino, di($C_{1-6}$alkanyl)amino, $C_{1-6}$alkanylcarbonyl, $C_{1-6}$alkanylcarbonyloxy, $C_{1-6}$alkanylcarbonylamino, $C_{1-6}$alkanylthio, $C_{1-6}$alkanylsulfonyl, halogen, hydroxy, cyano, fluoroalkanyl, thioureido, and fluoroalkanyloxy; alternatively, when phenyl and heteroaryl are optionally substituted with two substituents attached to adjacent carbon atoms, the two substituents can together form a single fused moiety; wherein the fused moiety is selected from the group consisting of —(CH$_2$)$_{3-5}$— and —O(CH$_2$)$_{1-3}$O—;
$R_4$ is one to three substituents independently selected from the group consisting of hydrogen, $C_{1-6}$alkanyl, $C_{2-6}$alkenyl, $C_{1-6}$alkanyloxy, amino, $C_{1-6}$alkanylamino, di($C_{1-6}$alkanyl)amino, $C_{1-6}$alkanylcarbonyl, $C_{1-6}$alkanylcarbonyloxy, $C_{1-6}$alkanyloxycarbonyl, $C_{1-6}$alkanylaminocarbonyl, di($C_{1-6}$alkanyl)aminocarbonyl, $C_{1-6}$alkanylcarbonylamino, $C_{1-6}$alkanylthio, $C_{1-6}$alkanylsulfonyl, halogen, hydroxy, cyano, hydroxycarbonyl, $C_{6-10}$aryl, chromanyl, chromenyl, furanyl, imidazolyl, indazolyl, indolyl, indolinyl, isoindolinyl, isoquinolinyl, isothiazolyl, isoxazolyl, naphthyridinyl, oxazolyl, pyrazinyl, pyrazolyl, pyridazinyl, pyridinyl, pyrimidinyl, pyrrolyl, quinazolinyl, quinolinyl, quinolizinyl, quinoxalinyl, tetrazolyl, thiazolyl, thiophenyl, fluoroalkanyl and fluoroalkanyloxy; or optionally, when $R_4$ is two substituents attached to adjacent carbon atoms, the two substituents together form a single fused moiety; wherein the fused moiety is selected from the group consisting of —(CH$_2$)$_{3-5}$— and —O(CH$_2$)$_{1-3}$O—;
$R_5$ is one to two substituents independently selected from the group consisting of hydrogen, $C_{1-6}$alkanyl, $C_{2-6}$alkenyl, $C_{1-6}$alkanyloxy, amino, $C_{1-6}$alkanylamino, di($C_{1-6}$alkanyl)amino, $C_{1-6}$alkanylcarbonyl, $C_{1-6}$alkanylcarbonyloxy, $C_{1-6}$alkanyloxycarbonyl, $C_{1-6}$alkanylaminocarbonyl, $C_{1-6}$alkanylcarbonylamino, $C_{1-6}$alkanylthio, $C_{1-6}$alkanylsulfonyl, halogen, hydroxy, cyano, fluoroalkanyl and fluoroalkanyloxy;
A is —(CH$_2$)$_m$—, wherein m is 0, 2 or 3; preferably, m is 2 or 3, and most preferably, m is 2
Y is —(CH$_2$)$_n$X— or —X(CH$_2$)$_n$—;
X is O or S
n is 0 or 1;
Z is O or S;
and enantiomers, diastereomers, tautomers, solvates, or pharmaceutically acceptable salts thereof.

Finally, the present invention is directed to veterinary and pharmaceutical compositions containing compounds of Formula (I) wherein the compositions are used to treat mild to severe pain in warm-blooded animals.

DETAILED DESCRIPTION OF THE INVENTION

As used herein, the following underlined terms are intended to have the following meanings:

"$C_{a-b}$" (where a and b are integers) refers to a radical containing from a to b carbon atoms inclusive. For example, $C_{1-3}$ denotes a radical containing 1, 2 or 3 carbon atoms "Alkyl:" refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl ( ), prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl", "alkenyl" and/or "alkynyl" is used, as defined below. In preferred embodiments, the alkyl groups are ($C_1$-$C_6$) alkyl, with ($C_1$-$C_3$) being particularly preferred.

"Alkanyl:" refers to a saturated branched, straight-chain or cyclic monovalent hydrocarbon radical derived by the removal of one hydrogen atom from a single carbon atom of a parent alkane. Typical alkanyl groups include, but are not limited to, methanyl; ethanyl; propanyls such as propan-1-yl, propan-2-yl, cyclopropan-1-yl, etc.; butyanyls such as butan-1-yl, butan-2-yl, 2-methyl-propan-1-yl, 2-methyl-propan-2-yl, cyclobutan-1-yl, etc.; and the like. In preferred embodiments, the alkanyl groups are ($C_{1-8}$) alkanyl, with ($C_{1-3}$) being particularly preferred.

"Alkenyl" refers to an unsaturated branched, straight-chain or cyclic monovalent hydrocarbon radical having at least one carbon-carbon double bond derived by the removal of one hydrogen atom from a single carbon atom of a parent alkene. The radical may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkenyl" refers to an unsaturated branched, straight-chain or cyclic monovalent hydrocarbon radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Heteroalkyl" and Heteroalkanyl" refer to alkyl or alkanyl radicals, respectively, in which one or more carbon atoms (and any necessary associated hydrogen atoms) are independently replaced with the same or different heteroatoms (including any necessary hydrogen or other atoms). Typical heteroatoms to replace the carbon atom(s) include, but are not limited to, N, P, O, S, Si, etc. Preferred heteroatoms are O, N and S. Thus, heteroalkanyl radicals can contain one or more of the same or different heteroatomic groups, including, by way of example and not limitation, epoxy (—O—), epidioxy (—O—O—), thioether (—S—), epidithio (—SS—), epoxythio (—O—S—), epoxyimino (—O—NR'—), imino (—NR'—), biimino (—NR'—NR'—), azino (=N—N=), azo (—N=N—), azoxy (—N—O—N—), azimino (—NR'—N=N—), phosphano (—PH—), $\lambda^4$-sulfano (—SH$_2$—), sulfonyl (—S(O)$_2$—), and the like, where each R' is independently hydrogen or (C$_1$-C$_6$) alkyl.

"Parent Aromatic Ring System:" refers to an unsaturated cyclic or polycyclic ring system having a conjugated π electron system. Specifically included within the definition of "parent aromatic ring system" are fused ring systems in which one or more rings are aromatic and one or more rings are saturated or unsaturated, such as, for example, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like "Aryl:" refers to a monovalent aromatic hydrocarbon radical derived by the removal of one hydrogen atom from a single carbon atom of a parent aromatic ring system. Typical aryl groups include, but are not limited to, radicals derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In preferred embodiments, the aryl group is (C$_{5-20}$) aryl, with (C$_{5-10}$) being particularly preferred. Particularly preferred aryl groups are phenyl and naphthyl groups.

"Arylalkyl:" refers to an acyclic alkyl group in which one of the hydrogen atoms bonded to a carbon atom, typically a terminal carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. [In preferred embodiments, the arylalkyl group is (C$_{6-26}$) arylalkyl, e.g., the alkanyl, alkenyl or alkynyl moiety of the arylalkyl group is (C$_{1-6}$) and the aryl moiety is (C$_{5-20}$). In particularly preferred embodiments the arylalkyl group is (C$_{6-13}$), e.g., the alkanyl, alkenyl or alkynyl moiety of the arylalkyl group is (C$_{1-3}$) and the aryl moiety is (C$_{5-10}$). Even more preferred arylalkyl groups are phenylalkanyls.

"Alkanyloxy:" refers to a saturated branched, straight-chain or cyclic monovalent hydrocarbon alcohol radical derived by the removal of the hydrogen atom from the hydroxide oxygen of the alcohol. Typical alkanyloxy groups include, but are not limited to, methanyloxy; ethanyloxy; propanyloxy groups such as propan-1-yloxy (CH$_3$CH$_2$CH$_2$O—), propan-2-yloxy ((CH$_3$)$_2$CHO—), cyclopropan-1-yloxy, etc.; butanyloxy groups such as butan-1-yloxy, butan-2-yloxy, 2-methyl-propan-1-yloxy, 2-methyl-propan-2-yloxy, cyclobutan-1-yloxy, etc.; and the like. In preferred embodiments, the alkanyloxy groups are (C$_{1-8}$) alkanyloxy groups, with (C$_{1-3}$) being particularly preferred.

"Parent Heteroaromatic Ring System:" refers to a parent aromatic ring system in which one carbon atom is replaced with a heteroatom. Heteratoms to replace the carbon atoms include N, O, and S. Specifically included within the definition of "parent heteroaromatic ring systems" are fused ring systems in which one or more rings are aromatic and one or more rings are saturated or unsaturated, such as, for example, arsindole, chromane, chromene, indole, indoline, xanthene, etc. Typical parent heteroaromatic ring systems include, but are not limited to, carbazole, imidazole, indazole, indole, indoline, indolizine, isoindole, isoindoline, isoquinoline, isothiazole, isoxazole, naphthyridine, oxadiazole, oxazole, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Heteroaryl:" refers to a monovalent heteroaromatic radical derived by the removal of one hydrogen atom from a single atom of a parent heteroaromatic ring system. Typical heteroaryl groups include, but are not limited to, radicals derived from carbazole, imidazole, indazole, indole, indoline, indolizine, isoindole, isoindoline, isoquinoline, isothiazole, isoxazole, naphthyridine, oxadiazole, oxazole, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In preferred embodiments, the heteroaryl group is a 5-20 membered heteroaryl, with 5-10 membered heteroaryl being particularly preferred.

"Cycloheteroalkyl:" refers to a saturated or unsaturated monocyclic or bicyclic alkyl radical in which one carbon atom is replaced with N, O or S. In certain specified embodiments the cycloheteroalkyl may contain up to four heteroatoms independently selected from N, O or S. Typical cycloheteroalkyl moieties include, but are not limited to, radicals derived from imidazolidine, morpholine, piperazine, piperidine, pyrazolidine, pyrrolidine, quinuclidine, and the like. In preferred embodiments, the cycloheteroalkyl is a 3-6 membered cycloheteroalkyl.

"Cycloheteroalkanyl:" refers to a saturated monocyclic or bicyclic alkanyl radical in which one carbon atom is replaced with N, O or S. In certain specified embodiments the cycloheteroalkanyl may contain up to four heteroatoms independently selected from N, O or S. Typical cycloheteroalkanyl moieties include, but are not limited to, radicals derived from imidazolidine, morpholine, piperazine, piperidine, pyrazolidine, pyrrolidine, quinuclidine, and the like. In preferred embodiments, the cycloheteroalkanyl is a 3-6 membered cycloheteroalkanyl.

"Cycloheteroalkenyl:" refers to a saturated monocyclic or bicyclic alkenyl radical in which one carbon atom is replaced with N, O or S. In certain specified embodiments the cycloheteroalkenyl may contain up to four heteroatoms independently selected from N, O or S. Typical cycloheteroalkenyl moieties include, but are not limited to, radicals derived from imidazoline, pyrazoline, pyrroline, indoline, pyran, and the like. In preferred embodiments, the cycloheteroalkanyl is a 3-6 membered cycloheteroalkanyl.

"Substituted:" refers to a radical in which one or more hydrogen atoms are each independently replaced with the same or different substituent(s). Typical substituents include, but are not limited to, —X, —R, —O⁻, =O, —OR, —O—OR, —SR, —S⁻, =S, —NRR, =NR, —CX$_3$, —CN, —OCN, —SCN, —NCO, —NCS, —NO, —NO$_2$, =N$_2$, —N$_3$, —NHOH, —S(O)$_2$O⁻, —S(O)$_2$OH, —S(O)$_2$R, —P(O)(O⁻)$_2$, —P(O)(OH)$_2$, —C(O)R, —C(O)X, —C(S)R, —C(S)X, —C(O)OR, —C(O)O⁻, —C(S)OR, —C(O)SR, —C(S)SR, —C(O)NRR, —C(S)NRR and —C(NR)NRR, where each X is independently a halogen (preferably —F, —Cl or —Br) and each R is independently —H, alkyl, alkanyl, alkenyl, alkynyl, alkylidene, alkylidyne, aryl, arylalkyl, arylheteroalkyl, heteroaryl, heteroarylalkyl or heteroaryl-heteroalkyl, as defined herein. Preferred substituents include hydroxy, halogen, $C_{1-8}$alkyl, $C_{1-8}$alkanyloxy, fluorinated alkanyloxy, fluorinated alkyl, $C_{1-8}$alkylthio, $C_{3-8}$cycloalkyl, $C_{3-8}$cycloalkanyloxy, nitro, amino, $C_{1-8}$alkylamino, $C_{1-8}$dialkylamino, $C_{3-8}$cycloalkylamino, cyano, carboxy, $C_{1-7}$alkanyloxycarbonyl, $C_{1-7}$alkylcarbonyloxy, formyl, carbamoyl, phenyl, aroyl, carbamoyl, amidino, ($C_{1-8}$alkylamino)carbonyl, (arylamino)carbonyl and aryl($C_{1-8}$alkyl)carbonyl.

With reference to substituents, the term "independently" means that when more than one of such substituent is possible, such substituents may be the same or different from each other.

Throughout this disclosure, the terminal portion of the designated side chain is described first, followed by the adjacent functionality toward the point of attachment. Thus, for example, a "phenyl$C_{1-6}$alkanylaminocarbonyl$C_{1-6}$alkyl" substituent refers to a group of the formula

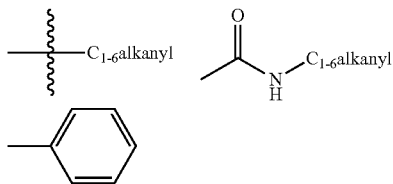

An embodiment of the present invention is directed to a compound of Formula (I) wherein the structure is numbered as defined herein.

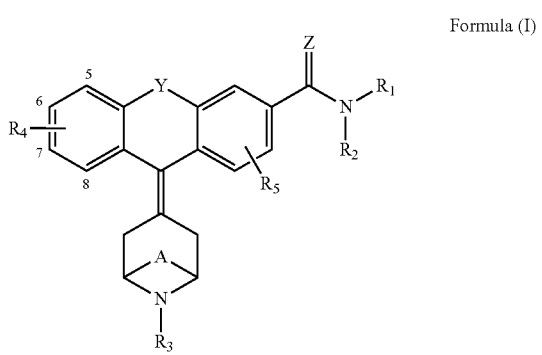

Formula (I)

The present invention is directed to analgesic and antipyretic uses of compositions comprising a compound of Formula (I):

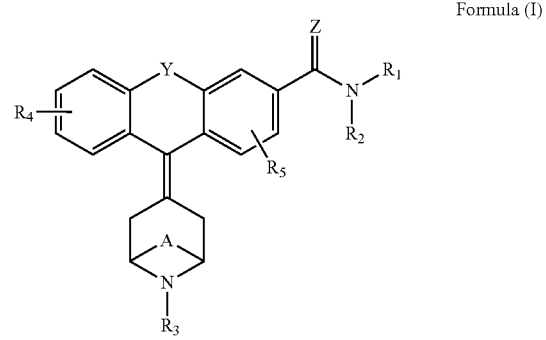

Formula (I)

wherein:

$R_1$ and $R_2$ are substituents independently selected from the group consisting of hydrogen and $C_{1-8}$alkanyl;

$R_3$ is selected from the group consisting of hydrogen, $C_{1-8}$alkanyl, halo$_{1-3}$($C_{1-8}$)alkanyl, $C_{2-8}$alkenyl, $C_{2-8}$alkynyl, $C_{3-8}$cycloalkanyl, cycloalkanyl($C_{1-8}$)alkanyl, $C_{1-8}$alkanyloxy($C_{1-8}$)alkanyl, $C_{1-8}$alkanylthio ($C_{1-8}$)alkanyl, hydroxy$C_{1-8}$alkanyl, $C_{1-8}$alkanyloxycarbonyl, halo$_{1-3}$($C_{1-8}$)alkanylcarbonyl, formyl, thioformyl, carbamimidoyl, phenylimino($C_{1-8}$)alkanyl, phenyl($C_{1-8}$)alkanyl, phenyl($C_{1-8}$)alkenyl, phenyl($C_{1-8}$) alkynyl, naphthyl($C_{1-8}$)alkanyl and heteroaryl($C_{1-8}$)alkanyl; wherein phenyl, naphthyl and heteroaryl are optionally substituted with one to three substituents independently selected from the group consisting of $C_{1-6}$alkanyl, $C_{2-6}$alkenyl, $C_{1-6}$alkanyloxy, amino, $C_{1-6}$alkanylamino, di($C_{1-6}$alkanyl)amino, $C_{1-6}$alkanylcarbonyl, $C_{1-6}$alkanylcarbonyloxy, $C_{1-6}$alkanylcarbonylamino, $C_{1-6}$alkanylthio, $C_{1-6}$alkanylsulfonyl, halogen, hydroxy, cyano, fluoroalkanyl, thioureido, and fluoroalkanyloxy; or optionally, when phenyl and heteroaryl are optionally substituted with two substituents attached to adjacent carbon atoms, the two substituents together form a single fused moiety; wherein the fused moiety is selected from the group consisting of —(CH$_2$)$_{3-5}$— and —O(CH$_2$)$_{1-3}$O—;

$R_4$ is one to three substituents independently selected from the group consisting of hydrogen, $C_{1-6}$alkanyl, $C_{2-6}$alkenyl, $C_{1-6}$alkanyloxy, amino, $C_{1-6}$alkanylamino, di($C_{1-6}$alkanyl)amino, $C_{1-6}$alkanylcarbonyl, $C_{1-6}$alkanylcarbonyloxy, $C_{1-6}$alkanyloxycarbonyl, $C_{1-6}$alkanylaminocarbonyl, di($C_{1-6}$alkanyl)aminocarbonyl, $C_{1-6}$alkanylcarbonylamino, $C_{1-6}$alkanylthio, $C_{1-6}$alkanylsulfonyl, halogen, hydroxy, cyano, hydroxycarbonyl, $C_{6-10}$aryl, chromanyl, chromenyl, furanyl, imidazolyl, indazolyl, indolyl, indolinyl, isoindolinyl, isoquinolinyl, isothiazolyl, isoxazolyl, naphthyridinyl, oxazolyl, pyrazinyl, pyrazolyl, pyridazinyl, pyridinyl, pyrimidinyl, pyrrolyl, quinazolinyl, quinolinyl, quinolizinyl, quinoxalinyl, tetrazolyl, thiazolyl, thiophenyl, fluoroalkanyl and fluoroalkanyloxy; or optionally, when $R_4$ is two substituents attached to adjacent carbon atoms, the two substituents together form a single fused moiety; wherein the fused moiety is selected from the group consisting of —(CH$_2$)$_{3-5}$— and —O(CH$_2$)$_{1-3}$O—;

$R_5$ is one to two substituents independently selected from the group consisting of hydrogen, $C_{1-6}$alkanyl, $C_{2-6}$alkenyl, $C_{1-6}$alkanyloxy, amino, $C_{1-6}$alkanylamino, di($C_{1-6}$alkanyl)amino, $C_{1-6}$alkanylcarbonyl, $C_{1-6}$alkanylcarbonyloxy, $C_{1-6}$alkanyloxycarbonyl, $C_{1-6}$alkanylaminocarbonyl, $C_{1-6}$alkanylcarbonylamino, $C_{1-6}$alkanylthio, $C_{1-6}$alkanylsulfonyl, halogen, hydroxy, cyano, fluoroalkanyl and fluoroalkanyloxy;

A is —$(CH_2)_m$—, wherein m is 0, 2 or 3;

Y is —$(CH_2)_nX$— or —$X(CH_2)_n$—;

X is O or S;

n is 0 or 1;

Z is O or S;

and enantiomers, diastereomers, tautomers, solvates, and pharmaceutically acceptable salts thereof.

For embodiments of the present invention, preferably:

a) $R_1$ and $R_2$ are substituents independently selected from the group consisting of hydrogen and $C_{1-4}$alkanyl;

b) $R_1$ and $R_2$ are substituents independently selected from the group consisting of hydrogen, methyl, ethyl and propyl;

c) $R_1$ and $R_2$ are substituents independently selected from the group consisting of hydrogen and ethyl;

d) $R_3$ is selected from the group consisting of hydrogen, $C_{1-8}$alkanyl, $C_{2-8}$alkenyl, $C_{2-8}$alkynyl, $C_{1-8}$alkanyloxy($C_{1-8}$)alkanyl, $C_{1-8}$alkanylthio($C_{1-8}$)alkanyl, hydroxy$C_{1-8}$alkanyl, thioformyl, phenylimino($C_{1-8}$)alkanyl, phenyl($C_{1-8}$)alkanyl, and heteroaryl($C_{1-8}$)alkanyl; wherein phenyl and heteroaryl are optionally substituted with one to three substituents independently selected from the group consisting of $C_{1-6}$alkanyloxy and hydroxy; or optionally, when phenyl and heteroaryl are optionally substituted with two substituents attached to adjacent carbon atoms, the two substituents together form a single fused moiety; wherein the moiety is selected from —$O(CH_2)_{1-3}O$—;

e) $R_3$ is selected from the group consisting of hydrogen, methyl, allyl, 2-methyl-allyl, propynyl, hydroxyethyl, methylthioethyl, methoxyethyl, thioformyl, phenyliminomethyl, phenethyl, and heteroaryl($C_{1-8}$)alkanyl; wherein the phenyl in any phenyl-containing substituent is optionally substituted with one hydroxyl group;

f) $R_3$ is hydrogen, methyl, allyl, or heteroarylmethyl;

g) $R_4$ is one to three substituents independently selected from the group consisting of hydrogen, $C_{1-6}$alkanyl, $C_{1-6}$alkanyloxy, $C_{1-6}$alkanylaminocarbonyl, $C_{1-6}$alkanylcarbonylamino, halogen, hydroxy, $C_{6-10}$aryl, chromanyl, chromenyl, furanyl, imidazolyl, indazolyl, indolyl, indolinyl, isoindolinyl, isoquinolinyl, isothiazolyl, isoxazolyl, naphthyridinyl, oxazolyl, pyrazinyl, pyrazolyl, pyridazinyl, pyridinyl, pyrimidinyl, pyrrolyl, quinazolinyl, quinolinyl, quinolizinyl, quinoxalinyl, tetrazolyl, thiazolyl, and thiophenyl;

h) $R_4$ is one to two substituents independently selected from the group consisting of hydrogen, $C_{1-4}$alkanyl, $C_{1-4}$alkanyloxy, halogen, phenyl, furanyl, imidazolyl, indazolyl, indolyl, indolinyl, isoindolinyl, isoquinolinyl, isothiazolyl, isoxazolyl, oxazolyl, pyrazinyl, pyrazolyl, pyridazinyl, pyridinyl, pyrimidinyl, pyrrolyl, quinolinyl, tetrazolyl, thiazolyl, thiophenyl, and hydroxy;

i) $R_4$ is one to two substituents independently selected from the group consisting of hydrogen, methyl, methoxy, bromo, fluoro, 5- or 6-phenyl, 5- or 6-pyridinyl, 5- or 6-furanyl, and hydroxy;

j) $R_5$ is one to two substituents independently selected from the group consisting of hydrogen and halogen;

k) $R_5$ is hydrogen;

l) A is —$(CH_2)_{0-2}$—;

m) A is —$(CH_2)_2$—;

n) X is O or S;

o) n is 0;

p) Z is O; and q) combinations of a) through p) above.

One embodiment of the present invention is a compound of Formula (I) wherein:

$R_1$ is $C_{1-3}$alkanyl;

$R_2$ is $C_{1-3}$alkanyl or hydrogen;

$R_3$ is selected from the group consisting of hydrogen, $C_{1-8}$alkanyl, $C_{2-8}$alkenyl, $C_{2-8}$alkynyl, $C_{1-8}$alkanyloxy($C_{1-8}$)alkanyl, $C_{1-8}$alkanylthio($C_{1-8}$)alkanyl, hydroxy$C_{1-8}$alkanyl, thioformyl, phenylimino($C_{1-8}$)alkanyl, phenyl($C_{1-8}$)alkanyl, and heteroaryl($C_{1-8}$)alkanyl; wherein phenyl and heteroaryl are optionally substituted with one to three substituents independently selected from the group consisting of $C_{1-6}$alkanyloxy and hydroxy; or optionally, when phenyl and heteroaryl are optionally substituted with two substituents attached to adjacent carbon atoms, the two substituents together form a single fused moiety; wherein the moiety is selected from —$O(CH_2)_{1-3}O$—;

$R_4$ is one to three substituents independently selected from the group consisting of hydrogen, $C_{1-6}$alkanyl, $C_{1-6}$alkanyloxy, $C_{1-6}$alkanylaminocarbonyl, $C_{1-6}$alkanylcarbonylamino, halogen, hydroxy, $C_{6-10}$aryl, chromanyl, chromenyl, furanyl, imidazolyl, indazolyl, indolyl, indolinyl, isoindolinyl, isoquinolinyl, isothiazolyl, isoxazolyl, naphthyridinyl, oxazolyl, pyrazinyl, pyrazolyl, pyridazinyl, pyridinyl, pyrimidinyl, pyrrolyl, quinazolinyl, quinolinyl, quinolizinyl, quinoxalinyl, tetrazolyl, thiazolyl, and thiophenyl;

$R_5$ is one to two substituents independently selected from the group consisting of hydrogen and halogen;

A is absent or $CH_2CH_2$;

Y is O, S, $CH_2O$ or $OCH_2$;

Z is O; and enantiomers, diastereomers, tautomers, solvates, and pharmaceutically acceptable salts thereof.

Another embodiment of the present invention is a compound of Formula (I) wherein:

$R_1$ is $C_{1-3}$alkanyl;

$R_2$ is $C_{1-3}$alkanyl or hydrogen;

$R_3$ is selected from the group consisting of hydrogen, methyl, allyl, 2-methyl-allyl, propynyl, hydroxyethyl, methoxyethyl, methylthioethyl, thioformyl, phenyliminomethyl, phenethyl, and heteroaryl($C_{1-8}$)alkanyl; wherein the phenyl in any phenyl-containing substituent is optionally substituted with one hydroxyl group;

$R_4$ is one to two substituents independently selected from the group consisting of hydrogen, $C_{1-4}$alkanyl, $C_{1-4}$alkanyloxy, halogen, phenyl, furanyl, imidazolyl, indazolyl, indolyl, indolinyl, isoindolinyl, isoquinolinyl, isothiazolyl, isoxazolyl, oxazolyl, pyrazinyl, pyrazolyl, pyridazinyl, pyridinyl, pyrimidinyl, pyrrolyl, quinolinyl, tetrazolyl, thiazolyl, thiophenyl, and hydroxy;

$R_5$ is hydrogen;

A is absent or $CH_2CH_2$;

Y is O, S, $CH_2O$ or $OCH_2$;

Z is O; and enantiomers, diastereomers, tautomers, solvates, and pharmaceutically acceptable salts thereof.

Another embodiment of the present invention is directed to compositions comprising a compound of Formula (I) wherein $R_1$ is ethyl; $R_2$ is ethyl or hydrogen; $R_3$ is a substituent selected from the group consisting of benzo[1,3]dioxol-5-ylmethyl, carbamimidoyl, 1-H-imidazol-4-ylmethyl, phenyliminomethyl, 1-prop-2-ynyl, thioformyl, 2-hydroxyphenyl-methyl, hydroxy-ethyl, methoxy-ethyl, 2-methyl-allyl, 2-methyl-but-2-enyl, allyl, furan-3-ylmethyl, H, Me, methylthioethyl, phenethyl, pyridin-2-yl methyl, thiophen-2-yl methyl; $R_4$ is one to two substituents independently selected from the group consisting of hydrogen, $C_{1-4}$alkanyl, $C_{1-4}$alkanyloxy, halogen, phenyl, furanyl, imidazolyl, indazolyl, indolyl, indolinyl, isoindolinyl, isoquinolinyl, isothiazolyl, isoxazolyl, oxazolyl, pyrazinyl, pyrazolyl, pyridazinyl, pyridinyl, pyrimidinyl, pyrrolyl, quinolinyl, tetrazolyl, thiazolyl, thiophenyl, and hydroxy; A is absent or $CH_2CH_2$; Y is O or S; and Z is O.

Another embodiment of the present invention is a compound of Formula (I) wherein:

$R_1$ is $C_{1-3}$alkanyl;

$R_2$ is $C_{1-3}$alkanyl or hydrogen;

$R_3$ is selected from the group consisting of hydrogen, $C_{1-8}$alkanyl, $C_{2-8}$alkenyl, $C_{2-8}$alkynyl, $C_{1-8}$alkanyloxy $(C_{1-8})$alkanyl, $C_{1-8}$alkanylthio$(C_{1-8})$alkanyl, hydroxy$C_{1-8}$alkanyl, thioformyl, phenylimino$(C_{1-8})$alkanyl, phenyl$(C_{1-8})$alkanyl, and heteroaryl$(C_{1-8})$alkanyl; wherein phenyl and heteroaryl are optionally substituted with one to three substituents independently selected from the group consisting of $C_{1-6}$alkanyloxy and hydroxy; or optionally, when phenyl and heteroaryl are optionally substituted with two substituents attached to adjacent carbon atoms, the two substituents together form a single fused moiety; wherein the moiety is selected from —$O(CH_2)_{1-3}O$—;

$R_4$ is one to three substituents independently selected from the group consisting of hydrogen, $C_{1-6}$alkanyl, $C_{1-6}$alkanyloxy, $C_{1-6}$alkanylaminocarbonyl, $C_{1-6}$alkanylcarbonylamino, halogen, hydroxy, $C_{6-10}$aryl, chromanyl, chromenyl, furanyl, imidazolyl, indazolyl, indolyl, indolinyl, isoindolinyl, isoquinolinyl, isothiazolyl, isoxazolyl, naphthyridinyl, oxazolyl, pyrazinyl, pyrazolyl, pyridazinyl, pyridinyl, pyrimidinyl, pyrrolyl, quinazolinyl, quinolinyl, quinolizinyl, quinoxalinyl, tetrazolyl, thiazolyl, and thiophenyl;

$R_5$ is one to two substituents independently selected from the group consisting of hydrogen and halogen;

A $CH_2CH_2$;

Y is O, S, $CH_2O$ or $OCH_2$;

Z is O; and enantiomers, diastereomers, tautomers, solvates, and pharmaceutically acceptable salts thereof.

Another embodiment of the present invention is a compound of Formula (I) wherein:

$R_1$ is $C_{1-3}$alkanyl;

$R_2$ is $C_{1-3}$alkanyl or hydrogen;

$R_3$ is selected from the group consisting of hydrogen, methyl, allyl, 2-methyl-allyl, propynyl, hydroxyethyl, methoxyethyl, methylthioethyl, thioformyl, phenyliminomethyl, phenethyl, and heteroaryl$(C_{1-8})$alkanyl; wherein the phenyl in any phenyl-containing substituent is optionally substituted with one hydroxyl group;

$R_4$ is one to two substituents independently selected from the group consisting of hydrogen, $C_{1-4}$alkanyl, $C_{1-4}$alkanyloxy, halogen, phenyl, furanyl, imidazolyl, indazolyl, indolyl, indolinyl, isoindolinyl, isoquinolinyl, isothiazolyl, isoxazolyl, oxazolyl, pyrazinyl, pyrazolyl, pyridazinyl, pyridinyl, pyrimidinyl, pyrrolyl, quinolinyl, tetrazolyl, thiazolyl, thiophenyl, and hydroxy;

$R_5$ is hydrogen;

A is $CH_2CH_2$;

Y is O, S, $CH_2O$ or $OCH_2$;

Z is O; and enantiomers, diastereomers, tautomers, solvates, and pharmaceutically acceptable salts thereof.

Another embodiment of the present invention is directed to compositions comprising a compound of Formula (I) wherein $R_1$ is ethyl; $R_2$ is ethyl or hydrogen; $R_3$ is a substituent selected from the group consisting of benzo[1,3]dioxol-5-ylmethyl, carbamimidoyl, 1-H-imidazol-4-ylmethyl, phenyliminomethyl, 1-prop-2-ynyl, thioformyl, 2-hydroxyphenyl-methyl, hydroxy-ethyl, methoxy-ethyl, 2-methyl-allyl, 2-methyl-but-2-enyl, allyl, furan-3-ylmethyl, H, Me, methylthioethyl, phenethyl, pyridin-2-yl methyl, thiophen-2-yl methyl; $R_4$ is one to two substituents independently selected from the group consisting of hydrogen, $C_{1-4}$alkanyl, $C_{1-4}$alkanyloxy, halogen, phenyl, furanyl, imidazolyl, indazolyl, indolyl, indolinyl, isoindolinyl, isoquinolinyl, isothiazolyl, isoxazolyl, oxazolyl, pyrazinyl, pyrazolyl, pyridazinyl, pyridinyl, pyrimidinyl, pyrrolyl, quinolinyl, tetrazolyl, thiazolyl, thiophenyl, and hydroxy; A is $CH_2CH_2$; Y is O or S; and Z is O.

Another embodiment of the present invention is directed to compositions comprising a compound of Formula (I) wherein $R_1$ is ethyl; $R_2$ is ethyl; $R_3$ is a substituent selected from the group consisting of benzo[1,3]dioxol-5-ylmethyl, carbamimidoyl, 1-H-imidazol-4-yl methyl, phenyliminomethyl, 1-prop-2-ynyl, thioformyl, 2-hydroxyphenyl-methyl, hydroxyethyl, methoxyethyl, allyl, furan-3-yl methyl, H, Me, methylthioethyl, and phenethyl; $R_4$ is one to two substituents independently selected from the group consisting of hydrogen, methyl, methoxy, bromo, fluoro, 5- or 6-phenyl, 5- or 6-pyridinyl, 5- or 6-furanyl, and hydroxy; A is $CH_2CH_2$; Y is O or S; and Z is O.

Another embodiment of the present invention is directed to compositions comprising a compound of Formula (I) wherein $R_1$ is ethyl; $R_2$ is ethyl; $R_3$ is a substituent selected from the group consisting of H, benzo[1,3]dioxol-5-ylmethyl, 1-H-imidazol-4-yl methyl, furan-3-ylmethyl, pyridin-2-ylmethyl, and phenyliminomethyl; $R_4$ is a substituent independently selected from the group consisting of hydrogen, methyl, methoxy, bromo, fluoro, 5- or 6-phenyl, 5- or 6-pyridinyl, 5- or 6-furanyl, and hydroxy; A is $CH_2CH_2$; Y is O or S; and Z is O.

Another embodiment of the present invention is directed to a compound of Formula (I) wherein $R_4$ is preferably substituted at the 5- or 6-position of Formula (I).

Another embodiment of the present invention is directed to compositions comprising a compound selected from the group consisting of:

a compound of Formula (I) wherein $R_1$ is ethyl, $R_2$ is ethyl, $R_3$ is methyl, $R_4$ is H, $R_5$ is H, A is absent, Y is $CH_2O$, and Z is O;

a compound of Formula (I) wherein $R_1$ is ethyl, $R_2$ is ethyl, $R_3$ is H, $R_4$ is H, $R_5$ is H, A is absent, Y is $CH_2O$, and Z is O;

a compound of Formula (I) wherein $R_1$ is ethyl, $R_2$ is ethyl, $R_3$ is H, $R_4$ is H, $R_5$ is H, A is absent, Y is O, and Z is O;

a compound of Formula (I) wherein $R_1$ is ethyl, $R_2$ is ethyl, $R_3$ is benzo[1,3]dioxol-5-ylmethyl, $R_4$ is H, $R_5$ is H, A is absent, Y is $CH_2O$, and Z is O;

a compound of Formula (I) wherein $R_1$ is ethyl, $R_2$ is ethyl, $R_3$ is phenethyl, $R_4$ is H, $R_5$ is H, A is absent, Y is $CH_2O$, and Z is O;

a compound of Formula (I) wherein $R_1$ is ethyl, $R_2$ is ethyl, $R_3$ is allyl, $R_4$ is H, $R_5$ is H, A is absent, Y is $CH_2O$, and Z is O;

a compound of Formula (I) wherein $R_1$ is ethyl, $R_2$ is ethyl, $R_3$ is methyl, $R_4$ is H, $R_5$ is H, A is absent, Y is O, and Z is O;

a compound of Formula (I) wherein $R_1$ is ethyl, $R_2$ is ethyl, $R_3$ is allyl, $R_4$ is H, $R_5$ is H, A is absent, Y is O, and Z is O;

a compound of Formula (I) wherein $R_1$ is ethyl, $R_2$ is H, $R_3$ is methyl, $R_4$ is H, $R_5$ is H, A is absent, Y is $CH_2O$, and Z is O;

a compound of Formula (I) wherein $R_1$ is ethyl, $R_2$ is H, $R_3$ is 1,1,1-trichloroethoxycarbonyl, $R_4$ is H, $R_5$ is H, A is absent, Y is $CH_2O$, and Z is O;

a compound of Formula (I) wherein $R_1$ is ethyl, $R_2$ is H, $R_3$ is H, $R_4$ is H, $R_5$ is H, A is absent, Y is $CH_2O$, and Z is O;

a compound of Formula (I) wherein $R_1$ is ethyl, $R_2$ is H, $R_3$ is 2-methyl-but-2-enyl, $R_4$ is H, $R_5$ is H, A is absent, Y is $CH_2O$, and Z is O;

a compound of Formula (I) wherein $R_1$ is ethyl, $R_2$ is H, $R_3$ is thiophen-2-yl methyl, $R_4$ is H, $R_5$ is H, A is absent, Y is $CH_2O$, and Z is O;

a compound of Formula (I) wherein $R_1$ is ethyl, $R_2$ is H, $R_3$ is 2-methyl-allyl, $R_4$ is H, $R_5$ is H, A is absent, Y is $CH_2O$, and Z is O;

a compound of Formula (I) wherein $R_1$ is ethyl, $R_2$ is H, $R_3$ is cyclopropylmethyl, $R_4$ is H, $R_5$ is H, A is absent, Y is $CH_2O$, and Z is O;

a compound of Formula (I) wherein $R_1$ is ethyl, $R_2$ is H, $R_3$ is pyridin-2-yl methyl, $R_4$ is H, $R_5$ is H, A is absent, Y is $CH_2O$, and Z is O;

a compound of Formula (I) wherein $R_1$ is ethyl, $R_2$ is H, $R_3$ is 1-H-imidazol-4-yl methyl, $R_4$ is H, $R_5$ is H, A is absent, Y is $CH_2O$, and Z is O;

a compound of Formula (I) wherein $R_1$ is ethyl, $R_2$ is H, $R_3$ is 4-hydroxy-3-methoxyphenyl-methyl, $R_4$ is H, $R_5$ is H, A is absent, Y is $CH_2O$, and Z is O;

a compound of Formula (I) wherein $R_1$ is ethyl, $R_2$ is H, $R_3$ is allyl, $R_4$ is H, $R_5$ is H, A is absent, Y is $CH_2O$, and Z is O;

a compound of Formula (I) wherein $R_1$ is ethyl, $R_2$ is H, $R_3$ is phenethyl, $R_4$ is H, $R_5$ is H, A is absent, Y is $CH_2O$, and Z is O;

a compound of Formula (I) wherein $R_1$ is ethyl, $R_2$ is ethyl, $R_3$ is phenethyl, $R_4$ is H, $R_5$ is H, A is absent, Y is O, and Z is O;

a compound of Formula (I) wherein $R_1$ is ethyl, $R_2$ is ethyl, $R_3$ is methyl, $R_4$ is H, $R_5$ is H, A is $CH_2CH_2$, Y is O, and Z is O;

a compound of Formula (I) wherein $R_1$ is ethyl, $R_2$ is ethyl, $R_3$ is H, $R_4$ is H, $R_5$ is H, A is $CH_2CH_2$, Y is O, and Z is O;

a compound of Formula (I) wherein $R_1$ is ethyl, $R_2$ is ethyl, $R_3$ is furan-3-yl methyl, $R_4$ is H, $R_5$ is H, A is $CH_2CH_2$, Y is O, and Z is O;

a compound of Formula (I) wherein $R_1$ is ethyl, $R_2$ is H, $R_3$ is phenethyl, $R_4$ is H, $R_5$ is H, A is $CH_2CH_2$, Y is $CH_2O$, and Z is O;

a compound of Formula (I) wherein $R_1$ is ethyl, $R_2$ is ethyl, $R_3$ is phenethyl, $R_4$ is H, $R_5$ is H, A is $CH_2CH_2$, Y is O, and Z is O;

a compound of Formula (I) wherein $R_1$ is ethyl, $R_2$ is ethyl, $R_3$ is furan-3-yl methyl, $R_4$ is H, $R_5$ is H, A is absent, Y is O, and Z is O;

a compound of Formula (I) wherein $R_1$ is ethyl, $R_2$ is ethyl, $R_3$ is pyridin-2-yl methyl, $R_4$ is H, $R_5$ is H, A is absent, Y is O, and Z is O;

a compound of Formula (I) wherein $R_1$ is ethyl, $R_2$ is ethyl, $R_3$ is 2-hydroxyphenyl-methyl, $R_4$ is H, $R_5$ is H, A is absent, Y is O, and Z is O;

a compound of Formula (I) wherein $R_1$ is ethyl, $R_2$ is ethyl, $R_3$ is carbamimidoyl, $R_4$ is H, $R_5$ is H, A is absent, Y is O, and Z is O;

a compound of Formula (I) wherein $R_1$ is ethyl, $R_2$ is H, $R_3$ is H, $R_4$ is H, $R_5$ is H, A is absent, Y is O, and Z is O;

a compound of Formula (I) wherein $R_1$ is ethyl, $R_2$ is ethyl, $R_3$ is 1-prop-2-ynyl, $R_4$ is H, $R_5$ is H, A is absent, Y is O, and Z is O;

a compound of Formula (I) wherein $R_1$ is ethyl, $R_2$ is ethyl, $R_3$ is H, $R_4$ is methylcarbonylamino, $R_5$ is H, A is absent, Y is O, and Z is O;

a compound of Formula (I) wherein $R_1$ is ethyl, $R_2$ is ethyl, $R_3$ is hydroxy-ethyl, $R_4$ is H, $R_5$ is H, A is absent, Y is O, and Z is O;

a compound of Formula (I) wherein $R_1$ is ethyl, $R_2$ is ethyl, $R_3$ is phenyliminomethyl, $R_4$ is H, $R_5$ is H, A is absent, Y is O, and Z is O;

a compound of Formula (I) wherein $R_1$ is ethyl, $R_2$ is ethyl, $R_3$ is thioformyl, $R_4$ is H, $R_5$ is H, A is absent, Y is O, and Z is O;

a compound of Formula (I) wherein $R_1$ is ethyl, $R_2$ is ethyl, $R_3$ is allyl, $R_4$ is H, $R_5$ is H, A is $CH_2CH_2$, Y is O, and Z is O;

a compound of Formula (I) wherein $R_1$ is ethyl, $R_2$ is ethyl, $R_3$ is methoxyethyl, $R_4$ is H, $R_5$ is H, A is $CH_2CH_2$, Y is O, and Z is O;

a compound of Formula (I) wherein $R_1$ is ethyl, $R_2$ is ethyl, $R_3$ is methylthio-ethyl, $R_4$ is H, $R_5$ is H, A is $CH_2CH_2$, Y is O, and Z is O;

a compound of Formula (I) wherein $R_1$ is ethyl, $R_2$ is ethyl, $R_3$ is methyl, $R_4$ is methylcarbonylamino, $R_5$ is H, A is absent, Y is O, and Z is O;

a compound of Formula (I) wherein $R_1$ is ethyl, $R_2$ is ethyl, $R_3$ is H, $R_4$ is H, $R_5$ is H, A is absent, Y is O, and Z is O;

a compound of Formula (I) wherein $R_1$ is ethyl, $R_2$ is ethyl, $R_3$ is methyl, $R_4$ is H, $R_5$ is H, A is absent, Y is O, and Z is O;

a compound of Formula (I) wherein $R_1$ is ethyl, $R_2$ is ethyl, $R_3$ is pyridin-2-yl methyl, $R_4$ is H, $R_5$ is H, A is $CH_2CH_2$, Y is O, and Z is O;

a compound of Formula (I) wherein $R_1$ is ethyl, $R_2$ is ethyl, $R_3$ is hydroxyethyl, $R_4$ is H, $R_5$ is H, A is $CH_2CH_2$, Y is O, and Z is O;

a compound of Formula (I) wherein $R_1$ is ethyl, $R_2$ is ethyl, $R_3$ is 1-H-imidazol-4-yl methyl, $R_4$ is H, $R_5$ is H, A is $CH_2CH_2$, Y is O, and Z is O;

a compound of Formula (I) wherein $R_1$ is ethyl, $R_2$ is ethyl, $R_3$ is benzo[1,3]dioxol-5-ylmethyl, $R_4$ is H, $R_5$ is H, A is $CH_2CH_2$, Y is S, and Z is O;

a compound of Formula (I) wherein $R_1$ is ethyl, $R_2$ is ethyl, $R_3$ is H, $R_4$ is H, $R_5$ is H, A is $CH_2CH_2$, Y is S, and Z is O;

a compound of Formula (I) wherein $R_1$ is ethyl, $R_2$ is ethyl, $R_3$ is cyclopropylmethyl, $R_4$ is H, $R_5$ is H, A is $CH_2CH_2$, Y is S, and Z is O;

a compound of Formula (I) wherein $R_1$ is ethyl, $R_2$ is ethyl, $R_3$ is methylthio-propyl, $R_4$ is H, $R_5$ is H, A is $CH_2CH_2$, Y is S, and Z is O;

a compound of Formula (I) wherein $R_1$ is ethyl, $R_2$ is ethyl, $R_3$ is hydroxy-ethyl, $R_4$ is H, $R_5$ is H, A is $CH_2CH_2$, Y is S, and Z is O;

a compound of Formula (I) wherein $R_1$ is ethyl, $R_2$ is ethyl, $R_3$ is H, $R_4$ is H, $R_5$ is H, A is $CH_2CH_2$, Y is O, and Z is O;

a compound of Formula (I) wherein $R_1$ is ethyl, $R_2$ is ethyl, $R_3$ is H, $R_4$ is H, $R_5$ is H, A is $CH_2CH_2$, Y is O, and Z is O;

a compound of Formula (I) wherein $R_1$ is ethyl, $R_2$ is H, $R_3$ is H, $R_4$ is H, $R_5$ is H, A is $CH_2CH_2$, Y is O, and Z is O;

a compound of Formula (I) wherein $R_1$ is methyl, $R_2$ is methyl, $R_3$ is H, $R_4$ is H, $R_5$ is H, A is $CH_2CH_2$, Y is O, and Z is O;

a compound of Formula (I) wherein $R_1$ is isopropyl, $R_2$ is H, $R_3$ is H, $R_4$ is H, $R_5$ is H, A is $CH_2CH_2$, Y is O, and Z is O;

a compound of Formula (I) wherein $R_1$ is methyl, $R_2$ is isobutyl, $R_3$ is H, $R_4$ is H, $R_5$ is H, A is $CH_2CH_2$, Y is O, and Z is O;

a compound of Formula (I) wherein $R_1$ is n-propyl, $R_2$ is n-propyl, $R_3$ is H, $R_4$ is H, $R_5$ is H, A is $CH_2CH_2$, Y is O, and Z is O;

a compound of Formula (I) wherein $R_1$ is n-propyl, $R_2$ is H, $R_3$ is H, $R_4$ is H, $R_5$ is H, A is $CH_2CH_2$, Y is S, and Z is O;

a compound of Formula (I) wherein $R_1$ is methyl, $R_2$ is H, $R_3$ is H, $R_4$ is H, $R_5$ is H, A is $CH_2CH_2$, Y is O, and Z is O;

a compound of Formula (I) wherein $R_1$ is H, $R_2$ is H, $R_3$ is H, $R_4$ is H, $R_5$ is H, A is $CH_2CH_2$, Y is O, and Z is O;

a compound of Formula (I) wherein $R_1$ is ethyl, $R_2$ is ethyl, $R_3$ is H, $R_4$ is 6-methyl, $R_5$ is H, A is $CH_2CH_2$, Y is O, and Z is O;

a compound of Formula (I) wherein $R_1$ is ethyl, $R_2$ is ethyl, $R_3$ is H, $R_4$ is 7-methyl, $R_5$ is H, A is $CH_2CH_2$, Y is O, and Z is O;

a compound of Formula (I) wherein $R_1$ is ethyl, $R_2$ is ethyl, $R_3$ is H, $R_4$ is 5-methoxy, $R_5$ is H, A is $CH_2CH_2$, Y is O, and Z is O;

a compound of Formula (I) wherein $R_1$ is ethyl, $R_2$ is ethyl, $R_3$ is H, $R_4$ is 7-fluoro, $R_5$ is H, A is $CH_2CH_2$, Y is O, and Z is O;

a compound of Formula (I) wherein $R_1$ is ethyl, $R_2$ is ethyl, $R_3$ is H, $R_4$ is 6-methoxy, $R_5$ is H, A is $CH_2CH_2$, Y is O, and Z is O;

a compound of Formula (I) wherein $R_1$ is ethyl, $R_2$ is ethyl, $R_3$ is 1-H-imidazol-5-ylmethyl, $R_4$ is H, $R_5$ is H, A is $CH_2CH_2$, Y is O, and Z is O;

a compound of Formula (I) wherein $R_1$ is methyl, $R_2$ is n-butyl, $R_3$ is H, $R_4$ is H, $R_5$ is H, A is $CH_2CH_2$, Y is O, and Z is O;

a compound of Formula (I) wherein $R_1$ is ethyl, $R_2$ is ethyl, $R_3$ is 1-H-imidazol-4-ylmethyl, $R_4$ is H, $R_5$ is H, A is $CH_2CH_2$, Y is S, and Z is O;

a compound of Formula (I) wherein $R_1$ is ethyl, $R_2$ is ethyl, $R_3$ is H, $R_4$ is 6-hydroxy, $R_5$ is H, A is $CH_2CH_2$, Y is O, and Z is O;

a compound of Formula (I) wherein $R_1$ is ethyl, $R_2$ is ethyl, $R_3$ is H, $R_4$ is 7-methoxy, $R_5$ is H, A is $CH_2CH_2$, Y is O, and Z is O;

a compound of Formula (I) wherein $R_1$ is ethyl, $R_2$ is H, $R_3$ is trifluoromethylcarbonyl, $R_4$ is H, $R_5$ is H, A is $CH_2CH_2$, Y is S, and Z is O;

a compound of Formula (I) wherein $R_1$ is ethyl, $R_2$ is H, $R_3$ is H, $R_4$ is H, $R_5$ is H, A is $CH_2CH_2$, Y is S, and Z is O;

a compound of Formula (I) wherein $R_1$ is ethyl, $R_2$ is ethyl, $R_3$ is H, $R_4$ is 7-hydroxy, $R_5$ is H, A is $CH_2CH_2$, Y is O, and Z is O;

a compound of Formula (I) wherein $R_1$ is ethyl, $R_2$ is ethyl, $R_3$ is H, $R_4$ is 7-bromo, $R_5$ is H, A is $CH_2CH_2$, Y is O, and Z is O;

a compound of Formula (I) wherein $R_1$ is ethyl, $R_2$ is ethyl, $R_3$ is H, $R_4$ is 7-phenyl, $R_5$ is H, A is $CH_2CH_2$, Y is O, and Z is O;

a compound of Formula (I) wherein $R_1$ is ethyl, $R_2$ is ethyl, $R_3$ is H, $R_4$ is 7-pyridin-4-yl, $R_5$ is H, A is $CH_2CH_2$, Y is O, and Z is O;

a compound of Formula (I) wherein $R_1$ is ethyl, $R_2$ is ethyl, $R_3$ is H, $R_4$ is 7-furan-3-yl, $R_5$ is H, A is $CH_2CH_2$, Y is O, and Z is O;

a compound of Formula (I) wherein $R_1$ is ethyl, $R_2$ is ethyl, $R_3$ is H, $R_4$ is 7-benzothiophen-2-yl, $R_5$ is H, A is $CH_2CH_2$, Y is O, and Z is O;

a compound of Formula (I) wherein $R_1$ is ethyl, $R_2$ is ethyl, $R_3$ is H, $R_4$ is 7-(N-t-butoxycarbonyl)pyrrol-2-yl, $R_5$ is H, A is $CH_2CH_2$, Y is O, and Z is O;

a compound of Formula (I) wherein $R_1$ is ethyl, $R_2$ is ethyl, $R_3$ is H, $R_4$ is 7-pyridin-3-yl, $R_5$ is H, A is $CH_2CH_2$, Y is O, and Z is O;

a compound of Formula (I) wherein $R_1$ is ethyl, $R_2$ is ethyl, $R_3$ is H, $R_4$ is 7-thiophen-3-yl, $R_5$ is H, A is $CH_2CH_2$, Y is O, and Z is O;

a compound of Formula (I) wherein $R_1$ is ethyl, $R_2$ is ethyl, $R_3$ is H, $R_4$ is 7-(3,5-dimethyl)isoxazol-4-yl, $R_5$ is H, A is $CH_2CH_2$, Y is O, and Z is O;

a compound of Formula (I) wherein $R_1$ is methyl, $R_2$ is isopropyl, $R_3$ is H, $R_4$ is H, $R_5$ is H, A is $CH_2CH_2$, Y is O, and Z is O;

a compound of Formula (I) wherein $R_1$ is ethyl, $R_2$ is ethyl, $R_3$ is H, $R_4$ is 7-pyrrol-2-yl, $R_5$ is H, A is $CH_2CH_2$, Y is O, and Z is O;

a compound of Formula (I) wherein $R_1$ is ethyl, $R_2$ is ethyl, $R_3$ is H, $R_4$ is 5-bromo, $R_5$ is H, A is $CH_2CH_2$, Y is O, and Z is O;

a compound of Formula (I) wherein $R_1$ is ethyl, $R_2$ is ethyl, $R_3$ is H, $R_4$ is 5-phenyl, $R_5$ is H, A is $CH_2CH_2$, Y is O, and Z is O;

a compound of Formula (I) wherein $R_1$ is ethyl, $R_2$ is ethyl, $R_3$ is H, $R_4$ is 5-pyridin-4-yl, $R_5$ is H, A is $CH_2CH_2$, Y is O, and Z is O;

a compound of Formula (I) wherein $R_1$ is ethyl, $R_2$ is ethyl, $R_3$ is H, $R_4$ is 5-furan-3-yl, $R_5$ is H, A is $CH_2CH_2$, Y is O, and Z is O;

a compound of Formula (I) wherein $R_1$ is ethyl, $R_2$ is ethyl, $R_3$ is H, $R_4$ is 5-quinolin-3-yl, $R_5$ is H, A is $CH_2CH_2$, Y is O, and Z is O;

a compound of Formula (I) wherein $R_1$ is ethyl, $R_2$ is ethyl, $R_3$ is H, $R_4$ is 5-thiophen-3-yl, $R_5$ is H, A is $CH_2CH_2$, Y is O, and Z is O;

a compound of Formula (I) wherein $R_1$ is ethyl, $R_2$ is ethyl, $R_3$ is H, $R_4$ is 5-hydroxy, $R_5$ is H, A is $CH_2CH_2$, Y is O, and Z is O;

a compound of Formula (I) wherein $R_1$ is ethyl, $R_2$ is ethyl, $R_3$ is H, $R_4$ is 5-pyridin-3-yl, $R_5$ is H, A is $CH_2CH_2$, Y is O, and Z is O; and a compound of Formula (I) wherein $R_1$ is ethyl, $R_2$ is ethyl, $R_3$ is H, $R_4$ is 5-fluoro, $R_5$ is H, A is $CH_2CH_2$, Y is O, and Z is O.

Another embodiment of the present invention is directed to compositions comprising a compound selected from the group consisting of:

a compound of Formula (I) wherein $R_1$ is ethyl, $R_2$ is H, $R_3$ is H, $R_4$ is H, $R_5$ is H, A is absent, Y is $CH_2O$, and Z is O;

a compound of Formula (I) wherein $R_1$ is ethyl, $R_2$ is H, $R_3$ is 2-methyl-but-2-enyl, $R_4$ is H, $R_5$ is H, A is absent, Y is $CH_2O$, and Z is O;

a compound of Formula (I) wherein $R_1$ is ethyl, $R_2$ is H, $R_3$ is thiophen-2-yl methyl, $R_4$ is H, $R_5$ is H, A is absent, Y is $CH_2O$, and Z is O;

a compound of Formula (I) wherein $R_1$ is ethyl, $R_2$ is H, $R_3$ is 2-methyl-allyl, $R_4$ is H, $R_5$ is H, A is absent, Y is $CH_2O$, and Z is O;

a compound of Formula (I) wherein $R_1$ is ethyl, $R_2$ is H, $R_3$ is pyridin-2-yl methyl, $R_4$ is H, $R_5$ is H, A is absent, Y is $CH_2O$, and Z is O;

a compound of Formula (I) wherein $R_1$ is ethyl, $R_2$ is H, $R_3$ is 1-H-imidazol-4-yl methyl, $R_4$ is H, $R_5$ is H, A is absent, Y is $CH_2O$, and Z is O;

a compound of Formula (I) wherein $R_1$ is ethyl, $R_2$ is H, $R_3$ is allyl, $R_4$ is H, $R_5$ is H, A is absent, Y is $CH_2O$, and Z is O;

a compound of Formula (I) wherein $R_1$ is ethyl, $R_2$ is H, $R_3$ is phenethyl, $R_4$ is H, $R_5$ is H, A is $CH_2CH_2$, Y is O, and Z is O;

a compound of Formula (I) wherein $R_1$ is ethyl, $R_2$ is H, $R_3$ is H, $R_4$ is H, $R_5$ is H, A is absent, Y is O, and Z is O;

a compound of Formula (I) wherein $R_1$ is ethyl, $R_2$ is ethyl, $R_3$ is H, $R_4$ is H, $R_5$ is H, A is absent, Y is O, and Z is O;

a compound of Formula (I) wherein $R_1$ is ethyl, $R_2$ is ethyl, $R_3$ is 1-H-imidazol-5-yl methyl, $R_4$ is H, $R_5$ is H, A is $CH_2CH_2$, Y is O, and Z is O;

a compound of Formula (I) wherein $R_1$ is ethyl, $R_2$ is ethyl, $R_3$ is H, $R_4$ is 5-hydroxy, $R_5$ is H, A is $CH_2CH_2$, Y is O, and Z is O;

a compound of Formula (I) wherein $R_1$ is ethyl, $R_2$ is ethyl, $R_3$ is 1-H-imidazol-4-ylmethyl, $R_4$ is H, $R_5$ is H, A is $CH_2CH_2$, Y is S, and Z is O;

a compound of Formula (I) wherein $R_1$ is ethyl, $R_2$ is ethyl, $R_3$ is H, $R_4$ is 5-methoxy, $R_5$ is H, A is $CH_2CH_2$, Y is O, and Z is O;

a compound of Formula (I) wherein $R_1$ is ethyl, $R_2$ is ethyl, $R_3$ is H, $R_4$ is 5-pyridin-4-yl, $R_5$ is H, A is $CH_2CH_2$, Y is O, and Z is O;

a compound of Formula (I) wherein $R_1$ is ethyl, $R_2$ is ethyl, $R_3$ is H, $R_4$ is 5-furan-3-yl, $R_5$ is H, A is $CH_2CH_2$, Y is O, and Z is O;

a compound of Formula (I) wherein $R_1$ is ethyl, $R_2$ is ethyl, $R_3$ is H, $R_4$ is 6-hydroxy, $R_5$ is H, A is $CH_2CH_2$, Y is O, and Z is O;

a compound of Formula (I) wherein $R_1$ is methyl, $R_2$ is isopropyl, $R_3$ is H, $R_4$ is H, $R_5$ is H, A is $CH_2CH_2$, Y is O, and Z is O;

a compound of Formula (I) wherein $R_1$ is ethyl, $R_2$ is ethyl, $R_3$ is H, $R_4$ is 5-bromo, $R_5$ is H, A is $CH_2CH_2$, Y is O, and Z is O;

a compound of Formula (I) wherein $R_1$ is ethyl, $R_2$ is ethyl, $R_3$ is H, $R_4$ is 6-methoxy, $R_5$ is H, A is $CH_2CH_2$, Y is O, and Z is O;

a compound of Formula (I) wherein $R_1$ is ethyl, $R_2$ is ethyl, $R_3$ is H, $R_4$ is 6-methyl, $R_5$ is H, A is $CH_2CH_2$, Y is O, and Z is O;

a compound of Formula (I) wherein $R_1$ is ethyl, $R_2$ is ethyl, $R_3$ is H, $R_4$ is H, $R_5$ is H, A is $CH_2CH_2$, Y is S, and Z is O;

a compound of Formula (I) wherein $R_1$ is n-propyl, $R_2$ is n-propyl, $R_3$ is H, $R_4$ is H, $R_5$ is H, A is $CH_2CH_2$, Y is O, and Z is O;

a compound of Formula (I) wherein $R_1$ is ethyl, $R_2$ is ethyl, $R_3$ is H, $R_4$ is 7-fluoro, $R_5$ is H, A is $CH_2CH_2$, Y is O, and Z is O;

a compound of Formula (I) wherein $R_1$ is ethyl, $R_2$ is ethyl, $R_3$ is H, $R_4$ is 5-pyridin-3-yl, $R_5$ is H, A is $CH_2CH_2$, Y is O, and Z is O;

a compound of Formula (I) wherein $R_1$ is methyl, $R_2$ is isobutyl, $R_3$ is H, $R_4$ is H, $R_5$ is H, A is $CH_2CH_2$, Y is O, and Z is O;

a compound of Formula (I) wherein $R_1$ is methyl, $R_2$ is n-butyl, $R_3$ is H, $R_4$ is H, $R_5$ is H, A is $CH_2CH_2$, Y is O, and Z is O;

a compound of Formula (I) wherein $R_1$ is ethyl, $R_2$ is ethyl, $R_3$ is H, $R_4$ is 5-quinolin-3-yl, $R_5$ is H, A is $CH_2CH_2$, Y is O, and Z is O;

a compound of Formula (I) wherein $R_1$ is ethyl, $R_2$ is ethyl, $R_3$ is H, $R_4$ is 5-thiophen-3-yl, $R_5$ is H, A is $CH_2CH_2$, Y is O, and Z is O; and a compound of Formula (I) wherein $R_1$ is ethyl, $R_2$ is ethyl, $R_3$ is H, $R_4$ is 5-phenyl, $R_5$ is H, A is $CH_2CH_2$, Y is O, and Z is O.

Another embodiment of the present invention is a composition comprising the dextrorotatory enantiomer of a compound of formula (I) wherein $R_1$ is ethyl, $R_2$ is ethyl, $R_3$ is H, $R_4$ is H, $R_5$ is H, A is $CH_2CH_2$, Y is O, and Z is O; wherein said composition is substantially free from the levorotatory isomer of said compound. In the present context, substantially free means less than 25%, preferably less than 10%, more preferably less than 5%, even more preferably less than 2% and even more preferably less than 1% of the levorotatory isomer calculated as.

$$\% \text{ levorotatory} = \frac{(\text{mass levorotatory})}{(\text{mass dextrorotatory}) + (\text{mass levorotatory})} \times 100$$

Another embodiment of the present invention is a composition comprising the levorotatory enantiomer of a compound of formula (I) wherein $R_1$ is ethyl, $R_2$ is ethyl, $R_3$ is H, $R_4$ is H, $R_5$ is H, A is $CH_2CH_2$, Y is O, and Z is O; wherein said composition is substantially free from the dextrorotatory isomer of said compound. In the present context, substantially free from means less than 25%, preferably less than 10%, more preferably less than 5%, even more preferably less than 2% and even more preferably less than 1% of the dextrorotatory isomer calculated as $$\% \text{ dextrorotatory} = \frac{(\text{mass dextrorotatory})}{(\text{mass dextrorotatory}) + (\text{mass levorotatory})} \times 100$$

The compounds of the present invention may also be present in the form of pharmaceutically acceptable salts. For use in medicine, the salts of the compounds of this invention refer to non-toxic "pharmaceutically acceptable salts" (*Ref: International J. Pharm.*, 1986, 33, 201-217; *J. Pharm. Sci.*, 1997 (January), 66, 1, 1). Other salts well known to those in the art may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The present invention includes within its scope prodrugs of the compounds of this invention. In general, such prodrugs will be functional derivatives of the compounds that are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

Even though the compounds of the present invention (including their pharmaceutically, acceptable salts and pharmaceutically acceptable solvates) can be administered alone, they will generally be administered in admixture with a pharmaceutical carrier, excipient or diluent selected with regard to the intended route of administration and standard pharmaceutical or veterinary practice. Thus, the present invention is directed to pharmaceutical and veterinary compositions comprising compounds of Formula (I) and one or more pharmaceutically acceptable carriers, excipients or diluents.

By way of example, in the pharmaceutical and veterinary compositions of the present invention, the compounds of the present invention may be admixed with any suitable binder(s), lubricant(s), suspending agent(s), coating agent(s), and/or solubilising agent(s).

Tablets or capsules of the compounds may be administered singly or two or more at a time, as appropriate. It is also possible to administer the compounds in sustained release formulations.

Alternatively, the compounds of the general Formula (I) can be administered by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin. They can also be incorporated, at a concentration of between 1 and 10% by weight, into an ointment consisting of a white wax or white soft paraffin base together with such stabilizers and preservatives as may be required.

For some applications, preferably the compositions are administered orally in the form of tablets containing excipients such as starch or lactose, or in capsules or ovules either alone or in admixture with excipients, or in the form of elixirs, solutions or suspensions containing flavoring or coloring agents.

The compositions (as well as the compounds alone) can also be injected perenterally, for example intracavernosally, intravenously, intramuscularly or subcutaneously. In this case, the compositions will comprise a suitable carrier or diluent.

For parenteral administration, the compositions are best used in the form of a sterile aqueous solution which may contain other substances, for example enough salts or monosaccharides to make the solution isotonic with blood.

For buccal or sublingual administration the compositions may be administered in the form of tablets or lozenges which can be formulated in a conventional manner.

By way of further example, pharmaceutical and veterinary compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate the major site of absorption. For parenteral administration, the carrier will usually consist of sterile water and other ingredients may be added to increase solubility or preservation. Injectable suspensions or solutions may also be prepared utilizing aqueous carriers along with appropriate additives.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those skilled in that art. To be administered in the form of a transdermal delivery system, the dosage administration will, of course, be continuous rather than intermittent throughout the dosage regimen.

It is also apparent to one skilled in the art that the therapeutically effective dose for active compounds of the invention or a pharmaceutical composition thereof will vary according to the desired effect. Therefore, optimal dosages to be administered may be readily determined and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

Compounds of this invention may be administered in any of the foregoing compositions and dosage regimens or by means of those compositions and dosage regimens established in the art whenever use of the compounds of the invention as analgesics or anti-pyretics is required for a subject in need thereof.

The invention also provides a pharmaceutical or veterinary pack or kit comprising one or more containers filled with one or more of the ingredients of the pharmaceutical and veterinary compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The compounds of the present invention may be used to treat mild to moderately severe pain in warm-blooded animals such as humans by administration of an analgesically effective dose. The dosage range would be from about 0.01 mg to about 15,000 mg, in particular from about 0.1 mg to about 3500 mg or, more particularly from about 0.1 mg to about 1000 mg of active ingredient in a regimen of about 1 to 4 times per day for an average (70 kg) human; although, it is apparent to one skilled in the art that the therapeutically effective amount for active compounds of the invention will vary as will the types of pain being treated.

For oral administration, a pharmaceutical composition is preferably provided in the form of tablets containing, 0.01, 10.0, 50.0, 100, 150, 200, 250 and 500 milligrams of the active ingredient for the symptomatic adjustment of the dosage to the subject to be treated.

Examples of pain intended to be within the scope of the present invention include, but are not limited to, inflammatory pain, centrally mediated pain, peripherally mediated pain, structural or soft tissue injury related pain, progressive disease related pain, neuropathic pain and acute pain such as caused by acute injury, trauma or surgery and chronic pain such as headache and that caused by neuropathic conditions, post-stroke conditions and migraine.

Compounds of the present invention are also useful as immunosuppressants, antiinflammatory agents, agents for the treatment and prevention of neurological and psychiatric conditions, for instance, depression and Parkinson's disease, medicaments for drug and alcohol abuse, agents for treating gastritis and diarrhea, cardiovascular agents and agents for the treatment of respiratory diseases.

The compounds of the present invention are also useful in treating pain caused by osteoarthritis, rheumatoid arthritis, fibromyalgia, migraine, headache, toothache, burn, sunburn, snake bite (in particular, venomous snake bite), spider bite, insect sting, neurogenic bladder, benign prostatic hypertrophy, interstitial cystitis, rhinitis, contact dermatitis/hypersensitivity, itch, eczema, pharyngitis, mucositis, enteritis, cellulites, causalgia, sciatic neuritis, mandibular joint neuralgia, peripheral neuritis, polyneuritis, stump pain, phantom limb pain, post-operative ileus, cholecystitis, postmastectomy pain syndrome, oral neuropathic pain, Charcot's pain, reflex sympathetic dystrophy, Guillain-Barre syndrome, meralgia paresthetica, burning-mouth syndrome, post-herpetic neuralgia, trigeminal neuralgia, cluster headache, migraine headache, peripheral neuropathy, bilateral peripheral neuropathy, diabetic neuropathy, postherpetic neuralgia, trigeminal neuralgia, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, red neuralgia, Sluder's neuralgia, splenopalatine neuralgia, supraorbital neuralgia, vidian neuralgia, sinus headache, tension headache, labor, childbirth, menstrual cramps, and cancer.

In regard to the use of the present compounds in treatment of the diseases or conditions such as those listed above, a therapeutically effective dose can be determined by persons skilled in the art by the use of established animal models. Such a dose would likely fall in the range of from about 0.01 mg to about 15,000 mg of active ingredient administered 1 to 4 times per day for an average (70 kg) human.

General Synthetic Methods

Representative compounds of the present invention can be synthesized in accordance with the general synthetic methods described below and are illustrated in the schemes that follow. Since the schemes are an illustration, the invention should not be construed as being limited by the chemical reactions and conditions expressed. The preparation of the various starting materials used in the schemes is well within the skill of persons versed in the art.

The preparation of compounds of this invention is illustrated in Schemes 1 and 2. Both schemes proceed with the same overall strategy. In stage 1, an intermediate 1 is prepared with two benzene rings connected by a linker —Y—. The linker —Y— should be of the form —$(CH_2)_n$—X— where X may be oxygen or sulfur and n may be zero or one. One benzene ring bears a group, Q, which is a group readily transformable to a carboxylic acid amide. Examples of such Q groups are fluoro, bromo, iodo or trifluoromethanesulfonyloxy. One benzene ring must bear a carboxylic acid ortho to the linker —Y—. The atom X may be attached either to the benzene ring bearing the Q group or the benzene ring lacking the Q group. Schemes 1 and 2 differ in that in scheme 1, the carboxylic acid is on the benzene ring bearing the Q group (1A and 1B) while in scheme 2 the carboxylic acid function is on the benzene ring which does not bear the group Q (1C, D and E).

Scheme 1

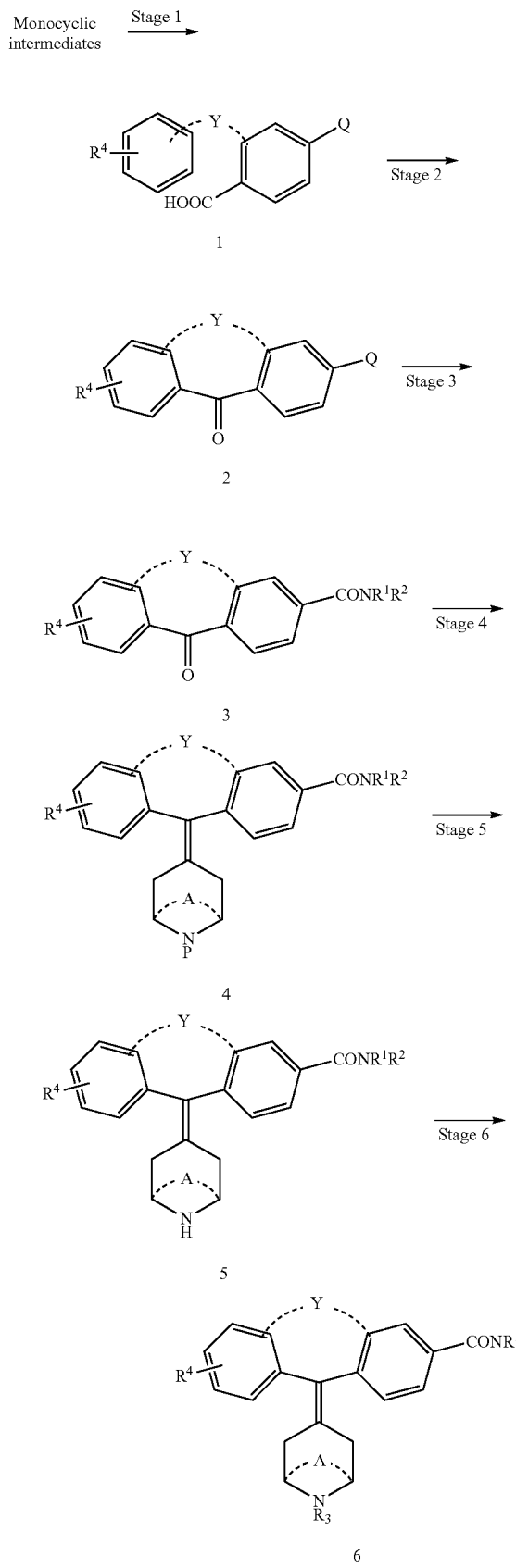

Scheme 2

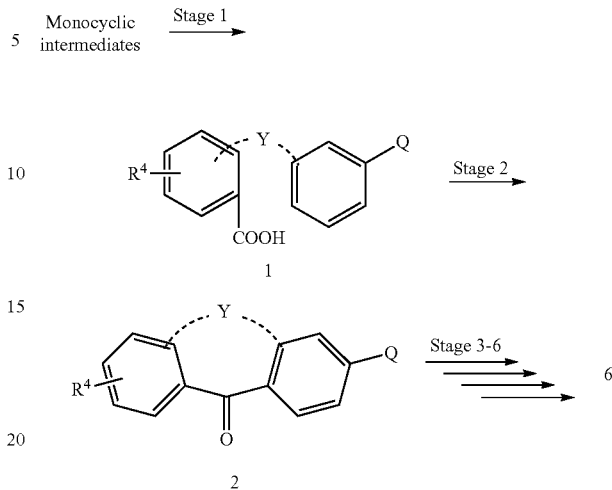

In stage 1 the linker —Y— is constructed between two monocyclic intermediates. For Scheme 1, Stage 1 the bridge may be constructed by nucleophilic aromatic displacement of fluoride from intermediate int 2 (where Q' is an electron withdrawing group, readily convertible to a carboxylic acid, for instance cyano or carbalkoxy) by a phenoxide, thiophenoxide, benzyloxide or thiobenzyloxide, int 1. The 1A compounds are then obtained by hydrolysis with an alkali metal hydroxide. For construction of the bridge of compounds of type 1B, a benzyl halide intermediate compound (int 5) is prepared by NBS bromination of the corresponding toluene (int 4). Reaction of int 5 with a phenoxide or thiophenoxide leads to int 6. The 1B compound may be obtained by alkali metal hydroxide hydrolysis of int 6.

Scheme 1, Stage 1

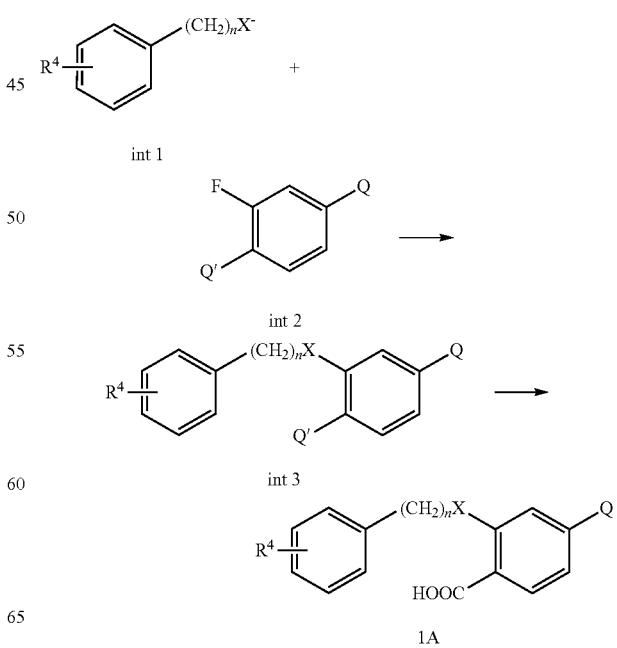

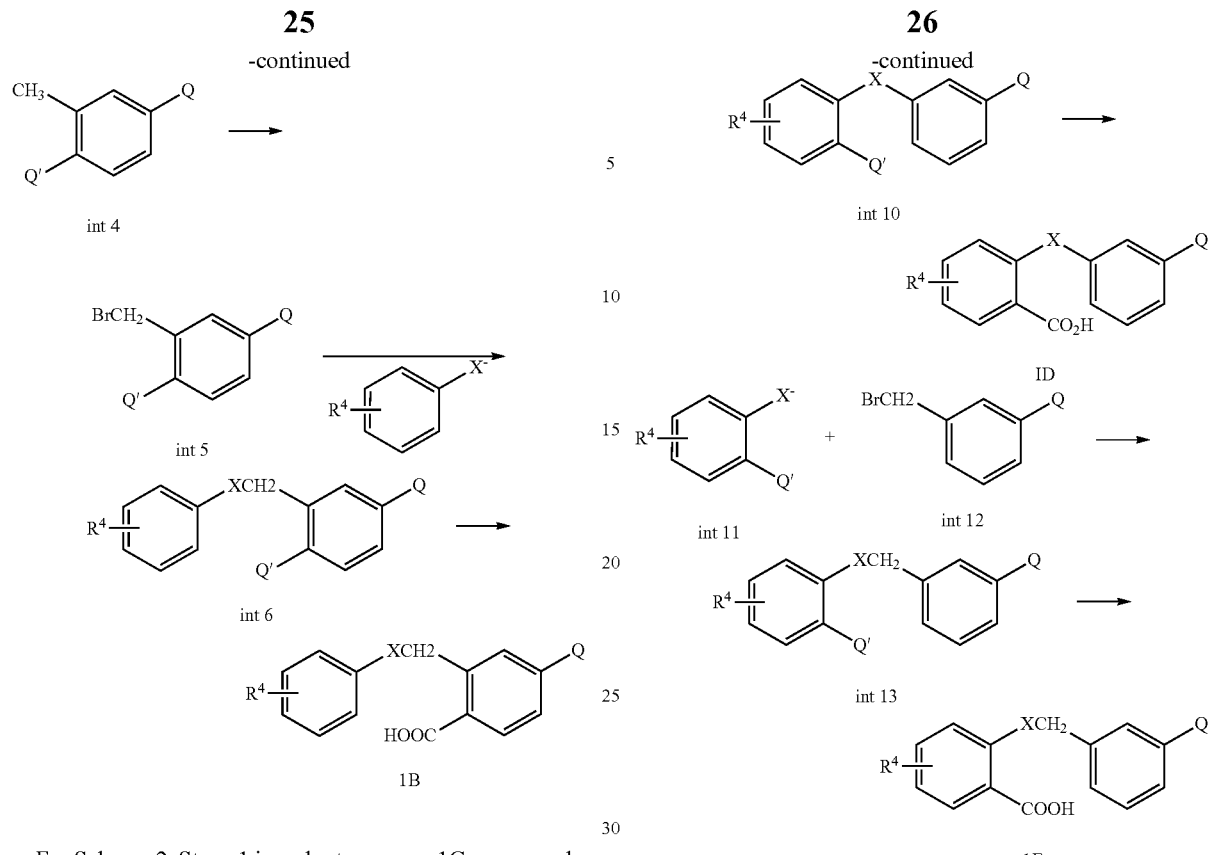

For Scheme 2, Stage 1 in order to prepare 1C compounds, a phthalide (int 7) may be caused to react with a phenoxide or thiophenoxide (int 8). For preparation of 1D compounds, the bridge may be constructed by nucleophilic aromatic displacement of fluoride from intermediate int 9 by phenoxides or thiophenoxides (int 8). The 1D compounds are then obtained by hydrolysis of int 10 with an alkali metal hydroxide. For construction of the bridge of compounds of type 1E, reaction of a benzyl bromide intermediate compound (int 12) with a phenoxide or thiophenoxide (int 11) leads to int 13. The 1E compound may then be obtained by hydrolysis of int 13 with an alkali metal hydroxide.

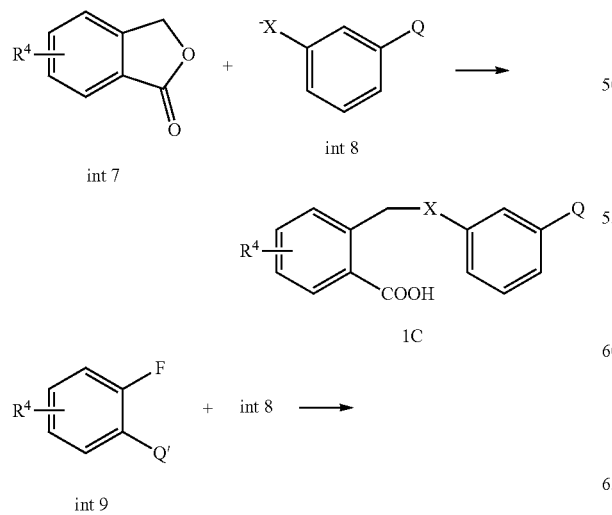

Following Stage 1, the schemes merge. In Stage 2 compounds 1 are converted by cycloacylation to ketones 2, using, for instance, $BF_3 \cdot Et_2O$-trifluoroacetic acid or polyphosphoric acid. Alternatively the cyclization may be effected by converting acid 1 to an acid chloride, for instance with thionyl chloride, followed by Friedel-Crafts ring closure in the presence of a Lewis acid, such as aluminum chloride.

In addition, Stages 1 and 2 may be performed in reverse to give compounds 2 that are ready to enter Stage 3. For instance, cycloacylation between a methyl ether (int 14) and an appropriately substituted acid chloride provides the ketone (int 16) which has been simultaneously demethylated under the Friedel-Crafts reaction conditions. Subsequent formation of the bridge —Y— via a nucleophilic aromatic displacement gives compounds 2 ready to enter Stage 3.

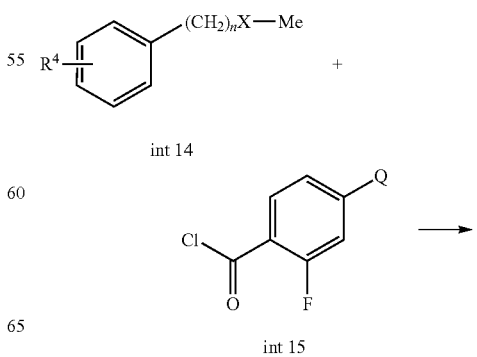

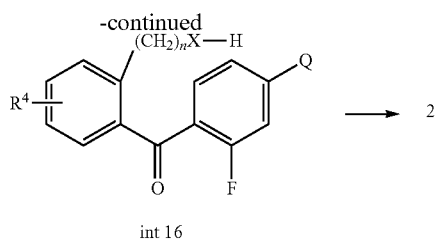

In stage 3, the Q function of compounds 2 is converted into carboxylic acid amide group to give compounds of formula 3. This may be accomplished by first conversion to an ester by alkoxycarbonylation, for instance, with carbon monoxide, an aliphatic alcohol, a trialkanyl amine and a palladium catalyst such as bis(triphenylphosphine) palladium(II)dichloride. The ester may be hydrolyzed to an acid and finally converted to a primary, secondary or tertiary amide by a coupling reaction with ammonia, a primary amine, or a secondary amine. The conversion of acid to amide may be carried out by first conversion to an acid chloride, for instance, using thionyl chloride, followed by Schotten-Baumann reaction using ammonia or an amine and alkali metal hydroxide. Alternatively, the ester may be converted directly to the amide by the action of a dimethylaluminum amide. Instead of proceeding to compounds 3 via an ester, one may effect the transformation of the group Q into a carboxylic acid amide by way of a nitrile. Synthesis of the nitrile may be accomplished by treatment of the compounds 2 with $Zn(CN)_2$ and a palladium catalyst such as $(Ph_3P)_4Pd$ or by treatment of the compounds 2 with CuCN at elevated temperature. The nitrile is hydrolyzed using an alkali metal hydroxide yielding the same acid as derived from the ester.

To perform stage 4, a 4-piperidinylidene or 8-tropanylidene function is attached to the tricyclic system, replacing the ketone to give compounds of type 4 (in the piperidinylidene case the function -A- does not exist while in the tropanylidene case it represents —$(CH_2)_2$—). This operation may be carried out by McMurray condensation of ketones 3 with 4-piperidinones or 8-tropinones brought about by a lower valent titanium reagent such as the reagent obtained from addition of titanium tetrachloride to zinc dust. Alternatively, a 4-piperidinyl magnesium halide or 8-tropanylidenyl-magnesium halide may be added to ketone to afford carbinols. Dehydration of such carbinols with acidic reagents such as formic acid, sulfuric acid or trifluoroacetic acid gives rise to compounds of type 4.

If desired, the operation of stages 3 and 4 may be carried out in reverse order.

As illustrated in Schemes 1 and 2, the nitrogen atoms of compounds 4 bear a group P. This group may be an alkanyl, alkenyl or aralkanyl in which case they are the therapeutically useful products of this invention. The group P may also be alkoxycarbonyl or aralkoxycarbonyl. The latter groupings can be converted to secondary amines 5 as illustrated for Stage 5. These transformations may be carried out using certain acidic reagents such as hydrogen bromide or trimethylsilyl iodide. Compounds of type 4 bearing readily cleavable groups such as methyl, allyl or benzyl may be transformed into the aforementioned alkoxycarbonyl derivatives by treatment with alkanylchloro-formates such as ethyl chloroformate or 1-choroethyl chloroformate and thus serve as sources of compounds 5.

Finally the secondary amines 5 may be converted to any desired end product of the invention 6 as shown in Stage 6. These transformations may be carried out by reductive alkylation using a carbonyl compound and a reducing agent such as sodium borohydride, sodium cyanoborohydride or sodium triacetoxyborohydride. They may also be carried out by alkyation using a alkanyl, alkenyl or arakyl halide and an organic or inorganic base.

Desired end products of the present invention may include chemical modifications at $R_4$. Such transformations may include the dealkylation of lower alkyl ethers to give the corresponding alcohols using reagents such as boron trihalides. Compounds where $R_4$ is a halogen atom may participate in transition metal-mediated coupling reactions such as Suzuki, Stille or Negishi chemistry.

The compounds wherein the bridge -A- is —$(CH_2)_2$— are chiral. They may be separated into their enantiomers by chromatography on a chiral stationary phase following Stages 4, 5, or 6. Alternatively, the basic compounds of types 4, 5, and 6 may be converted to diastereomeric salts by mixture with a chiral acid and resolved into their enantiomers by fractional crystallization.

It is generally preferred that the respective product of each process step be separated from other components of the reaction mixture and subjected to purification before its use as a starting material in a subsequent step. Separation techniques typically include evaporation, extraction, precipitation and filtration. Purification techniques typically include column chromatography (Still, W. C. et. al., J. Org. Chem. 1978, 43, 2921), thin-layer chromatography, crystallization and distillation. The structures of the final products, intermediates and starting materials are confirmed by spectroscopic, spectrometric and analytical methods including nuclear magnetic resonance (NMR), mass spectrometry (MS) and liquid chromatography (HPLC). In the descriptions for the preparation of compounds of this invention, ethyl ether, tetrahydrofuran and dioxane are common examples of an ethereal solvent; benzene, toluene, hexanes and cyclohexane are typical hydrocarbon solvents and dichloromethane and dichloroethane are representative halogenhydrocarbon solvents. In those cases where the product is isolated as the acid addition salt the free base may be obtained by techniques known to those skilled in the art. In those cases in which the product is isolated as an acid addition salt, the salt may contain one or more equivalents of the acid.

Enantiomers of the compounds of the present invention may be separated using chiral HPLC.

Representative compounds of the present invention can be synthesized in accordance with the general synthetic methods described above and are illustrated more particularly in the schemes that follow. Since the schemes are illustrations, the invention should not be construed as being limited by the chemical reactions and conditions expressed. The preparation of the various starting materials used in the schemes is well within the skill of persons versed in the art.

EXAMPLES

Example A

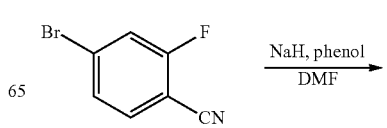

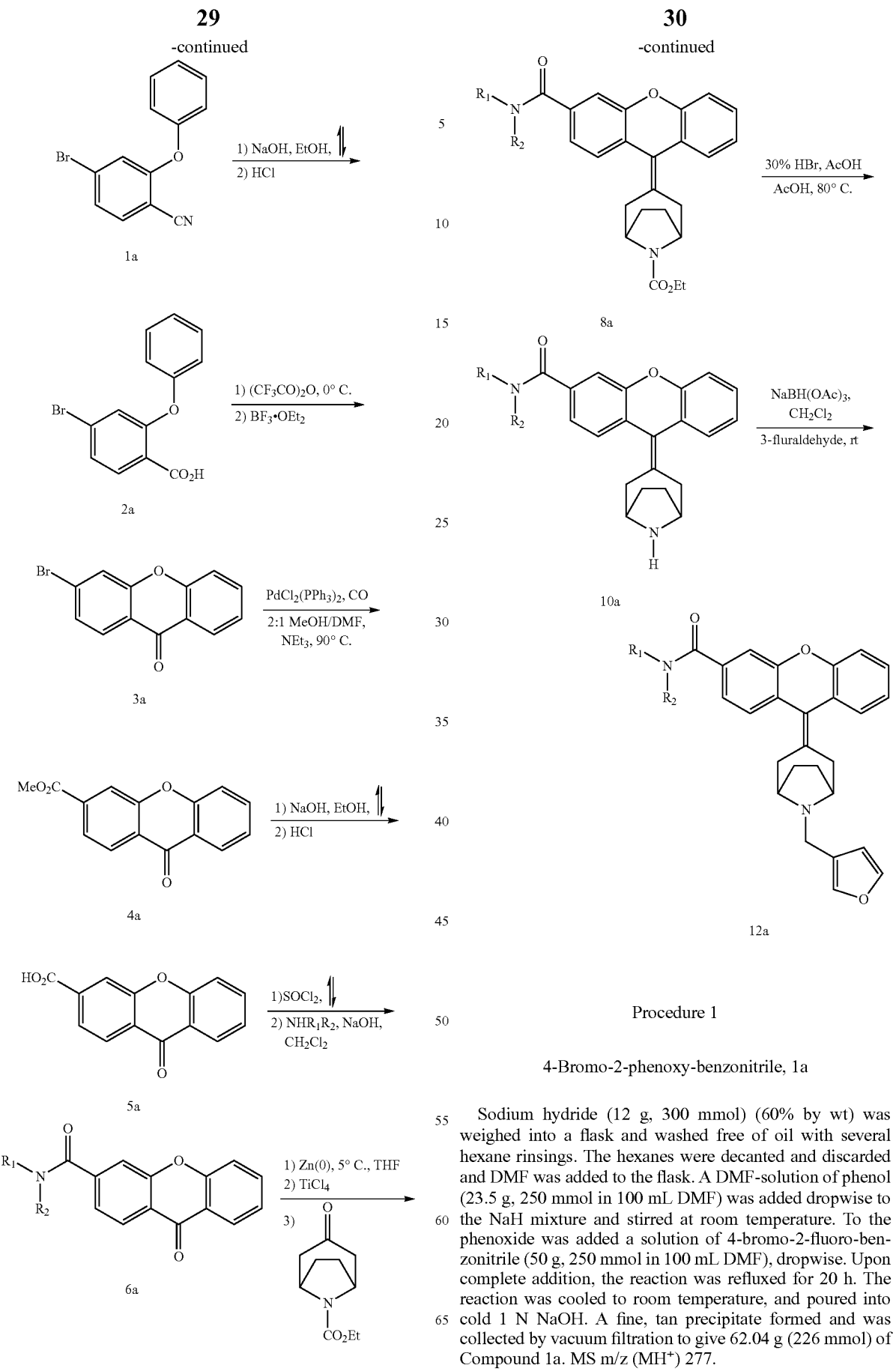

Procedure 1

4-Bromo-2-phenoxy-benzonitrile, 1a

Sodium hydride (12 g, 300 mmol) (60% by wt) was weighed into a flask and washed free of oil with several hexane rinsings. The hexanes were decanted and discarded and DMF was added to the flask. A DMF-solution of phenol (23.5 g, 250 mmol in 100 mL DMF) was added dropwise to the NaH mixture and stirred at room temperature. To the phenoxide was added a solution of 4-bromo-2-fluoro-benzonitrile (50 g, 250 mmol in 100 mL DMF), dropwise. Upon complete addition, the reaction was refluxed for 20 h. The reaction was cooled to room temperature, and poured into cold 1 N NaOH. A fine, tan precipitate formed and was collected by vacuum filtration to give 62.04 g (226 mmol) of Compound 1a. MS m/z (MH$^+$) 277.

Procedure 2

4-Bromo-2-phenoxy-benzoic acid, 2a

4-Bromo-2-phenoxy-benzonitrile (35.3 g, 129 mmol) was added to 130 mL EtOH, followed by the addition of 340 mL of 20% NaOH (aq). The reaction was heated to reflux for 20 h. The mixture was cooled to room temperature and poured into 6 N HCl to form a precipitate. The solid was collected by vacuum filtration and dissolved in 3:1 THF-ethyl ether and washed with brine. The organic phase was dried over magnesium sulfate, and concentrated. The solids were dried in a vacuum oven at 60° C. overnight to give 35.1 g (128 mmol) of the desired product. MS m/z (MH$^+$) 292.

Procedure 3

3-Bromo-xanthen-9-one, 3a

To a suspension of 4-bromo-2-phenoxy-benzoic acid (35.1 g, 120 mmol) in $CH_2Cl_2$ (350 mL) at 0° C. was added trifluoroacetic anhydride (20.3 mL, 144 mmol), dropwise, and the reaction was stirred for 15 min. At that time, boron trifluoride diethyl etherate (1.46 mL, 12.0 mmol) was added, dropwise. The reaction became homogeneous upon stirring for 1 h at room temperature. Upon completion, the reaction was poured into 1 N NaOH, and the organic phase was dried over magnesium sulfate, filtered, and concentrated to give Compound 3a (32.14 g, 116 mmol). MS m/z (MH$^+$) 275.

Procedure 4

9-Oxo-9H-xanthene-3-carboxylic acid methyl ester, 4a

A sample of Compound 3a (20 g, 72.2 mmol) was dissolved in a 2:1 MeOH/DMF solution (600 mL). To this solution was added triethylamine (40 mL, 290 mmol) and the solution was degassed with Argon. To this was added dichlorobis(triphenylphosphine) palladium (II) (2.0 g, 2.85 mmol), and the reaction was transferred to a bomb and charged with 150 psi of CO (g). The reaction was stirred at 90° C. for 24 h. Upon completion, the reaction was cooled to 40° C. and $CH_2Cl_2$ was added. The reaction was filtered while warm and evaporated to provide the crude product. Recrystallization from ethanol gave 16.62 g (65.4 mmol) of Compound 4a. MS m/z (MH$^+$) 255.

Procedure 5

9-Oxo-9H-xanthene-3-carboxylic acid, 5a

A sample of 9-Oxo-9H-xanthene-3-carboxylic acid methyl ester, compound 4a, (16.6 g, 65.3 mmol) was suspended in 250 mL of 3 N NaOH and 250 mL of EtOH and heated to reflux for 1 h. At that time the EtOH was evaporated and the reaction was poured into 6 N HCl over ice and extracted with large volumes of 1:1 THF/diethyl ether. The combined organic phases were washed with brine, dried over magnesium sulfate, filtered and evaporated to provide 13.35 g of Compound 5a (55.6 mmol) after drying in a vacuum oven at 50° C. overnight.

Procedure 6

9-Oxo-9H-xanthene-3-carboxylic acid diethylamide, 6a

A sample of compound 5a, (13.4 g, 55.6 mmol) was suspended in 220 mL $CH_2Cl_2$ and 24.4 mL (330 mmol) of thionyl chloride was added. The mixture was refluxed over 6 h, adding approximately 10 mL of additional thionyl chloride per hour until the reaction became homogeneous. At that time, the thionyl chloride and solvent were removed under vacuum and the remaining residue was diluted with an additional 220 mL $CH_2Cl_2$. To the suspension was added 100 mL ice cold 1.5 N NaOH, 100 mL $CH_2Cl_2$, and 17 mL (166 mmol) diethyl amine. After stirring for 15 min at room temperature, the phases were separated, and the organic phase was washed with HCl and brine, dried over magnesium sulfate, filtered and concentrated to yield Compound 6a (14.7 g, 49.8 mmol). MS m/z (MH$^+$) 296.

9-Oxo-9H-xanthene-3-carboxylic acid ethylamide, 7a

Following Procedure 6, substituting ethylamine for diethylamine, compound 6a was converted into its monoethyl amide. MS m/z (MH$^+$) 267.9.

Procedure 7

3-(3-Diethylcarbamoyl-xanthen-9-ylidene)-8-aza-bicyclo[3.2.1]octane-8-carboxylic acid ethyl ester, 8a A suspension of zinc metal dust (24.2 g, 370 mmol) in THF (325 mL) under Argon at 5° C. was treated with titanium (IV) tetrachloride (20.3 mL, 180 mmol), dropwise. The reaction was then refluxed for 2 h. The heat was removed and a solution of compound 6a (13.69, 46 mmol), and N-carbethoxynortropinone (9.21 g, 46 mmol) in 100 mL THF was added dropwise. The reaction was refluxed for another 2 h. At that time the reaction was cooled and added to excess potassium carbonate in ice water. The mixture was extracted with EtOAc and the combined extracts were washed with brine, dried over magnesium sulfate, filtered and evaporated to give 22 g of a gum. This crude product was chromatographed using 1:1 EtOAc/hexanes to provide 17 g (36.9 mmol) of Compound 8a. MS m/z (MH$^+$) 461.8.

9-(8-Phenethyl)-8-aza-bicyclo[3.2.1]oct-3-ylidene)-9H-xanthene-3-carboxylic acid ethylamide, 9a The title compound was synthesized following Procedure 7, substituting compound 7a for compound 6a and substituting N-phenethyl-4-tropinone for carbethoxynortropinone. MS m/z=465.1 (M+1); $^1$H NMR 300 MHz (DMSO-$d_6$) δ 1.1 (t, 3H), 1.3 (m, 2H), 2.1 (m, 2H), 2.5 (q, 2H), 3.0-3.4 (m, 8H), 4.05 (m, 2H), 7.1-7.7 (m, 11H), 8.5 (m, 1H).

Procedure 8

9-(8-Aza-bicyclo[3.2.1]oct-3-ylidene)-9H-xanthene-3-carboxylic acid diethylamide, 10a A sample of compound 8a (16.0 g, 34.8 mmol) was dissolved in 35 mL acetic acid and 100 mL of 30% HBr in acetic acid was added to the reaction under Argon before heating on a steam bath for 1 h. The reaction was cooled, added to ice cold NaOH and extracted with $CH_2Cl_2$. The combined organics were washed with brine and dried over potassium carbonate. Evaporation of the solvent provided 12 g of crude Compound 10a, which was purified by column chromatography with 7% 2 N $NH_3$ in methanol/93% $CH_2Cl_2$. to give 7.66 g (19.7 mmol) of Compound 10a. MS m/z=389.3 (M+1); $^1$H NMR 300 MHz (CDCl$_3$) δ 1.1-1.4 (m, 6H), 1.7 (m, 2H), 2.7-3.0 (m, 4H), 3.4 (br s, 4H), 3.5-3.7 (m, 4H), 7.0-7.3 (m, 7H).

9-(8-Methyl-8-aza-bicyclo[3.2.1]oct-3-ylidene)-9H-xanthene-3-carboxylic acid diethylamide, 11a Following Procedure 7 and substituting tropinone for N-carbethoxynortropinone, compound 6a was converted to the title compound. MS m/z=403.2 (M+1); $^1$H NMR 300 MHz (CDCl$_3$) δ 1.2 (br s, 6H), 1.9 (m, 2H), 2.5 (s, 3H), 2.8 (m, 2H), 3.1 (m, 2H), 3.3 (m, 2H), 3.4 (br s, 2H), 3.6 (m, 4H), 7.0-7.3 (m, 7H).

Procedure 9

9-(8-Furan-3-ylmethyl-8-aza-bicyclo[3.2.1]oct-3-ylidene)-9H-xanthene-3-carboxylic acid diethylamide, 12a To a sample of compound 10a (0.65 g, 1.7 mmol) dissolved in 20 mL $CH_2Cl_2$ was added sodium triacetoxyborohydride (0.53 g, 2.5 mmol) and 3-furaldehyde (0.17 mL, 2.0 mmol). The reaction was stirred at room temperature for 24 h. The reaction was diluted with 10 mL $CH_2Cl_2$ and washed with 1 N NaOH. The organic phase was dried over sodium sulfate, filtered, and concentrated. The crude product was purified by flash chromatography, eluting with 5% 0.5 M $NH_3$ in methanol/$CH_2Cl_2$ to give Compound 12a (0.25 g, 0.53 mmol). MS m/z=469.0 (M+1); $^1$H NMR 300 MHz (DMSO-$d_6$) δ 1.1 (br s, 6H), 1.35 (m, 2H), 2.1 (m, 2H), 2.5 (m, 2H), 3.0 (m, 2H), 3.2 (m, 2H), 3.5 (m, 2H), 3.85 (br s, 2H), 4.05 (d, 2H), 6.8 (s, 1H), 7.1-7.5 (m, 7H), 7.8 (s, 1H), 7.9 (s, 1H).

Procedure 10

9-[8-(Methylsulfanyl-ethyl)-8-aza-bicyclo[3.2.1]oct-3-ylidene]-9H-xanthene-3-carboxylic acid diethylamide, 13a A solution of p-toluenesulfonic acid monohydrate (1.4 g, 7.5 mmol) in 20 mL water was added to a stirred solution of (methylthio)acetaldehyde dimethyl acetal (1.0 mL, 7.5 mmol) in 15 mL $CH_2Cl_2$ and the reaction was vigorously stirred for 4 h. The aqueous phase was separated and saturated with NaCl, then extracted with $CH_2Cl_2$. The organic extracts were washed with saturated aqueous sodium bicarbonate and then with brine. The extracts were then dried over magnesium sulfate and filtered. To the filtrate was added compound 10a (0.060 g, 0.15 mmol) and sodium triacetoxyborohydride (0.040 g, 0.19 mmol) and the reaction was stirred at room temperature overnight. The reaction was washed with 1 M NaOH and the organic phase was dried over magnesium sulfate. The solution was concentrated and purified on silica gel using flash chromatography. The product eluted with 10% 0.5 M $NH_3$ in methanol/$CH_2Cl_2$ and was concentrated. Trituration from chloroform and diethyl ether provided pure Compound 13a (0.040 g. 0.086 mmol). MS m/z=463.8 (M+1).

Procedure 11

9-(8-Allyl-8-aza-bicyclo[3.2.1]oct-3-ylidene)-9H-xanthene-3-carboxylic acid diethylamide, 14a To a sample of compound 10a (0.37 g, 0.95 mmol) in 6 mL acetonitrile was added potassium carbonate (0.53 g, 3.81 mmol) and allyl bromide (80 μL, 0.95 mmol). The mixture was stirred at room temperature for 20 h. The reaction was diluted with water and extracted with $CH_2Cl_2$. The combined organic extracts were dried over magnesium sulfate and concentrated. The product was purified by flash column chromatography on silica gel, eluting with 10% 0.5 M $NH_3$ in methanol/$CH_2Cl_2$ to yield 0.11 g (0.25 mmol) of Compound 14a. The product was converted into its HCl salt using ethereal hydrogen chloride. MS m/z=429.0 (M+1); $^1$H NMR 300 MHz (CDCl$_3$) δ 1.1-1.4 (m, 6H), 1.7 (m, 2H), 2.3 (m, 2H), 3.1 (m, 2H), 3.4 (m, 2H), 3.6 (m, 4H), 4.0 (m, 2H), 4.4 (m, 2H), 4.7 (m, 2H), 5.5-5.9 (m, 4H), 6.3 (m, 2H), 7.1-7.4 (m, 7H).

9-[8-(2-Methoxy-ethyl)-8-aza-bicyclo[3.2.1]oct-3-ylidene]-9H-xanthene-3-carboxylic acid diethylamide, 15a Following Procedure 11 and substituting 3 equivalents of 2-bromoethyl methyl ether for allyl bromide, compound 10a was converted to title compound 15a. The product was converted into its HCl salt using ethereal hydrogen chloride. MS m/z=447.4 (M+1); $^1$H NMR 300 MHz (CDCl$_3$) δ 1.0-1.2 (m, 6H), 1.3 (m, 2H), 2.0 (m, 2H), 2.95 (m, 2H), 3.1-3.2 (m, 2H), 3.3 (s, 3H), 3.4 (m, 2H), 3.6 (m, 4H), 3.8 (m, 2H), 4.0 (m, 2H), 7.1-7.4 (m, 7H).

Example B

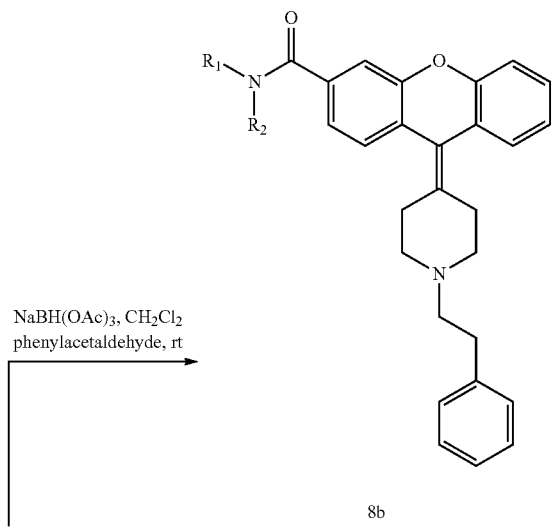

NaBH(OAc)$_3$, CH$_2$Cl$_2$
phenylacetaldehyde, rt

8b

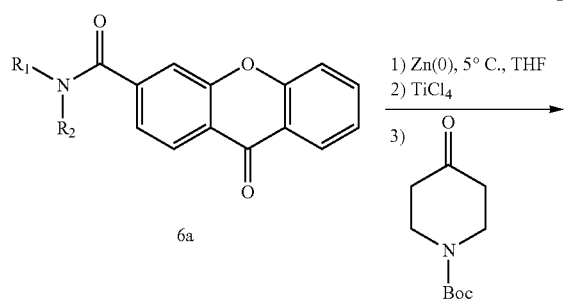
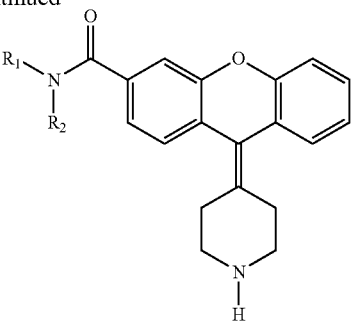
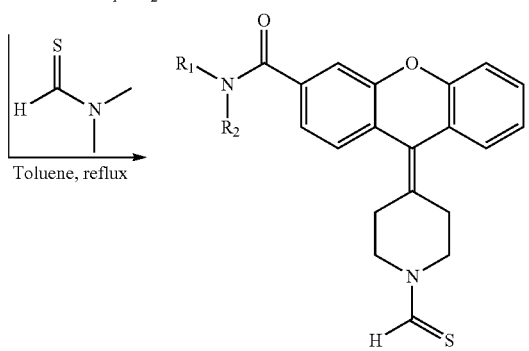
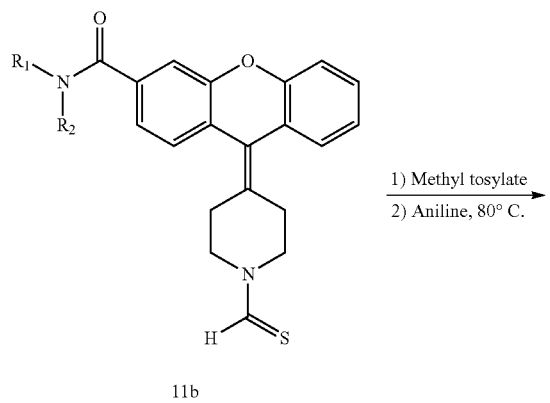
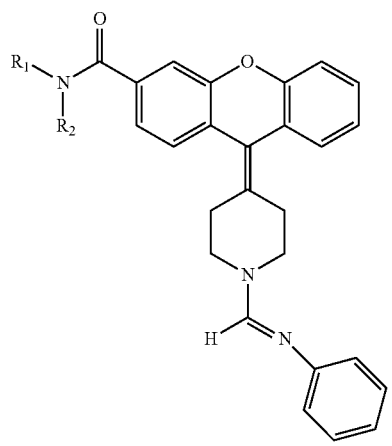

9-Piperidin-4-ylidene-9H-xanthene-3-carboxylic acid diethylamide, fumarate 1b

Following Procedure 7, substituting N-Boc-piperidone for N-carbethoxynortropinone, the Compound 1b was synthesized in one step from compound 6a with the simultaneous removal of the Boc-protecting group. Purification was performed on silica gel using flash chromatography. The product eluted with 10% 2 N $NH_3$ in methanol/$CH_2Cl_2$. A fumarate salt was prepared from 2-PrOH. MS m/z ($MH^+$) 363.2; $^1H$ NMR 300 MHz (DMSO-$d_6$) δ 1.1 (br s, 6H), 2.8 (m, 4H), 2.95 (m, 4H), 3.3, 3.4 (br s, 4H), 6.4 (s, 2H) 7.1-7.5 (m, 7H).

9-Piperidin-4-ylidene-9H-xanthene-3-carboxylic acid ethylamide, 2b

Following Procedure 7, substituting compound 7a for compound 6a and substituting N-Boc-piperidone for N-carbethoxynortropinone, the title compound 2b was synthesized. MS m/z ($MH^+$) 334.8.

9-(1-Furan-3-ylmethyl-piperidin-4-ylidene)-9H-xanthene-3-carboxylic acid diethylamide, Hydrochloride 3b Following Procedure 9, compound 1b was converted to the title compound 3b. The crude product was purified by flash chromatography on silica gel, eluting with 3% methanol/$CH_2Cl_2$ to yield the product. A hydrochloride salt was prepared from Et₂O/HCl. MS m/z (MH⁺) 363.2; ¹H NMR 300 MHz (DMSO-d₆) δ 1.2 (br d, 6H), 2.4 (m, 2H), 3.3-3.6 (m, 10H), 4.0 (s, 2H), 6.8 (s, 1H) 7.1-7.3 (m, 7H), 7.5 (s, 1H), 7.7 (s, 1H), 13.1 (s, 1H).

Procedure 12

9-(1-Carbamimidoyl-piperidin-4-ylidene)-9H-xanthene-3-carboxylic acid diethylamide, 4b A solution of compound 2b, (0.025 g, 0.069 mmol) and c (0.015 g, 0.36 mmol) were refluxed in 4 mL water. After 3 h, the reaction was 50% complete. Additional cyanamide was added and the mixture was heated for an additional 24 h. The reaction was cooled to room temperature and concentrated under vacuum. Purification of the crude material was performed by HPLC, 15-70% acetonitrile/water/0.1% TFA. The TFA salt of Compound 4b was isolated (1.4 mg, 3.5 μmol). MS m/z=405.1 (M+1); ¹H NMR 300 MHz (DMSO-d₆) δ 1.1 (br s, 6H), 2.8 (m, 4H), 3.2 (m, 2H), 3.5 (m, 6H), 7.1-7.5 (m, 7H).

9-(R³-piperidin-4-ylidene)-9H-xanthene-3-carboxylic acid diethylamide, 5b-8b

Following Procedure 9, substituting the appropriate aldehyde for 3-furaldehyde, the following compounds were prepared:

| Ex # | Aldehyde | R³ | MS m/z (MH⁺) |
|---|---|---|---|
| 5b | 2-pyridinecarboxaldehyde | Pyridin-2-yl methyl | 454.5 |
| 6b | salicylaldehyde | 2-Hydroxy benzyl | 469.2 |
| 7b | formalin | Methyl | 377.26 |
| 8b | phenylacetaldehyde | Phenethyl | 467.33 |

9-(1-Prop-2-ynyl-piperidin-4-ylidene)-9H-xanthene-3-carboxylic acid diethylamide Hydrochloride, 9b Following Procedure 11, substituting propargyl bromide for allyl bromide, compound 1b was refluxed for 12 h in acetonitrile. The crude product was purified by flash column chromatography on silica gel, eluting with 3% methanol/CH₂Cl₂, and then converted to its hydrochloride salt with ethereal hydrogen chloride. MS m/z (MH⁺) 401.4; ¹H NMR 300 MHz (CDCl₃) δ 1.2 (br d, 6H), 2.6 (s, 1H), 2.9 (m, 2H) 3.1-3.6 (m, 10H), 3.9 (s, 2H),) 7.15-7.3 (m, 7H), 13.5 (s, 1H).

9-[1-(2-Hydroxy-ethyl)-piperidin-4-ylidene]-9H-xanthene-3-carboxylic acid diethylamide, 10b Following Procedure 11, substituting 2-iodo-ethanol for allyl bromide, the title compound was prepared from compound 1b. MS m/z (MH⁺) 407.0; ¹H NMR 300 MHz (CDCl₃) δ 1.2 (br d, 6H), 1.7 (m, 2H), 2.8 (m, 2H), 3.1 (m, 2H), 3.2-3.8 (m, 8H), 4.0 (m, 2H), 4.8 (m, 1H), 7.15-7.3 (m, 7H).

Procedure 13

9-(1-Thioformyl-piperidin-4-ylidene)-9H-xanthene-3-carboxylic acid diethylamide, 11b A sample of compound 1b (0.77 g, 2.1 mmol) was refluxed in 2 mL toluene with N,N-dimethyl-thioformamide (0.36 mL, 4.24 mmol) for 5 h. The crude product was purified on a flash column through silica gel, eluting with 45% ethyl acetate in hexanes to yield 0.66 g (1.6 mmol) of Compound 11b. Two rotamers were observed by ¹H-NMR. MS m/z (MH⁺) 406.9. ¹H NMR 300 MHz (CDCl₃) δ 1.2 (br d, 6H), 2.9 (m, 3H), 3.3 (m, 2H) 3.4-3.7 (m, 3H), 3.9 (m, 2H), 7.1-7.4 (m, 7H), 9.3 (s, 1H).

Procedure 14

9-(1-Phenyliminomethyl-piperidin-4-ylidene)-9H-xanthene-3-carboxylic acid diethylamide, 12b A sample of compound 11b (0.1 g, 0.25 mmol) in 1 mL of chloroform was placed in a pressure tube and treated with methyl tosylate (0.037 mL, 0.25 mmol). The reaction was heated for 1 h on a steam bath. At that time the reaction was cooled to room temperature and aniline (0.023 mL, 0.25 mmol) was added, and the reaction was heated again on a steam bath for another 2 h. After 2 h, the reaction was cooled, washed with 1 N NaOH, and evaporated. Flash chromatography on silica gel was used to purify the crude material, eluting the product with 5% methanol/CH₂Cl₂, followed by conversion to its hydrochloride salt with ethereal hydrogen chloride (0.004 g, 0.009 mmol). MS m/z (MH⁺) 466.3. ¹H NMR 300 MHz (CDCl₃) δ 1.2 (br s, 6H), 3.1 (m, 4H), 3.3 (d, 2H) 3.4-3.8 (m, 4H), 4.3 (s, 2H),) 7.1-7.4 (m, 10H), 7.7 (s, 2H), 8.0 (s, 1H), 13.6 (s, 1H).

9-(1-Allyl-piperidin-4-ylidene)-9H-xanthene-3-carboxylic acid diethylamide, 13b

Following Procedure 11, and substituting compound 1b for Compound 10a, Compound 1b was converted to the title compound 13b. MS m/z (MH⁺) 403.3 ¹H NMR 300 MHz (CDCl₃) δ 1.2 (br d, 6H), 2.5 (m, 2H), 3.1-3.7 (m, 12H), 5.4 (m, 2H),) 6.2 (m, 1H), 7.1-7.3 (m, 7H).

Example C

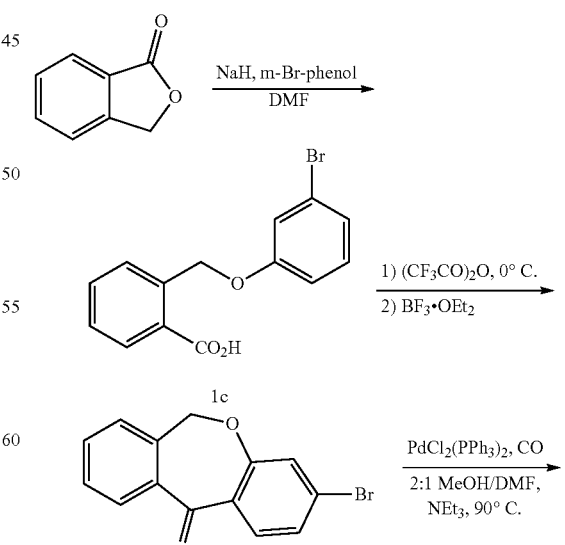

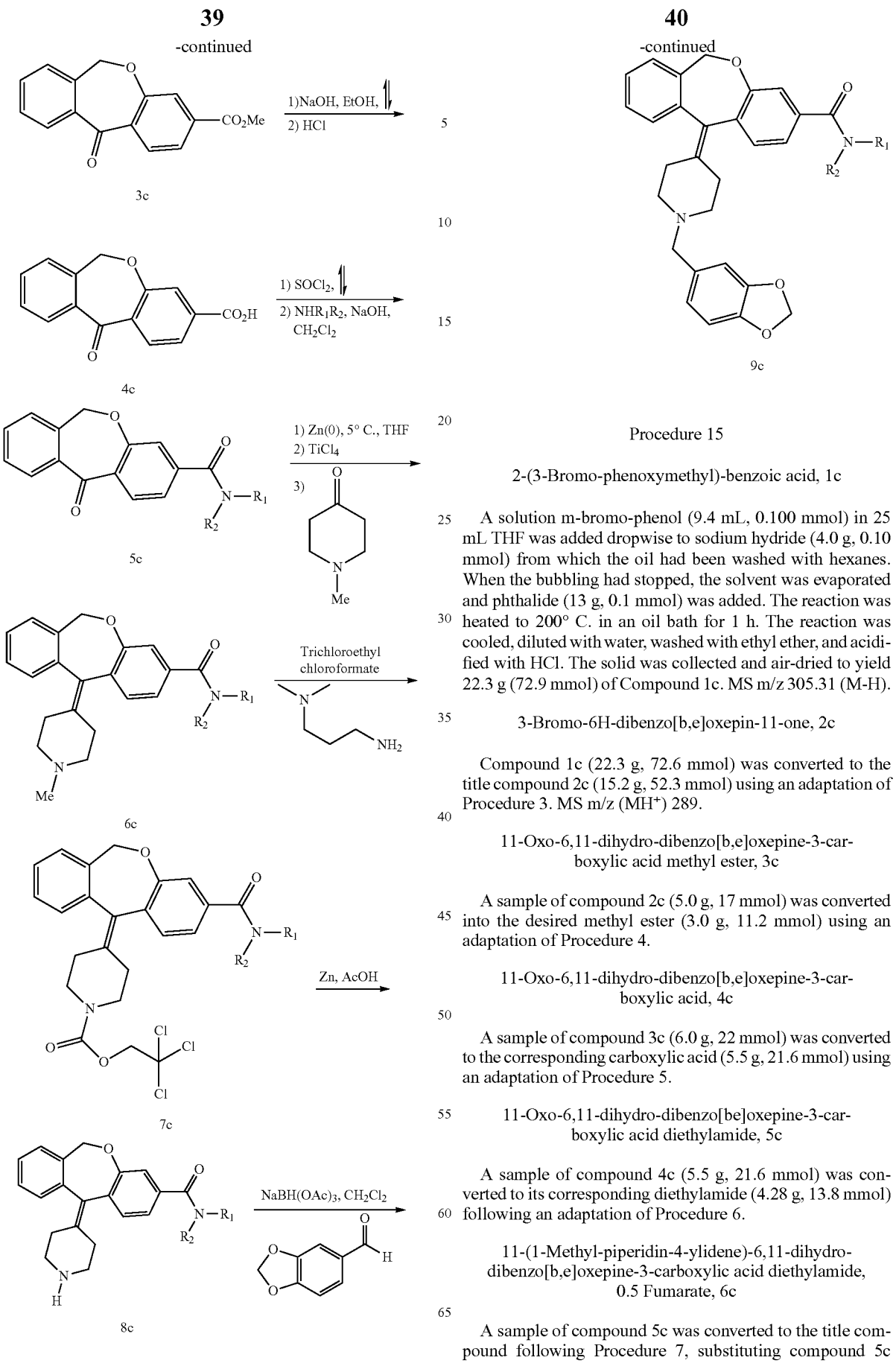

Procedure 15

2-(3-Bromo-phenoxymethyl)-benzoic acid, 1c

A solution m-bromo-phenol (9.4 mL, 0.100 mmol) in 25 mL THF was added dropwise to sodium hydride (4.0 g, 0.10 mmol) from which the oil had been washed with hexanes. When the bubbling had stopped, the solvent was evaporated and phthalide (13 g, 0.1 mmol) was added. The reaction was heated to 200° C. in an oil bath for 1 h. The reaction was cooled, diluted with water, washed with ethyl ether, and acidified with HCl. The solid was collected and air-dried to yield 22.3 g (72.9 mmol) of Compound 1c. MS m/z 305.31 (M-H).

3-Bromo-6H-dibenzo[b,e]oxepin-11-one, 2c

Compound 1c (22.3 g, 72.6 mmol) was converted to the title compound 2c (15.2 g, 52.3 mmol) using an adaptation of Procedure 3. MS m/z (MH$^+$) 289.

11-Oxo-6,11-dihydro-dibenzo[b,e]oxepine-3-carboxylic acid methyl ester, 3c

A sample of compound 2c (5.0 g, 17 mmol) was converted into the desired methyl ester (3.0 g, 11.2 mmol) using an adaptation of Procedure 4.

11-Oxo-6,11-dihydro-dibenzo[b,e]oxepine-3-carboxylic acid, 4c

A sample of compound 3c (6.0 g, 22 mmol) was converted to the corresponding carboxylic acid (5.5 g, 21.6 mmol) using an adaptation of Procedure 5.

11-Oxo-6,11-dihydro-dibenzo[be]oxepine-3-carboxylic acid diethylamide, 5c

A sample of compound 4c (5.5 g, 21.6 mmol) was converted to its corresponding diethylamide (4.28 g, 13.8 mmol) following an adaptation of Procedure 6.

11-(1-Methyl-piperidin-4-ylidene)-6,11-dihydro-dibenzo[b,e]oxepine-3-carboxylic acid diethylamide, 0.5 Fumarate, 6c A sample of compound 5c was converted to the title compound following Procedure 7, substituting compound 5c (3.85 g, 12.5 mmol) for compound 6a and substituting N-methyl-piperidone for N-carbethoxynortropinone. The reaction yielded 2.5 g (6.4 mmol) of Compound 6c. MS m/z (MH$^+$) 391.28; $^1$H NMR 300 MHz (DMSO) δ 1.0 (br s, 6H), 2.5 (m, 2H), 3.1-3.7 (m, 12H), 5.4 (m, 2H),) 6.2 (m, 1H), 7.1-7.3 (m, 7H).

Procedure 16

4-(3-Diethylcarbamoyl-6H-dibenzo[b,e]oxepin-11-ylidene)-piperidine-1-carboxylic acid 2,2,2-trichloroethyl ester, 7c A sample of compound 6c (2.58 g, 6.41 mmol), trichloroethyl chloroformate (1.33 mL, 9.7 mmol) and potassium carbonate (3.34 g, 24.2 mmol) were refluxed for 3.5 h in benzene. An additional 4 mL of trichloroethyl chloroformate was added and the reaction was refluxed for another hour. Dimethyl aminopropylamine (5 mL) was added, and the reaction went to completion. The mixture was extracted with 2 N HCl, washed with brine, and the organic phase was dried over magnesium sulfate, filtered and then evaporated. The crude product was recrystallized from acetone/hexane to give 2 g (3.6 mmol) of Compound 7c. MS m/z (MH$^+$) 551.31.

Procedure 17

11-Piperidin-4-ylidene-6,11-dihydro-dibenzo[b,e]oxepin-11-ylidene-piperidine-1-carboxylic acid diethylamide, 8c A sample of compound 7c (1.75 g, 3.17 mmol) and zinc (1.51 g, 23.1 mmol) was stirred in acetic acid (17.5 mL) at room temperature. The resulting solids were collected by filtration and washed with additional acetic acid. The filtrate was concentrated, partitioned between NaOH and CH$_2$Cl$_2$. The organic phase was collected and dried over potassium carbonate, and evaporated. The crude product was recrystallized from acetonitrile to give Compound 8c (1.2 g, 3.2 mmol). MS m/z (MH$^+$) 377.28; $^1$H NMR 300 MHz (CDCl$_3$) δ 1.2 (br d, 6H), 2.3 (m, 2H), 2.4-3.1 (m, 6H) 3.4 (br d, 4H), 4.8 (d, 1H),) 5.8 (d, 1H) 6.8 (d, 1H), 7.0 (m, 1H), 7.1 (d, 1H), 7.2-7.4 (m, 4H).

11-(1-Benzo[1,3]dioxol-5-ylmethyl-piperidin-4-ylidene)-6,11-dihydro-dibenzo[b,e]oxepine-3-carboxylic acid diethylamide Hydrochloride, 9c Following Procedure 9, substituting benzo[1,3]dioxole-5-carbaldehyde for 3-furaldehyde and compound 8c for compound 10a, the title compound was prepared. The crude product was converted into its HCl salt using ethereal hydrogen chloride. MS m/z (MH$^+$) 511.34; $^1$H NMR 300 MHz (CDCl$_3$) δ 1.2 (br d, 6H), 2.3-2.7 (m, 12H), 2.4-3.1 (m, 6H), 4.05 (s, 2H), 4.8 (d, 1H),) 5.7 (d, 1H) 6.8-7.4 (m, 10H).

11-(1-Phenylethylpiperidin-4-ylidene)-6,11-dihydro-dibenzo[b,e]oxepine-3-carboxylic diethylamide Hydrochloride 10c Following Procedure 9, compound 8c was converted to the title compound, substituting phenylacetaldehyde for 3-furaldehyde, and compound 8c for compound 10a. The crude product was converted into its HCl salt using ethereal hydrogen chloride. MS m/z (MH$^+$) 481.35; $^1$H NMR 300 MHz (CDCl$_3$) δ 1.2 (br d, 6H), 2.3-2.7 (m, 12H), 2.4-3.7 (m, 16H), 4.8 (d, 1H), 5.7 (d, 1H), 6.8-7.4 (m, 12H).

11-Oxo-6,11-dihydro-dibenzo[b,e]oxepine-3-carboxylic acid ethylamide, 11c

Following an adaptation of Procedure 6, substituting ethylamine for diethylamine, compound 4c was converted into its monoethyl amide.

11-(8-Phenethyl-8-aza-bicyclo[3.2.1]oct-3-ylidene)-6,11-dihydro-dibenzo[b,e]oxepine-3-carboxylic acid ethylamide, 12c A sample of compound 11c was converted to the title compound following Procedure 7, substituting compound 11c for compound 6a and substituting N-phenethyl-4-tropinone for N-carbethoxynortropinone. The title compound was isolated as its TFA salt. MS m/z 479.1 (M+1); $^1$H NMR 300 MHz (DMSO-d$_6$) δ 1.1 (t, 3H), 1.35 (m, 1H), 1.8 (m, 1H), 2.2 (m, 2H), 2.5 (m, 2H), 2.8 (dd, 2H), 3.1 (m, 2H), 3.3 (m, 2H), 3.75 (m, 2H), 4.1 (m, 2H), 5.0 (m, 1H), 5.7 (m, 1H), 7.0-7.7 (m, 11H), 8.4 (7, 1H), 10.0 (br s, 1H).

11-(1-Allyl-piperidin-4-ylidene)-6,11-dihydro-dibenzo[b,e]oxepine-3-carboxylic acid diethylamide, 13c Following Procedure 11, substituting compound 8c for compound 10a, the title compound was prepared. MS m/z (MH$^+$) 417.33; $^1$H NMR 300 MHz (CDCl$_3$) δ 1.2 (br d, 6H), 2.4 (m, 1H), 2.6 (m, 1H), 2.8 (m, 2H), 3.0-3.8 (m, 10H), 4.8 (d, 1H), 5.3-5.7 (m, 3H), 6.2 (m, 1H), 6.8-7.4 (m, 7H).

Example D

Grignard Method

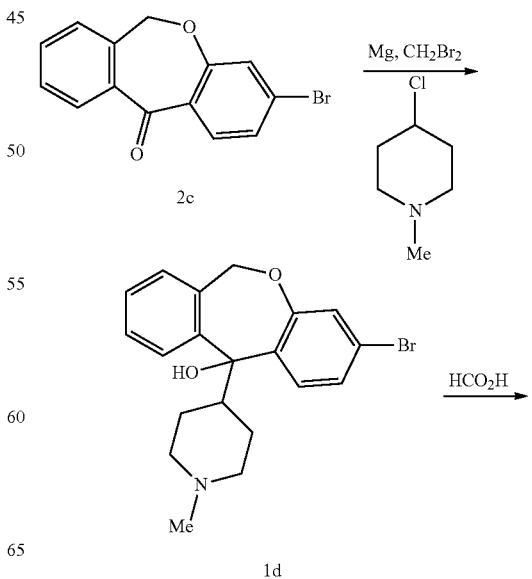

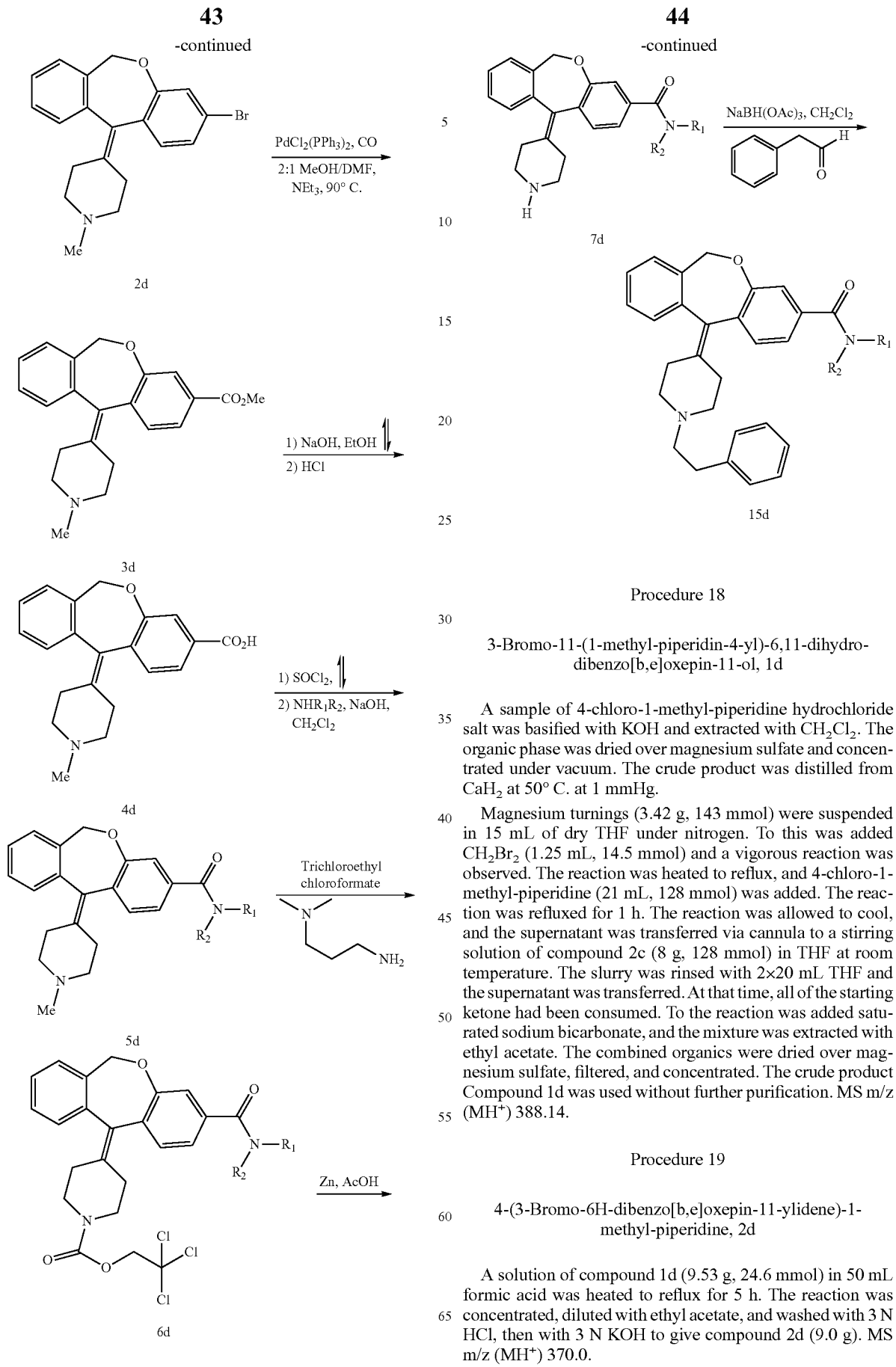

Procedure 18

3-Bromo-11-(1-methyl-piperidin-4-yl)-6,11-dihydro-dibenzo[b,e]oxepin-11-ol, 1d

A sample of 4-chloro-1-methyl-piperidine hydrochloride salt was basified with KOH and extracted with $CH_2Cl_2$. The organic phase was dried over magnesium sulfate and concentrated under vacuum. The crude product was distilled from $CaH_2$ at 50° C. at 1 mmHg.

Magnesium turnings (3.42 g, 143 mmol) were suspended in 15 mL of dry THF under nitrogen. To this was added $CH_2Br_2$ (1.25 mL, 14.5 mmol) and a vigorous reaction was observed. The reaction was heated to reflux, and 4-chloro-1-methyl-piperidine (21 mL, 128 mmol) was added. The reaction was refluxed for 1 h. The reaction was allowed to cool, and the supernatant was transferred via cannula to a stirring solution of compound 2c (8 g, 128 mmol) in THF at room temperature. The slurry was rinsed with 2×20 mL THF and the supernatant was transferred. At that time, all of the starting ketone had been consumed. To the reaction was added saturated sodium bicarbonate, and the mixture was extracted with ethyl acetate. The combined organics were dried over magnesium sulfate, filtered, and concentrated. The crude product Compound 1d was used without further purification. MS m/z $(MH^+)$ 388.14.

Procedure 19

4-(3-Bromo-6H-dibenzo[b,e]oxepin-11-ylidene)-1-methyl-piperidine, 2d

A solution of compound 1d (9.53 g, 24.6 mmol) in 50 mL formic acid was heated to reflux for 5 h. The reaction was concentrated, diluted with ethyl acetate, and washed with 3 N HCl, then with 3 N KOH to give compound 2d (9.0 g). MS m/z $(MH^+)$ 370.0.

11-(1-Methyl-piperidin-4-ylidene)-6,11-dihydro-dibenzo[b,e]oxepine-3-carboxylic acid methyl ester, 3d The title compound 3d was synthesized using an adaptation of Procedure 4. MS m/z (MH$^+$) 350.2.

11-(1-Methyl-piperidin-4-ylidene)-6,11-dihydro-dibenzo[b,e]oxepine-3-carboxylic acid, 4d The title compound 4d was synthesized from compound 3d using an adaptation of Procedure 5.

11-(1-Methyl-piperidin-4-ylidene)-6,11-dihydro-dibenzo[b,e]oxepine-3-carboxylic acid ethylamide, 5d The title compound was synthesized from compound 4d using an adaptation of Procedure 6, substituting ethylamine for diethylamine. MS m/z (MH$^+$) 363.0.

4-(3-Ethylcarbamoyl-6H-dibenzo[b,e]oxepin-11-ylidene)-piperidine-1-carboxylic acid 2,2,2-trichloro-ethyl ester, 6d The title compound was synthesized from compound 5d using an adaptation of Procedure 16. MS m/z (MH$^+$) 523.0.

11-Piperidin-4-ylidene-6,11-dihydro-dibenzo[b,e]oxepine-3-carboxylic acid ethylamide, 7d Compound 6d was converted to the title compound using an adaptation of Procedure 17. MS m/z (MH$^+$) 349.0.

Following Procedure 9, compound 7d was converted into the following series of compounds, substituting the appropriate aldehyde for 3-furaldehyde:

| Ex # | Aldehyde | R$^3$ | MS m/z (MH$^+$) |
|---|---|---|---|
| 8d | 4-Methyl-but-3-enal | 2-Methyl-but-2-ene | 417.1 |
| 9d | Thiophene-2-carbaldehyde | Thiophen-2-yl methyl | 445.1 |
| 10d | 2-Methyl-propenal | 2-Methyl-allyl | 403.1 |
| 11d | Cyclopropanecarbaldehyde | Cyclopropylmethyl | 403.1 |
| 12d | 2-Pyridinecarboxaldehyde | Pyridin-2-yl methyl | 440.1 |
| 13d | 1H-Imidazole-4-carbaldehyde | 1H-Imidazol-4-yl methyl | 429.1 |
| 14d | 4-Hydroxy-3-methoxy-benzaldehyde | 4-Hydroxy-3-methoxy-phenylmethyl | 485.1 |
| 15d | Phenyl-acetaldehyde | Phenethyl | 453.2 |

11-(1-Allyl-piperidin-4-ylidene)-6,11-dihydro-dibenzo[b,e]oxepine-3-carboxylic acid ethylamide, 16d Following Procedure 11, substituting compound 7d for compound 10a, the title compound 16d was prepared. MS m/z (MH$^+$) 389.1.

Example E

McMurry on Bromide

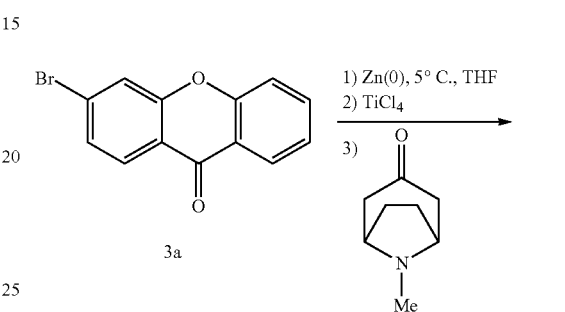

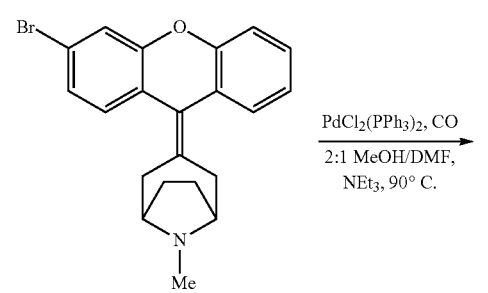

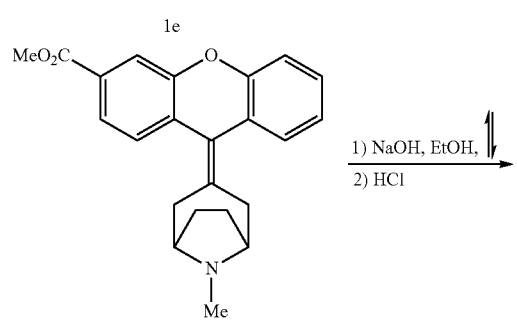

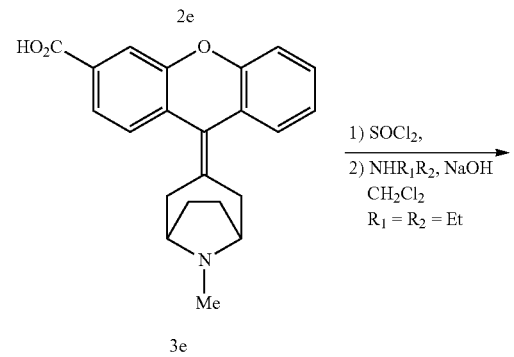

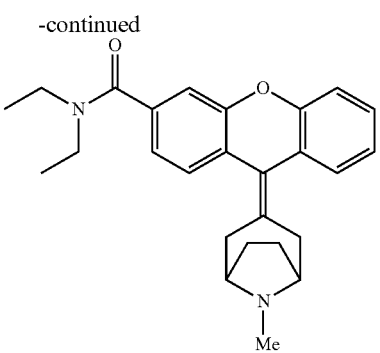

7b

4-(3-Bromo-xanthen-9-ylidene)-1-methyl-piperidine, 1e

Compound 3a was converted into the title compound 1e following an adaptation of Procedure 7, substituting compound 3a for compound 6a and substituting N-Methyl-piperidone for N-carbethoxynortropinone. MS m/z (MH+) 356.

9-(1-Methyl-piperidin-4-ylidene)-9H-xanthene-3-carboxylic acid methyl ester, 2e Compound 1e was converted into its methyl ester 2e by an adaptation of Procedure 4. MS m/z (MH+) 336.1.

9-(1-Methyl-piperidin-4-ylidene)-9H-xanthene-3-carboxylic acid, 3e

Compound 2e was converted into the corresponding carboxylic acid compound 3e by an adaptation of Procedure 5. MS m/z (MH+) 321.1.

9-(1-Methyl-piperidin-4-ylidene)-9H-xanthene-3-carboxylic acid diethylamide, 7b Compound 3e was converted into the title diethylamide, compound 7b, using an adaptation of Procedure 6.

Example F

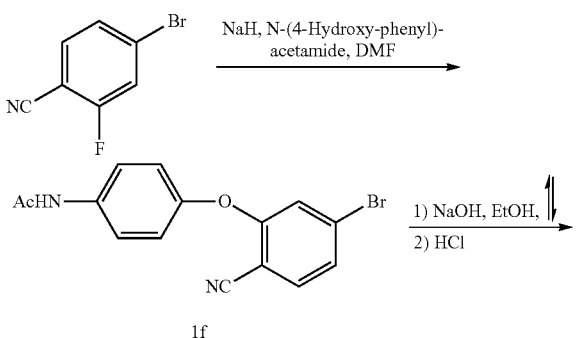

1f

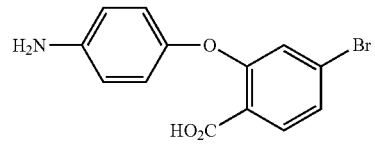

2f

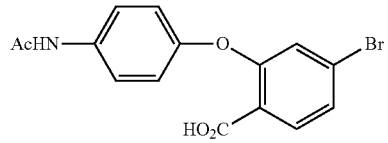

3f

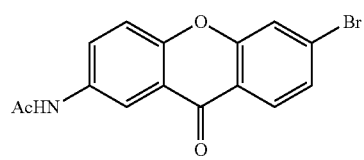

4f

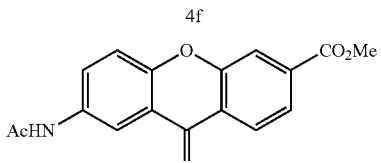

5f

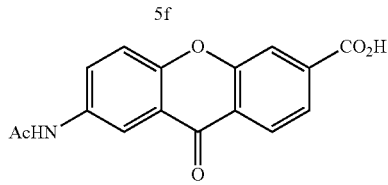

6f

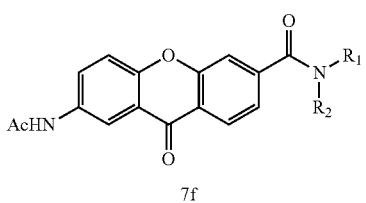

7f

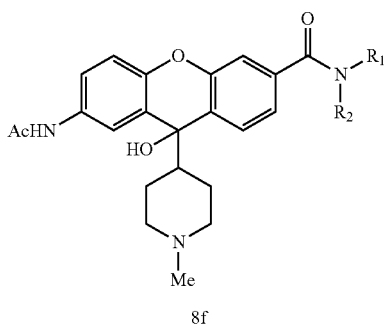

8f

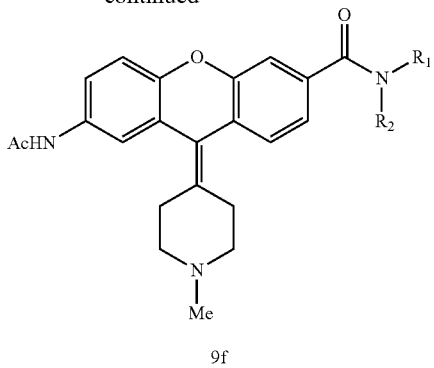

9f

N-[4-(5-Bromo-2-cyano-phenoxy)-phenyl]-acetamide, 1f

Compound 1f was synthesized by that described for the synthesis of compound 1a in Procedure 1, substituting N-(4-hydroxyphenyl)-acetamide for phenol.

2-(4-Amino-phenoxy)-4-bromo-benzoic acid, 2f

Using the method described in Procedure 2, substituting compound 1f for compound 1a, the title compound 2f was synthesized in quantitative yield. CIMS m/z=307 (M+1).

Procedure 20

2-(4-Acetylamino-phenoxy)-4-bromo-benzoic acid, 3f

Compound 2f (500 mg, 1.6 mmol) in 10 mL of THF was treated with acetyl chloride (0.15 mL, 2.08 mmol) and triethylamine (0.22 mL, 2.08 mmol). After stirring for 2.5 h the solid was collected. The filtrate was evaporated in vacuo to give 0.48 g of Compound 3f. MS m/z=331 (M+1).

N-(6-Bromo-9-oxo-9H-xanthen-2-yl)-acetamide, 4f

The title compound was synthesized using an adaptation of Procedure 3, substituting compound 3f for compound 2a.

7-Acetylamino-9-oxo-9H-xanthene-3-carboxylic acid methyl ester, 5f

The title compound was synthesized using an adaptation of Procedure 4, substituting compound 4f for compound 3a.

7-Acetylamino-9-oxo-9H-xanthene-3-carboxylic acid, 6f

The title compound was synthesized using an adaptation of Procedure 5, substituting compound 5f for compound 4a.

Procedure 21

7-Acetylamino-9-oxo-9H-xanthene-3-carboxylic acid diethylamide, 7f

Compound 6f (2 g, 6.7 mmol) in 35 mL of DMF was treated with HATU (2.5 g, 6.7 mmol), diethylamine (0.2 mL, 8.7 mmol), and diisopropylethylamine (4.75 mL, 26.8 mmol). After stirring for 3 h the reaction was poured into water and the solid was collected to give the product, compound 7f. The filtrate was extracted with diethyl ether/THF (1:1). The combined organic phases were washed with water, brine, and dried over magnesium sulfate. The solvent was evaporated in vacuo and combined with the above solid to give 1.5 g total of compound 7f. MS m/z=353 (M+1).

7-Acetylamino-9-hydroxy-9-(1-methyl-piperidin-4-yl)-9H-xanthene-3-carboxylic acid diethylamide, 8f The title compound was synthesized by an adaptation of Procedure 18, substituting compound 7f for compound 2c.

Procedure 22

7-Acetylamino-9-(1-methyl-piperidin-4-ylidene)-9H-xanthene-3-carboxylic acid diethylamide, 9f Into a flask was placed compound 8f (0.3 g, 0.66 mmol) and trifluoromethanesulfonic acid (2 mL). After heating on a steam bath for 1 h the reaction was poured into 3 N NaOH and ice. The aqueous solution was extracted with $CH_2Cl_2$ and dried over sodium sulfate. The solvent was evaporated in vacuo and the resulting residue was passed through a flash column (silica gel; 90:10:1 $CH_2Cl_2$:$CH_3OH$:$NH_4OH$) to give 0.01 g of compound 9f. MS m/z=435 (M+1).

7-Acetylamino-9-piperidin-4-ylidene-9H-xanthene-3-carboxylic acid diethylamide, 10f Compound 10f was synthesized by an adaptation of Procedure 7, substituting compound 7f for compound 6a, and substituting N-Boc-piperidone for N-carbethoxynortropinone. MS m/z=420.3 (M+1).

Example G

Procedure 23

9-Piperidin-4-yl-9H-xanthene-3-carboxylic acid diethylamide, Hydrochloride

A sample of the hydrochloride salt of compound 1b (0.19 g, 0.52 mmol) was dissolved in 3 mL of $CHCl_3$, treated with iodotrimethylsilane (0.15 mL), sealed in a pressure tube and heated on a steam bath for 2 h. The mixture was cooled and the tube was opened. A second portion of iodotrimethylsilane (0.15 mL) was added, the tube was recapped, and the vessel heated an additional 3 h on the steam bath. The reaction was cooled and 3 mL of MeOH was added. The reaction mixture was partitioned between $CH_2Cl_2$ and NaOH solution. The organic layer was washed with sodium dithionite solution. The solvent was evaporated and the residue flash chromatographed with 90% $CH_2Cl_2$: 10% 2N $NH_3$ in MeOH to give the title compound. A hydrochloride salt was prepared from $Et_2O$/HCl. MS m/z ($MH^+$) 364.9; $^1H$ NMR 300 MHz ($CDCl_3$) δ 1.2 (br s, 6H), 1.5 (m, 2H), 1.7 (m, 2H), 2.8 (m, 2H), 3.2-3.4 (m, 4H), 3.5 (br s, 2H), 3.7 (d, 1H), 7.1-7.3 (m, 7H).

9-(1-Methylpiperidin-4-yl)-9H-xanthene-3-carboxylic acid diethylamide, Hydrochloride Following the protocol of Procedure 23 and substituting the hydrochloride salt of compound 7b for the hydrochloride salt of compound 1b, the title compound was obtained. MS m/z ($MH^+$) 364.9; $^1H$ NMR 300 MHz ($CDCl_3$) δ 1.2 (br s, 6H), 1.4 (m, 1H), 1.7 (m, 2H), 2.05 (q, 2H), 2.7 (s, 3H), 3.1-3.5 (m, 6H), 3.7 (d, 1H), 7.1-7.3 (m, 7H), 12.2 (s, 1H).

Example H

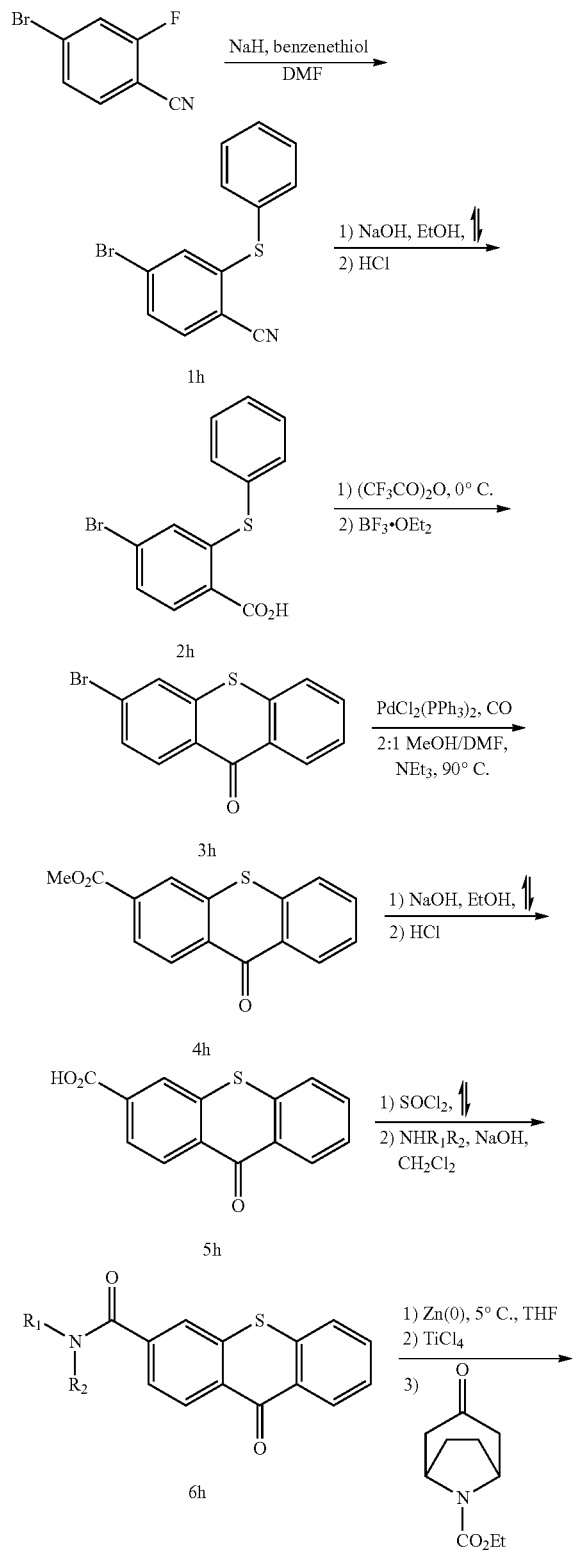

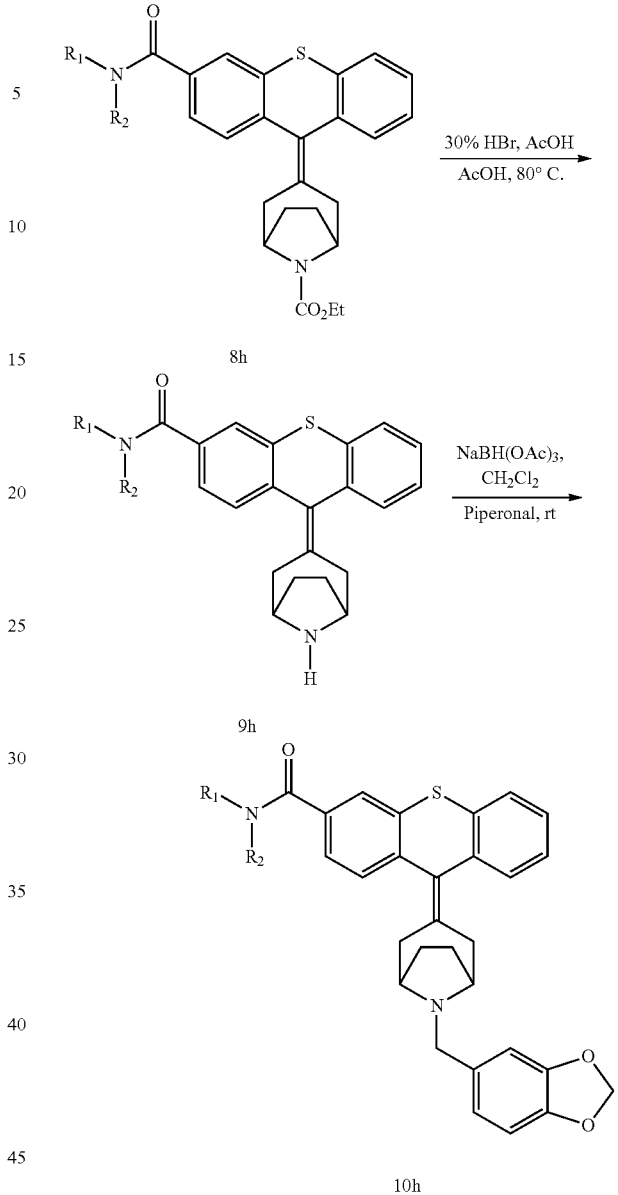

Procedure 24

4-Bromo-2-phenylsulfanyl-benzonitrile, 1 h

Sodium hydride (2.40 g, 60 mmol) (60% by wt) was weighed into a flask and washed with several hexane rinsings. The hexanes were decanted and discarded and 20 mL DMF was added to the flask. A DMF-solution of benzenethiol (5.1 mL, 50 mmol in 50 mL DMF) was added dropwise to the NaH mixture and stirred at room temperature. To 4-bromo-2-fluoro-benzonitrile (10.0 g, 50 mmol) in 40 mL DMF) was added benzenethiophenoxide (described above), dropwise, over 30 minutes. Upon complete addition, the reaction was stirred at room temperature for 20 min. At that time, the mixture was poured into cold 1 N NaOH. A precipitate formed and was collected by vacuum filtration to give 14.0 g (48.4 mmol) of Compound 1h.

4-Bromo-2-phenylsulfanyl-benzoic acid, 2h

Following Procedure 2, substituting compound 1h for compound 1a, Compound 2h was obtained.

3-Bromo-thioxanthen-9-one, 3h

Following Procedure 3, substituting Compound 2h for compound 2a, compound 3h was obtained.

9-Oxo-9H-thioxanthene-3-carboxylic acid methyl ester, 4h

Following Procedure 4, substituting compound 3h for compound 3a, compound 4h was obtained.

9-Oxo-9H-thioxanthene-3-carboxylic acid, 5h

Following Procedure 5, substituting compound 4h for compound 4a, Compound 5h was obtained.

9-Oxo-9H-thioxanthene-3-carboxylic acid diethylamide, 6h

Following Procedure 6, substituting compound 5h for compound 5a, Compound 6h was obtained.

9-Oxo-9H-thioxanthene-3-carboxylic acid ethylamide, 7h

Following Procedure 6, substituting ethylamine for diethylamine, and compound 5h for compound 5a Compound 7h was obtained.

3-(3-Diethylcarbamoyl-thioxanthen-9-ylidene)-8-aza-bicyclo[3.2.1]octane-8-carboxylic acid ethyl ester, 8h Following the procedure described in Procedure 7, substituting compound 6h for compound 6a, Compound 8c was obtained. MS m/z=477.1 (MH+).

9-(8-Aza-bicyclo[3.2.1]oct-3-ylidene)-9H-thioxanthene-3-carboxylic acid diethylamide, 9h Following Procedure 8, substituting compound 8h for compound 8a, Compound 9h was obtained. The product was then converted into its fumarate salt. MS m/z (MH+)=405.4. $^1$H NMR 300 MHz (CDCl$_3$) δ 1.05-1.3 (m, 6H), 1.40 (m, 2H), 1.9 (m, 2H), 2.75 (m, 2H), 3.1 (m, 2H), 3.3 (m, 2H), 3.6 (m, 2H), 3.90 (br s, 2H), 7.2 (m, 5H), 7.5 (m, 2H).

9-(8-Benzo[1,3]dioxol-5-ylmethyl-8-aza-bicyclo[3.2.1]oct-3-ylidene)-9H-thioxanthene-3-carboxylic acid diethylamide, 10h Following Procedure 9, substituting compound 9h for compound 10a, and substituting piperonal for 3-furaldehyde, Compound 10h was obtained. The product was then converted into its fumarate salt. MS m/z (MH+)=439.4. Fumarate salt: $^1$H NMR 300 MHz (DMSO-d$_6$) δ 0.9-1.2 (m, 8H), 1.90 (m, 2H), 2.55 (m, 2H), 2.95 (m, 2H), 3.19 (m, 2H), 3.4 (m, 4H), 3.80 (br s, 2H), 6.05 (s, 2H), 6.65 (s, 2H), 6.9 (m, 2H), 7.2 (s, 1H), 7.35 (m, 5H), 7.6 (m, 2H).

9-(R$^3$-8-aza-bicyclo[3.2.1]oct-3-ylidene)-9H-thioxanthene-3-carboxylic acid diethylamide, 11h-12h Following Procedure 9, substituting the appropriate aldehyde for 3-furancarboxaldehyde, the following compounds were prepared:

| Ex # | Aldehyde | R$^3$ | MS m/z (MH+) |
|---|---|---|---|
| 11h | Cyclopropane carboxaldehyde | Cyclopropylmethyl | 459.7 |
| 12h | 3-(Methylthio)-3-propionaldehyde | Methanesulfanyl-propyl | 493.5 |

9-[8-(2Hydroxy-ethyl)-8-aza-bicyclo[3.2.1]oct-3-ylidene]-9H-thioxanthene-3-carboxylic acid diethylamide, 13h Following Procedure 11, substituting compound 9h for compound 10a, and substituting 2-iodoethanol for allyl bromide, compound 13h was obtained. MS m/z (MH+)=449.2. $^1$H NMR 300 MHz (CDCl$_3$) δ 1.05-1.4 (m, 8H), 1.8 (m, 2H), 2.6-2.8 (m, 4H), 3.0 (m, 2H), 3.5 (m, 4H), 3.80 (m, 2H), 4.8 (br s, 1H), 7.2 (m, 5H), 7.5 (m, 2H).

Procedure 25

The (+) and (−) enantiomers of compound 24 (compounds 52 and 53), in Table 1 herein were separated on a preparative chiralpak AD column (500 grams of 20 micron material, 5×41 cm) using hexane/methanol/ethanol (50/25/25) as eluent. The analytes were monitored using a wavelength of 220 nm. For analytical work, the same column material was used (chiralpak AD, 4.6×50 mm), and the same solvents, but in a 80/10/10 proportion.

The (+) and (−) enantiomers of compound 54 (compounds 55 and 56), in Table 1 herein were separated on a preparative Chiralpak AD column (500 grams of 20 micron material, 50×41 cm) using heptane/ethanol (85/15) as eluent. The analytes were monitored using a wavelength of 220 nm.

Example I

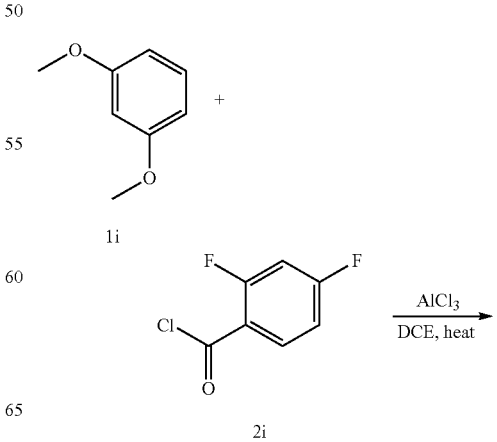

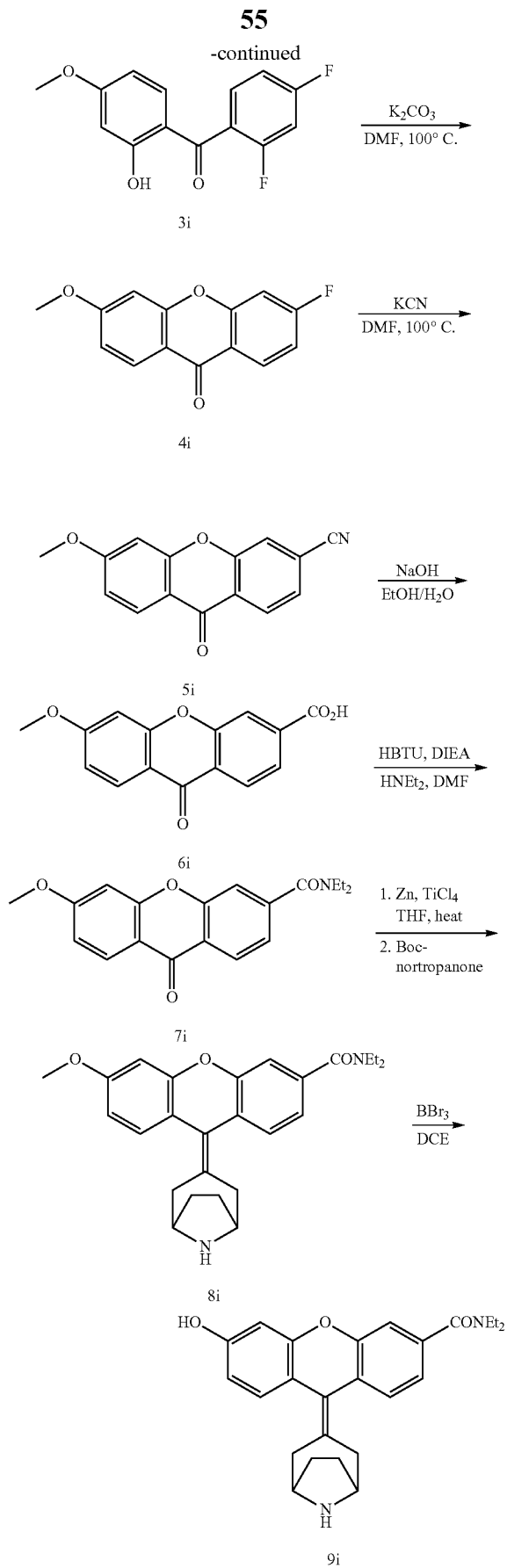

Procedure 26

(2,4-Difluoro-phenyl)-(2-hydroxy-4-methoxy-phenyl)-methanone, 3i

Aluminum chloride (2.03 g, 15.2 mmol) was added in portions to a solution of 1,3-dimethoxybenzene (1.86 mL, 15.2 mmol) and 2,4-difluorobenzoyl chloride (1.86 mL, 15.2 mmol) in 1,2-dichloroethane at 0° C. The mixture was allowed to warm to rt over 3 h then heated at reflux for 6 h. The resultant mixture was allowed to cool to rt, then poured into a mixture of ice (~100 g) and concentrated hydrochloric acid (~20 mL). The organic layer was separated. The aqueous solution was stirred at ambient temperature overnight, and extracted with dichloromethane. The organic layers were washed with aqueous sodium bicarbonate and dried over magnesium sulfate. The solvents were evaporated in vacuo to give crude product. A portion of the product was purified by flash chromatography on silica gel, using a gradient of 1%-10% EtOAc/heptane as the eluent to give the title compound 3i (1.8 g). MS: m/z 264.9 (MH+). $^1$H NMR (CDCl$_3$): δ 3.90 (s, 3H), 6.42 (d of d, 1H, J=9.0 and 2.5 Hz), 6.50 (d, 1H, J=2.5 Hz), 6.91-7.04 (m, 2H), 7.27-7.29 (m, 1H), 7.44-7.50 (m, 1H) and 12.44 (s, 1H).

Procedure 27

3-Fluoro-6-methoxy-xanthen-9-one, 4l

A mixture of potassium carbonate (2.13 g, 15.4 mmol) and (2,4-difluoro-phenyl)-(2-hydroxy-4-methoxy-phenyl)-methanone (3.4 g, 12.9 mmol) in N,N-dimethylformamide (50 mL) was heated at 100° C. for 2 h. The mixture was cooled and poured into water (~150 mL). A solid was collected by filtration, washed with water, and dried in vacuo to give the title compound (2.8 g), which was used without purification in the subsequent step. MS: m/z 244.9 (MH+). $^1$H NMR (CDCl$_3$): δ 3.94 (s, 1H), 6.88 (d, 1H, J=2.4 Hz), 6.96 (d of d, 1H, J=2.4 & 8.9 Hz), 7.07 (m, 2H), 8.24 (d, 1H, 8.9 Hz) and 8.34 (d of d, 1H, J=6.5 & 8.8 Hz).

Procedure 28

6-Methoxy-9-oxo-9H-xanthene-3-carbonitrile, 5l

A mixture of finely ground sodium cyanide (1.3 g, 26.5 mmol) and 3-fluoro-6-methoxy-xanthen-9-one (2.3 g, 9.42 mmol) in N,N-dimethylformamide (30 mL) was heated at 100° C. for 4 hours. Sodium cyanide (0.7 g, 14.3 mmol) was added and heating continued an additional hour. The mixture was allowed to cool to room temperature, then poured into ice water (~150 mL). The product was collected by filtration, washed with water and air dried to give Compound 5i, 1.42 g (60%). MS: m/z 251.9 (MH+). $^1$H NMR (CDCl$_3$): δ 3.96 (s, 3H), 6.91 (d, 1H, J=2.3 Hz), 7.00 (d of d, 1H, J=2.3 & 8.9 Hz), 7.61 (d of d, 1H, J=1 & 8.1 Hz), 7.79 (d, 1H, J=1 Hz), 8.24 (d, 1H, J=8.9 Hz) and 8.42 (d, 1 H, J=8.1 Hz).

6-Methoxy-9-oxo-9H-xanthene-3-carboxylic acid, 6l

Using the method described in Procedure 2, substituting compound 5l for compound 1a, the title compound was prepared (0.75 g). MS: m/z 270.9 (MH+). $^1$H NMR (DMSO-d$_6$): δ 3.95 (s, 3H), 7.06 (d of d, 1H, 2.4 & 8.9 Hz), 7.17 (d, 1H, J=2.4 Hz), 7.94 (d of d, 1H, J=1.4 & 8.2 Hz), 8.03 (d, 1H, J=1.4 Hz), 8.10 (d, 1H, J=8.9 Hz), 8.24 (d, 1H, J=8.2 Hz) and 13.65 (br s, 1H).

Procedure 29

6-Methoxy-9-oxo-9H-xanthene-3-carboxylic acid diethylamide, 7i

A mixture of compound 6i (0.707 g, 2.62 mmol) and O-benzotriazol-yl-N,N,N',N'-tetramethyluronium hexafluorophosphate (HBTU, 1.05 g, 2.74 mmol) in N,N-dimethylformamide (10 mL) was treated with N,N-diisopropylethylamine (DIEA, 0.685 mL, 3.92 mmol) and allowed to stir at rt for 15 min. Diethylamine (0.541 mL, 5.23 mL) was added and the resultant mixture was stirred for 2 h. The mixture was poured into ice water. A solid was collected by filtration, washed with water and air dried to give the title compound (0.445 g). MS: m/z 326.0 (MH$^+$). $^1$H NMR (DMSO-d$_6$): δ 1.07 (br t, 3H), 1.19 (br t, 3H), 3.20 (br q, 2H), 3.48 (br t, 2H), 3.95 (s, 3H), 7.08 (m, 1H), 7.17 (d, 1H, J=2.1 Hz), 7.40 (d of d, 1H, J=1.3 & 8.1 Hz), 7.59 (d, 1H, J=1.2 Hz), 8.12 (d of d, 1H, J=1.3 & 8.9 Hz) and 8.21 (d, 1H, J=8.1 Hz).

Procedure 30

9-(8-Aza-bicyclo[3.2.1]oct-3-ylidene)-6-methoxy-9H-xanthene-3-carboxylic acid diethylamide, 8i A suspension of zinc powder (0.626 g, 9.60 mmol) in THF (20 mL), at 0° C. was treated with titanium(IV)chloride (0.525 mL, 4.79 mmol), by dropwise addition. The resultant mixture was heated at reflux for 2 h. The resultant solution was cooled to room temperature, and 3-oxo-8-aza-bicyclo[3.2.1]octane-8-carboxylic acid tert-butyl ester (0.270 g, 1.20 mmol) and compound 7i (0.390, 1.20 mmol) were added and the solution was heated at reflux for 2 h. Potassium sodium tartrate (2.98 g, 10 56 mmol), dissolved in a minimal amount of water, was added to the reaction mixture and allowed to stir at ambient temperature overnight. The inorganic solids were removed by filtration and washed generously with THF. The solvent was evaporated in vacuo, and the residue was partitioned between dichloromethane and 10% aqueous ammonium hydroxide. The organic layer was separated and dried over sodium sulfate. The solvent was evaporated in vacuo. The residue was taken up in DMSO and purified by reverse phase preparative HPLC(C$_{18}$), using a gradient of acetonitrile (10% to 90%) in water with TFA (0.1%), to give the title compound as its trifluoroacetic acid salt (0.50 g). MS: m/z 419.1 (MH$^+$). $^1$H NMR (DMSO-d$_6$): δ 1.0-1.2 (br m, 6H), 1.32 (br d, 2H), 1.78 (br m, 2H), 2.85-3.02 (br m, 4H), 3.2-3.55 (br m, 4H), 3.80 (s, 3H), 3.96-4.05 (br s, 2H), 6.81 (d of d, 1H, J=2.5 & 8.6), 6.88 (d, 1H, J=2.5 Hz), 7.15 (d of d, 1H, J=1.4 & 7.8 Hz), 7.20 (d, 1H, J=1.4 Hz), 7.31 (d, 1H, J=8.6 Hz), 7.41 (d, 1H, J=7.8 hZ), 8.81 br s, 1H) and 9.12 (br d, 1H).

Procedure 31

9-(8-Aza-bicyclo[3.2.1]oct-3-ylidene)-6-hydroxy-9H-xanthene-3-carboxylic acid diethylamide, 9i A 1.0 M solution of boron tribromide in dichloromethane (2.14 mL, 2.14 mmol) was added to a solution of the trifluoroacetic acid salt of 9-(8-aza-bicyclo[3.2.1]oct-3-ylidene)-6-methoxy-9H-xanthene-3-carboxylic acid diethylamide (0.285 g, 0.535 mmol) in dichloromethane (10 mL) at 0° C.

The resultant mixture was stirred at room temperature for 2 h. The mixture was cooled to 0° C., and treated with 10% aqueous ammonium hydroxide (~20 mL). The organic layer was separated and the aqueous layer was extracted with dichloromethane. The combined organic layers were washed with brine and dried over sodium sulfate. The solvent was evaporated in vacuo, and the residues was dissolved in DMSO and applied to reverse phase C$_{18}$ column for purification via HPLC, using a gradient of acetonitrile (10% to 90%) in water with trifluoroacetic acid (0.1%) as the eluant. Fractions containing the title compound were combined and further purified via reverse phase HPLC to give the purified title compound (0.035 g). MS: m/z 405.1 (MH$^+$). $^1$H NMR (DMSO-d$_6$): δ 1.0-1.2 (br m, 6H), 1.29 (d, 12H, J=8.1 Hz), 1.7-1.8 (br m, 2H), 2.8-3.0 (br m, 4H), 3.1-3.5 (br m, 4H), 3.99 (br s, 2H), 6.63-6.65 (m, 2H), 7.13 (d, 1 H, J=7.9 Hz), 7.18-7.21 (m, 3H), 7.41 (d, 1H, J=7.9 Hz), 8.70 (br s, 1H), 9.01 br d, 1H) and 9.93 (br s 1H).

Example J

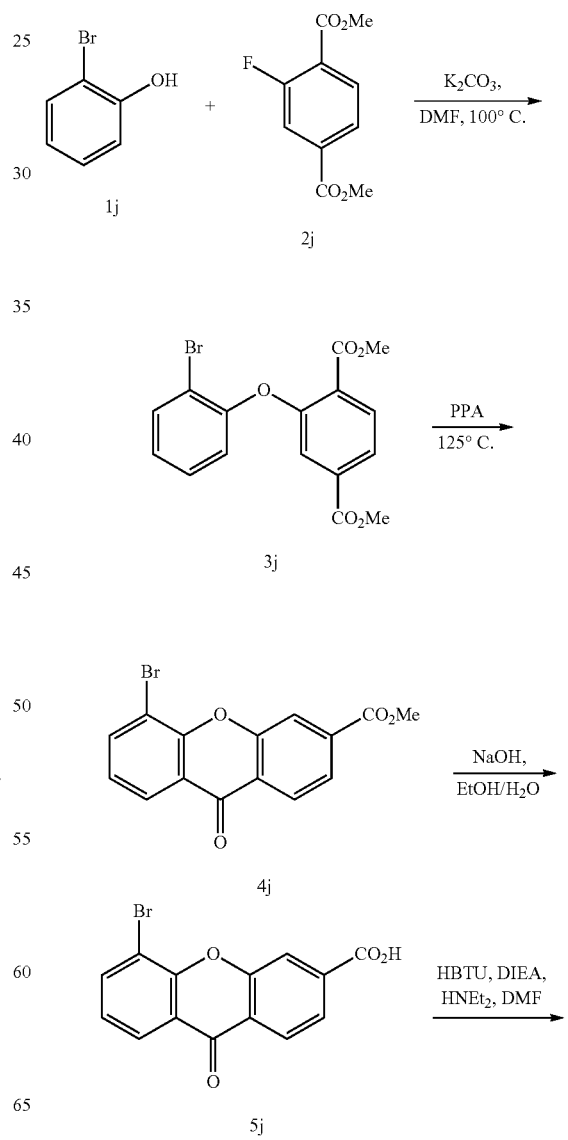

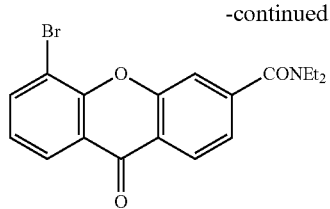

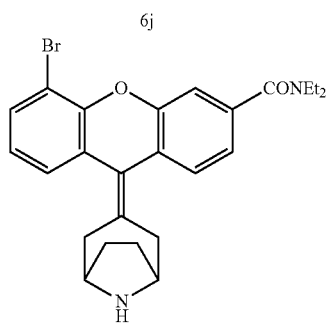

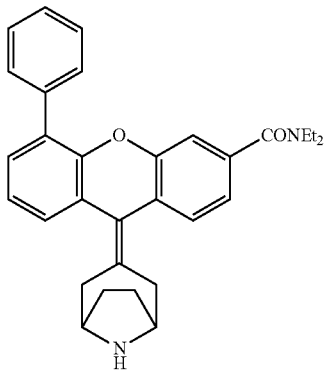

Procedure 32

2-(2-Bromo-phenoxy)-terephthalic acid dimethyl ester, 3j

A mixture of 2-fluoro-terephthalic acid dimethyl ester 2j (10 g, 47.1 mmol), 2-bromophenol 1j (6.0 mL, 51.8 mmol) and potassium carbonate (7.16 g, 51.8 mmol) in N,N-dimethylformamide (100 mL) was heated at 100° C. for 36 h. The mixture was allowed to cool to rt, then poured into cold dilute hydrochloric acid (0.5 N, 350 mL). The product was extracted into EtOAc, washed with water (4×) and brine (1×) and dried over magnesium sulfate. The solvent was evaporated in vacuo, and the residue was purified by flash chromatography on silica gel using dichloromethane as the eluant. The crude product was isolated (10.5 g) and used without further purification in the subsequent reaction. MS: m/z 365 (MH+).

Procedure 33

5-Bromo-9-oxo-9H-xanthene-3-carboxylic acid, 5j (via 4j)

2-(2-Bromo-phenoxy)-terephthalic acid dimethyl ester (10 g) was added dropwise to hot (100° C.) polyphosphoric acid (280 g) over 5 min. The solution was heat at 155° C. for 2 h at which point the heating was continued at 180° C. for an additional 2 h. The solution was mixed with a large volume of ice water. The resultant solids were collected by filtration, washed with water and purified by flash chromatography on silica gel, using a gradient of methanol (1% to 10%) in dichloromethane with acetic acid (0.1%) to give compound 4j (1.25 g). The acid compound 5j was isolated from the latter fractions (3.52 g).

A solution of the ester compound 4j (1.25 g, 3.75 mmol) and 3 N sodium hydroxide (1.37 mL, 4.12 mmol) in MeOH (30 mL) was heated at reflux for 2 h. The solution was cooled to rt and made acidic with 2 N hydrochloric acid (~2.5 mL). The mixture was concentrated in vacuo, and then diluted with water. The resultant solid was collected by filtration, washed with water and air dried to yield an additional 1.08 g of compound 5j. MS: m/z 318.7 (MH+). $^1$H NMR (DMSO-d$_6$): δ 7.43 (t, 1H, J=7.8 Hz), 7.98 (d of d, 1H, J=1.4 & 8.2), 8.09 (d, 1 H, J=1.3 Hz), 8.17-8.23 (m, 2H) and 8.28 (d, 1H, J=8.2 Hz).

5-Bromo-9-oxo-9H-xanthene-3-carboxylic acid diethylamide, 6j

Using the method described in Procedure 29, substituting compound 5j for compound 6i, the title compound was prepared. Subsequent purification by flash chromatography, using dichloromethane as the eluant gave Compound 6j (4.4 g). MS: m/z 373.8 (MH+). $^1$H NMR (CDCl$_3$): δ 1.16 (t, 3H, J=6.8 Hz), 1.30 (t, 3H, J=6.8 Hz), 3.28 (q, 2H, J=6.8 Hz), 3.60 (q, 2H, J=6.8 Hz), 7.30 (d, 1H, J=7.9 Hz), 7.40 (d of d, 1H, J=1.4 & 8.0 Hz), 7.64 (d, 1H, J=1.4 Hz), 7.98 (d of d, 1H, J=1.6 & 7.9 Hz), 8.30 (d of d, 1H, J=1.6 & 8.0 Hz) and 8.36 (d, 1H, J=8.1 Hz).

Procedure 34

9-(8-Aza-bicyclo[3.2.1]oct-3-ylidene)-5-bromo-9H-xanthene-3-carboxylic acid diethylamide, 7j A suspension of zinc powder (5.59 g, 85.5 mmol) in tetrahydrofuran (THF, 100 mL) at 0° C., was treated with titanium(IV)chloride (4.69 mL, 42.8 mmol) by dropwise addition. The resultant mixture was heated at reflux for 2 h. The resultant solution was cooled to 0° C. 3-oxo-8-aza-bicyclo [3.2.1]octane-8-carboxylic acid tert-butyl ester (2.4 g, 10.7 mmol) and 5-bromo-9-oxo-9H-xanthene-3-carboxylic acid diethylamide (4.0 g, 10.7 mmol) were added and the solution was heated at reflux for 4 h. Potassium sodium tartrate tetrahydrate (30 g, 106 mmol) was added to the reaction mixture and allowed to stir at ambient temperature overnight. The inorganic solids were removed by filtration and washed successively with THF, EtOAc and dichloromethane. The solvent was evaporated in vacuo. Purification by flash chromatography using a gradient 1% to 10% methanol (with ammonia, 2 N) in dichloromethane as the eluent gave Compound 7j (3.65 g). Crude product was purified by reverse phase preparative HPLC, using a gradient of acetonitrile (10% to 90%) in water with trifluoroacetic acid (0.1%), to give the trifluoroacetic acid salt of compound 7j. MS: m/z 467.0 (MH+). $^1$H NMR (DMSO-d$_6$): δ 1.0-1.2 (br m, 6 H), 1.32 (d, 2H, J=7.9 Hz), 1.75-1.85 (br m, 2H), 2.85-3.10 (m, 4H), 3.15-3.50 (br m, 4H), 4.01 br s, 2H), 7.15-7.26 (m, 3H), 7.42 (d, 1H, J=6.7 Hz), 7.49 (d, 1H, J=7.9 Hz), 7.66 (d, 1H, J=7.9 Hz), 8.81 (br s, 1H) and 9.12 br d, 1H).

Procedure 35

9-(8-Aza-bicyclo[3.2.1]oct-3-ylidene)-5-phenyl-9H-xanthene-3-carboxylic acid diethylamide, 8j A mixture of 9-(8-aza-bicyclo[3.2.1]oct-3-ylidene)-5-bromo-9H-xanthene-3-carboxylic acid diethylamide (0.170, 0.363 mmol), phenylboronic acid (0.049 g, 0.40 mmol) and cesium carbonate (0.236 g, 0.726 mmol) in dioxane (4 mL) and ethanol (1 mL) was treated with dichloro[1,1'-bis(diphenylphosphino)ferrocene]palladium (II) dichloromethane adduct (13 mg), and the resulting mixture was heated at reflux for 2 h. The reaction mixture was cooled to room temperature, and the inorganics removed by filtration and washed successively with dioxane, ethanol and dichloromethane. The solvents were evaporated in vacuo. The residue was purified by reverse phase ($C_{18}$) preparative HPLC, using a gradient of acetonitrile (10% to 90%) in water with trifluoroacetate (0.1%) as the eluant to give the title compound (0.153 g) as a colorless solid. MS: m/z 465.3 ($MH^+$). $^1$H NMR (DMSO-$d_6$): δ 1.05-1.20 (br m, 6H0, 1.31 d, 2H, J=8.2 Hz), 1.75-1.85 (br m, 2H), 2.90-3.10 (m, 4H), 3.15-3.50 (br m, 4H), 4.03 br s, 2H), 7.10 (d, 1H, J=1.5 Hz), 7.20 (d of d, 1H, J=1.5 & 7.9 Hz), 7.32 (t, 1H, J=7.5 Hz), 7.40-7.63 (m, 8H), 8.83 (br s, 1H0 and 9.16 (br d, 1H).

9-(8-Aza-bicyclo[3.2.1]oct-3-ylidene)-5-methoxy-9H-xanthene-3-carboxylic acid diethylamide The title compound was prepared following Example J and substituting 2-methoxyphenol for 2-bromophenol in Procedure 32. MS: m/z 419.1 ($MH^+$). $^1$H NMR (DMSO-$d_6$): δ 1.0-1.2 (m, 6H), 1.29 (br m, 1H), 1.73-1.82 (m, 2H), 2.87-3.15 (m, 4H), 3.22 (br m, 2H), 3.42 (br m, 2H), 3.88 (s, 3H), 4.00 (br s, 2H), 6.95 (d, J=7.5 Hz, 1H), 7.07-7.19 (m, 3H), 7.22 (d, J=1.5 Hz, 1H), 7.44 (d, J=7.9 Hz, 1H), 8.77 (br s, 1H) and 9.08 (br s, 1H).

9-(8-Aza-bicyclo[3.2.1]oct-3-ylidene)-5-hydroxy-9H-xanthene-3-carboxylic acid diethylamide The title compound was prepared from 9-(8-aza-bicyclo[3.2.1]oct-3-ylidene)-5-methoxy-9H-xanthene-3-carboxylic acid diethylamide using an adaptation of Procedure 31. MS: m/z 405.0 ($MH^+$). $^1$H NMR (DMSO-$d_6$): δ 1.0-1.2 (m, 6H), 1.29 (br m, 1H), 1.73-1.84 (m, 2H), 2.95-3.15 (m, 4H), 3.20 (br m, 2H), 3.42 (br m, 2H), 4.00 (br s, 2H), 6.80 (d, J=7.6 Hz, 1H), 6.87 (d, J=7.9 Hz, 1H), 7.02 (t, J=7.9 Hz, 1H), 7.15 (d of d, J=1.5 & 7.9 Hz, 1H), 7.25 (d, J=1.5 Hz, 1H), 7.42 (d, J=7.9 Hz, 1H), 8.78 (br s, 1H), 9.08 (br s, 1H) and 9.67 (br s, 1H).

9-(8-Aza-bicyclo[3.2.1]oct-3-ylidene)-5-pyridin-4-yl-9H-xanthene-3-carboxylic acid diethylamide The title compound was prepared following the method described in Example J and substituting pyridin-4-yl boronic acid for phenyl boronic acid in Procedure 35. MS: m/z 466.1 ($MH^+$). $^1$H NMR (DMSO-$d_6$): δ 1.0-1.2 (m, 6H), 1.32 (br m, 2H), 1.80 (br m, 2H), 2.88-3.42 (br m, 8H), 4.03 (br s, 2H), 7.22 (d, J=7.8 Hz, 1H), 7.27 (d, J=1.2 Hz, 1H), 7.42 (t, J=7.6 Hz, 1H), 7.51 (d, J=7.8 Hz, 1H), 7.58 (d, J=7.6 Hz, 1H), 7.63 (d, J=6.8 Hz, 1H), 8.06 (d, J=6.1 Hz, 2H), 8.90 (br m, 3H) and 9.22 (br d, J=9.4 Hz, 1H).

9-(8-Aza-bicyclo[3.2.1]oct-3-ylidene)-5-furan-3-yl-9H-xanthene-3-carboxylic acid diethylamide The title compound was prepared using the method described in Example J, substituting furan-3-yl boronic acid for phenyl boronic acid in Procedure 35. MS: m/z 455.1 ($MH^+$). $^1$H NMR (DMSO-$d_6$): δ 1.0-1.2 (m, 6H), 1.30 (br m, 2H), 1.78 (br m, 2H), 2.89-3.05 (m, 4H), 3.20 (br m, 2H), 3.44 (br m, 2H), 4.02 (br s, 2H), 7.15 (s, 1H), 7.19 (d, J=7.8 Hz, 1H), 7.26-7.31 (m, 2H), 7.47 (d, J=7.8 Hz, 1H), 7.56 (d, J=1.1 Hz, 1H), 7.69-7.72 (m, 1H), 7.82 (s, 1H), 8.59 (s, 1H), 8.83 (br d, 1H) and 9.15 (br d, J=9.3 Hz, 1H).

9-(8-Aza-bicyclo[3.2.1]oct-3-ylidene)-5-pyridin-3-yl-9H-xanthene-3-carboxylic acid diethylamide The title compound was prepared using the method described in Example J, substituting pyridin-3-yl boronic acid for phenyl boronic acid in Procedure 35. MS: m/z 466.1 ($MH^+$). $^1$H NMR (DMSO-$d_6$): δ 1.0-1.2 (m, 6H), 1.32 (m, 2H), 1.80 (br m, 2H), 2.90-3.02 (m, 4H), 3.20 (br m, 2H), 3.42 (br m, 2H), 4.03 (br s, 2H), 7.16 (d, J=1.5 Hz, 1H), 7.20 (d of d, J=1.5 & 7.8 Hz, 1H), 7.38 (t, J=7.7 Hz, 1H), 7.49-7.56 (m, 3H), 7.76 (d of d, J=5.0 & 7.9 Hz, 1H), 8.31 (d, J=8.0 Hz, 1H), 8.74 (d of d, J=1.5 & 5.0 Hz, 1H), 8.82 (br s, 1H), 8.95 (s, 1H) and 9.13 (br d, 1H).

9-(8-Aza-bicyclo[3.2.1]oct-3-ylidene)-5-thiophen-3-yl-9H-xanthene-3-carboxylic acid diethylamide The title compound was prepared using the method described in Example J, substituting thiophen-3-yl boronic acid for phenyl boronic acid in Procedure 35. MS: m/z 471.0 ($MH^+$). $^1$H NMR (DMSO-$d_6$): δ 1.0-1.2 (m, 6H), 1.31 (m, 2H), 1.78 (br m, 2H), 2.95-3.05 (m, 4H), 3.21 (br m, 2H), 3.43 (br m, 2H), 4.02 (br s, 2H), 7.21 (d of d, J=1.5 and 7.8 Hz, 1H), 7.28 (t, J=7.6 Hz, 1H), 7.34 (d of d, J=1.4 & 7.6 Hz, 1H), 7.38 (d, J=1.4 Hz, 1H), 7.48 (d, J=7.8 Hz, 1H), 7.63-7.70 (m, 3H), 8.13 (d of d, J=1.4 & 2.8 Hz, 1H), 8.80 (br s, 1H) and 9.12 (br d, J=10 Hz, 1H).

Example K 9-(8-Aza-bicyclo[3.2.1]oct-3-ylidene)-9H-xanthene-3-carboxylic acid isopropyl-methyl-amide Procedure 36

2-Phenoxy-terephthalic acid dimethyl ester. 2-Iodo-terephthalic acid dimethyl ester (10 g, 31 mmol), phenol (3.23 g, 34 mmol), tetrakis-acetonitrilecopper hexafluorophosphate (2.9 g, 7.8 mmol), and cesium carbonate (10.2 g, 31 mmol) were added to a 1 L 3-neck round bottom flask equipped with a mechanical stirrer, a reflux condenser and containing toluene (350 mL). The reaction was refluxed 5 h under nitrogen with stirring. After cooling, EtOAc (200 mL) was added and the mixture was filtered. The filtrate was concentrated to afford the crude title compound (9.2 g) that was used without purification.

2-Phenoxy-terephthalic acid dimethyl ester was converted to 9-Oxo-9H-xanthene-3-carboxylic acid using an adaptation of Procedure 33.

9-Oxo-9H-xanthene-3-carboxylic acid-N-isopropyl-N-methyl-amide was prepared from 9-Oxo-9H-xanthene-3-carboxylic acid using an adaptation of Procedure 29 and substituting N-isopropyl-N-methyl-amine for diethylamine.

The title compound of Example K was prepared by the method described in Procedure 34, substituting 9-Oxo-9H-xanthene-3-carboxylic acid N-isopropyl-N-methyl-amide for compound 6j. The crude product was purified by preparative reverse phase chromatography on a C-18 column, eluting with water/acetonitrile/0.1% TFA to yield the product as its trifluoroacetic acid salt. MS m/z (MH$^+$) 389.2; $^1$H NMR 300 MHz (DMSO-$d_6$) δ 1.12 (s, 6H), 1.2-1.3 (m, 2H), 1.79 (m, 2H), 2.82 (m, 3H), 2.95 (q, 4H), 4.00 (s, 2H), 7.18-7.21 (m, 1H), 7.24 (d, 2H), 7.30 (d, 1H), 7.36 (d, 1H), 7.40-7.46 (m, 2H), 8.77 (m, 1H), 9.09 (d, 1H).

Compounds 1 through 102 in the table, below, were synthesized using the procedures described above.

TABLE 1

| Cpd | R$_1$ | R$_2$ | R$_3$ | R$_4$ | R$_5$ | A | Y | Z |
|---|---|---|---|---|---|---|---|---|
| 1 | Et | Et | Me | H | H | absent | CH$_2$O | O |
| 2 | Et | Et | H | H | H | absent | CH$_2$O | O |
| 3 | Et | Et | H | H | H | absent | O | O |
| 4 | Et | Et | Benzo[1,3]dioxol-5-ylmethyl | H | H | absent | CH$_2$O | O |
| 5 | Et | Et | Phenethyl | H | H | absent | CH$_2$O | O |
| 6 | Et | Et | Allyl | H | H | absent | CH$_2$O | O |
| 7 | Et | Et | Me | H | H | absent | O | O |
| 8 | Et | Et | Allyl | H | H | absent | O | O |
| 9 | Et | H | Me | H | H | absent | CH$_2$O | O |
| 10 | Et | H | 1,1,1-Trichloroethoxycarbonyl | H | H | absent | CH$_2$O | O |
| 11 | Et | H | H | H | H | absent | CH$_2$O | O |
| 12 | Et | H | 2-Methyl-but-2-enyl | H | H | absent | CH$_2$O | O |
| 13 | Et | H | Thiophen-2-yl methyl | H | H | absent | CH$_2$O | O |
| 14 | Et | H | 2-Methyl-allyl | H | H | absent | CH$_2$O | O |
| 15 | Et | H | Cyclopropylmethyl | H | H | absent | CH$_2$O | O |
| 16 | Et | H | Pyridin-2-ylmethyl | H | H | absent | CH$_2$O | O |
| 17 | Et | H | 1-H-Imidazol-4-yl methyl | H | H | absent | CH$_2$O | O |
| 18 | Et | H | 4-Hydroxy-3-methoxyphenyl-methyl | H | H | absent | CH$_2$O | O |
| 19 | Et | H | Allyl | H | H | absent | CH$_2$O | O |
| 20 | Et | H | Phenethyl | H | H | absent | CH$_2$O | O |
| 22 | Et | Et | Phenethyl | H | H | absent | O | O |
| 23 | Et | Et | Me | H | H | CH$_2$CH$_2$ | O | O |
| 24 | Et | Et | H | H | H | CH$_2$CH$_2$ | O | O |
| 25 | Et | Et | Furan-3-ylmethyl | H | H | CH$_2$CH$_2$ | O | O |
| 26 | Et | H | Phenethyl | H | H | CH$_2$CH$_2$ | CH$_2$O | O |
| 27 | Et | H | Phenethyl | H | H | CH$_2$CH$_2$ | O | O |
| 28 | Et | Et | Furan-3-ylmethyl | H | H | absent | O | O |
| 29 | Et | Et | Pyridin-2-ylmethyl | H | H | absent | O | O |
| 30 | Et | Et | 2-Hydroxyphenyl-methyl | H | H | absent | O | O |
| 31 | Et | Et | Carbamimidoyl | H | H | absent | O | O |
| 32 | Et | H | H | H | H | absent | O | O |
| 33 | Et | Et | 1-Prop-2-ynyl | H | H | absent | O | O |
| 34 | Et | Et | H | Acetyl-amino | H | absent | O | O |
| 35 | Et | Et | Hydroxy-ethyl | H | H | absent | O | O |
| 36 | Et | Et | Phenyliminomethyl | H | H | absent | O | O |
| 37 | Et | Et | Thioformyl | H | H | absent | O | O |
| 38 | Et | Et | Allyl | H | H | CH$_2$CH$_2$ | O | O |
| 39 | Et | Et | 2-Methoxy-ethyl | H | H | CH$_2$CH$_2$ | O | O |
| 40 | Et | Et | Methylthioethyl | H | H | CH$_2$CH$_2$ | O | O |
| 41 | Et | Et | Methyl | Acetyl-amino | H | absent | O | O |
| 42 | Et | Et | H | H | H | absent | O | O |
| 43 | Et | Et | Me | H | H | absent | O | O |
| 44 | Et | Et | Pyridin-2-ylmethyl | H | H | CH$_2$CH$_2$ | O | O |
| 45 | Et | Et | Hydroxyethyl | H | H | CH$_2$CH$_2$ | O | O |
| 46 | Et | Et | 1-H-Imidazol-4-yl methyl | H | H | CH$_2$CH$_2$ | O | O |
| 47 | Et | Et | Benzo[1,3]dioxol-5-ylmethyl | H | H | CH$_2$CH$_2$ | S | O |
| 48 | Et | Et | H | H | H | CH$_2$CH$_2$ | S | O |
| 49 | Et | Et | Cyclopropylmethyl | H | H | CH$_2$CH$_2$ | S | O |
| 50 | Et | Et | Methyllthiopropyl | H | H | CH$_2$CH$_2$ | S | O |
| 51 | Et | Et | Hydroxy-ethyl | H | H | CH$_2$CH$_2$ | S | O |
| 52 (−) enantiomer | Et | Et | H | H | H | CH$_2$CH$_2$ | O | O |
| 53 (+) enantiomer | Et | Et | H | H | H | CH$_2$CH$_2$ | O | O |
| 54 | Et | H | H | H | H | CH$_2$CH$_2$ | O | O |
| 55 (−) enantiomer | Et | H | H | H | H | CH$_2$CH$_2$ | O | O |
| 56 (+) enantiomer | Et | H | H | H | H | CH$_2$CH$_2$ | O | O |
| 57 | Me | Me | H | H | H | CH$_2$CH$_2$ | O | O |

TABLE 1-continued

| Cpd | $R_1$ | $R_2$ | $R_3$ | $R_4$ | $R_5$ | A | Y | Z |
|---|---|---|---|---|---|---|---|---|
| 58 | i-Pr | H | H | H | H | $CH_2CH_2$ | O | O |
| 59 | Me | i-Bu | H | H | H | $CH_2CH_2$ | O | O |
| 60 | n-Pr | n-Pr | H | H | H | $CH_2CH_2$ | O | O |
| 61 (+) enantiomer | Et | Et | H | H | H | $CH_2CH_2$ | S | O |
| 62 (−) enantiomer | Et | Et | H | H | H | $CH_2CH_2$ | S | O |
| 63 | n-Pr | H | H | H | H | $CH_2CH_2$ | O | O |
| 64 | Me | H | H | H | H | $CH_2CH_2$ | O | O |
| 65 | H | H | H | H | H | $CH_2CH_2$ | O | O |
| 66 | Et | Et | H | 6-methyl | H | $CH_2CH_2$ | O | O |
| 67 | Et | Et | H | 7-methyl | H | $CH_2CH_2$ | O | O |
| 68 | Et | Et | H | 5-methoxy | H | $CH_2CH_2$ | O | O |
| 69 | Et | Et | H | 7-Fluoro | H | $CH_2CH_2$ | O | O |
| 70 | Et | Et | H | 6-methoxy | H | $CH_2CH_2$ | O | O |
| 71 Enant. A | Et | Et | 1-H-imidazol-5-yl methyl | H | H | $CH_2CH_2$ | O | O |
| 72 Enant. B | Et | Et | 1-H-imidazol-5-yl methyl | H | H | $CH_2CH_2$ | O | O |
| 73 | Me | n-Bu | H | H | H | $CH_2CH_2$ | O | O |
| 74 | Et | Et | 1-H-imidazol-4-yl methyl | H | H | $CH_2CH_2$ | S | O |
| 75 | Et | Et | 1-H-imidazol-4-yl methyl | H | H | $CH_2CH_2$ | S | O |
| 76 | Et | Et | H | 6-hydroxy | H | $CH_2CH_2$ | O | O |
| 77 | Et | Et | H | 7-Methoxy | H | $CH_2CH_2$ | O | O |
| 78 | Et | H | Trifluoromethyl carbonyl | H | H | $CH_2CH_2$ | S | O |
| 79 | Et | H | Trifluoromethyl carbonyl | H | H | $CH_2CH_2$ | S | O |
| 80 | Et | H | H | H | H | $CH_2CH_2$ | S | O |
| 81 | Et | H | H | H | H | $CH_2CH_2$ | S | O |
| 82 | Et | Et | H | 7-hydroxy | H | $CH_2CH_2$ | O | O |
| 83 | Et | Et | H | 7-Bromo | H | $CH_2CH_2$ | O | O |
| 84 | Et | Et | H | 7-phenyl | H | $CH_2CH_2$ | O | O |
| 85 | Et | Et | H | 7-pyridin-4-yl | H | $CH_2CH_2$ | O | O |
| 86 | Et | Et | H | 7-furan-3-yl | H | $CH_2CH_2$ | O | O |
| 87 | Et | Et | H | 7-benzo thiophen-2-yl | H | $CH_2CH_2$ | O | O |
| 88 | Et | Et | H | N-t-Butoxy carbonyl pyrrol-2-yl | H | $CH_2CH_2$ | O | O |
| 89 | Et | Et | H | 7-pyridin-3-yl | H | $CH_2CH_2$ | O | O |
| 90 | Et | Et | H | 7-thiophen-3-yl | H | $CH_2CH_2$ | O | O |
| 91 | Et | Et | H | 7-(3,5-dimethyl) isoxazol-4-yl | H | $CH_2CH_2$ | O | O |
| 92 | Me | i-Pr | H | H | H | $CH_2CH_2$ | O | O |
| 93 | Et | Et | H | 7-pyrrol-2-yl | H | $CH_2CH_2$ | O | O |
| 94 | Et | Et | H | 5-bromo | H | $CH_2CH_2$ | O | O |
| 95 | Et | Et | H | 5-phenyl | H | $CH_2CH_2$ | O | O |
| 96 | Et | Et | H | 5-pyridin-4-yl | H | $CH_2CH_2$ | O | O |
| 97 | Et | Et | H | 5-furan-3-yl | H | $CH_2CH_2$ | O | O |
| 98 | Et | Et | H | 5-quinolin-3-yl | H | $CH_2CH_2$ | O | O |
| 99 | Et | Et | H | 5-thiophen-3-yl | H | $CH_2CH_2$ | O | O |
| 100 | Et | Et | H | 5-hydroxy | H | $CH_2CH_2$ | O | O |
| 101 | Et | Et | H | 5-pyridin-3-yl | H | $CH_2CH_2$ | O | O |
| 102 | Et | Et | H | 5-fluoro | H | $CH_2CH_2$ | O | O |

Biological Examples

Rat Brain Mu Opioid Receptor Binding Assay

Procedure: Male, Sprague Dawley (150-250 g, VAF, Charles River, Kingston, N.Y.) are killed by $CO_2$, and their brains removed and placed immediately in ice cold Tris HCl buffer (50 mM, pH 7.4). The forebrains are separated from the remainder of the brain by a coronal transection, beginning dorsally at the colliculi and passing ventrally through the midbrain-pontine junction. After dissection, the forebrains are homogenized in Tris buffer in a Teflon®-glass homogenizer. The homogenate is diluted to a concentration of 1 g of forebrain tissue per 80 mL Tris and centrifuged at 39,000×g for 10 min. The pellet is resuspended in the same volume of Tris buffer containing 5 mM $MgCl_2$ with several brief pulses from a Polytron homogenizer. This particulate preparation is used for the mu-opioid binding assays. Following incubation with the mu selective peptide ligand ~0.8 nM [$^3$H]DAMGO at 25° C. for 2.5 h in a 96-well plate with total 1 ml, the plate contents are filtered through Wallac filtermat B sheets on a Tomtec 96-well harvester. The filters are rinsed three times with 2 mL of 10 mM HEPES (pH7.4), and dried in a 650 W microwave oven for 1.75 min twice. To each sample area 2×40 μL of Betaplate Scint scintillation fluid (LKB) is added and analyzed on a LKB (Wallac) 1205 BetaPlate liquid scintillation counter.

Analysis: The data from the scintillation counter are used to calculate either the % inhibition compared to control binding (when only a single concentration of test compound is evaluated) or a $K_i$ value (when a range of concentrations is tested). % inhibition is calculated as: [(total dpm−test compound dpm)/(total dpm−nonspecific dpm)]*100. Kd and Ki values are calculated using GraphPad PRISM data analysis program.

[$^{35}$S]GTPγS Binding Assay in CHO-hμ Cell Membranes

Preparation of Membranes

CHO-hμ cell membranes are purchased from Receptor Biology, Inc. (Baltimore, Md.). About 10 mg/ml of membrane protein is suspended in 10 mM TRIS-HC pH 7.2, 2 mM EDTA, 10% sucrose.

Membranes are maintained at 4-8° C. 1 ml of membranes is added into 15 ml cold binding assay buffer. The assay buffer contains 50 mM HEPES, pH 7.6, 5 mM MgCl$_2$, 100 mM NaCl, 1 mM DTT and 1 mM EDTA. The membrane suspension is homogenized with a Polytron 2 times and centrifuged at 3000 rpm for 10 min. The supernatant is then centrifuged at 18,000 rpm for 20 min. The pellet is saved in a tube and 10 ml assay buffer is added to the tube. The pellet and buffer are mixed with a Polytron.

Incubation Procedure

The pellet membranes (20 μg/ml) are preincubated with SPA (10 mg/ml) at 25 C.° for 45 min in the assay buffer. The SPA (5 mg/ml) coupled with membranes (10 μg/ml) is then incubated with 0.5 nM [$^{35}$S]GTPgS in the same HEPES buffer containing 50 μM GDP in total volume of 200 μl. Increasing concentrations of receptor agonists are used to stimulate [$^{35}$S]GTPgS binding. The basal binding is tested in the absence of agonists and non-specific binding is tested in the present 10 μM unlabeled GTPγS. The data are analyzed on a Top counter.

Data

% of Basal=(stimulate−non-specific)*100/(basal−non specific).

% inhibition value values are calculated using a formula,

% Inhibition=(% Basal of 1 uM DAMGO−% Basal of compound)*100/(% Basal of 1 uM DAMGO−100)

[$^{35}$S]GTPγS Binding Assay in CHO-hδ Cell Membranes

Preparation of Membranes

CHO-hδ cell membranes are purchased from Receptor Biology, Inc. (Baltimore, Md.). 10 mg/ml of membrane protein is suspended in 10 mM TRIS-HC pH 7.2, 2 mM EDTA, 10% sucrose.

Membranes are maintained at 4-8° C. 1 ml of membranes is added into 15 ml cold binding assay buffer. The assay buffer contained 50 mM HEPES, pH 7.6, 5 mM MgCl$_2$, 100 mM NaCl, 1 mM DTT and 1 mM EDTA. The membrane suspension is homogenized with a Polytron 2 times and centrifuged at 3000 rpm for 10 min. The supernatant is then centrifuged at 18,000 rpm for 20 min. The pellet is saved in a tube and 10 ml assay buffer is added into the tube. The pellet and buffer are mixed with a Polytron.

Incubation Procedure

The pellet membranes (20 μg/ml) are preincubated with SPA (10 mg/ml) at 25 C.° for 45 min in the assay buffer. The SPA (5 mg/ml) coupled with membranes (10 μg/ml) is then incubated with 0.5 nM [$^{35}$S]GTPgS in the same HEPES buffer containing 50 μM GDP in total volume of 200 μl. Increasing concentrations of receptor agonists are used to stimulate [$^{35}$S]GTPgS binding. The basal binding is tested in the absence of agonists and non-specific binding is tested in the presence of 10 μM unlabeled GTP S. The data are analyzed on a Top counter.

[$^{35}$S]GTPγS Binding Assay in NG108-15 Cell Membrane

Preparation of Membranes

NG108-15 cell membranes were purchased from Applied Cell Sciences (Rockville, Md.). An 8 mg/mL portion of membrane protein was suspended in 10 mM TRIS-HC pH 7.2, 2 mM EDTA, 10% sucrose.

Membranes were maintained at 4-8° C. A 1 mL portion of membranes was added into 10 mL cold binding assay buffer. The assay buffer contained 50 mM Tris, pH 7.6, 5 mM MgCl$_2$, 100 mM NaCl, 1 mM DTT and 1 mM EGTA. The membrane suspension was homogenized with a Polytron for 2 times and centrifuged at 3000 rpm for 10 min. The supernatent was then centrifuged at 18,000 rpm for 20 min. The pellet was saved in a tube and 10 ml assay buffer was added into the tube. The pellet and buffer were mixed with a Polytron.

Incubation Procedure

The pellet membranes (75 μg/ml) were preincubated with SPA (10 mg/ml) at 25 C.° for 45 min in the assay buffer. The SPA (5 mg/ml) coupled with membranes (37.5 μg/ml) was then incubated with 0.1 nM [$^{35}$S]GTPγS in the same Tris buffer containing 100 μM GDP in total volume of 200 μl. Increasing concentrations of receptor agonists were used to stimulate [$^{35}$S]GTPγS binding. The basal binding was tested in the absent agonists and no specific binding was tested in the present 10 μM unlabeled GTPγS. The data were analyzed on a Top counter.

Data

% of Basal=(stimulate−non specific)*100/(basal−non specific).

EC50 values are calculated using a Prism program.

Mouse Abdominal Irritant Test

MAIT

The procedure used was that described by Collier et al. (1968), with minor modifications. Thirty minutes after the administration of test drug, the animals received an i.p. injection of 5.5 mg/kg of acetylcholine bromide. The mice were then placed into large glass animal jars and were continuously observed for the first occurrence of a characteristic behavioral response (twisting and elongation of the body which extends throughout the hindlimbs) within the specified observation period of 10 minutes. The percent of inhibition of this response was calculated as follows:

% Inhibition=100×(Number of Nonresponders)/(Number of Animals in Group)

The estimated $ED_{50}$ value (the dose of agonist calculated to produce 50% antinociception) and the corresponding 95% fiducial intervals were determined using the probit analysis of Litchfield and Wilcoxon (1949).

Data

% of Basal=(stimulate−non-specific)*100/(basal−non-specific).

EC50 value values are calculated using a Prism program.

Rat Zymosan Radiant Heat Test

Following an overnight fast, rats were acclimated to test chambers, which have warm, glass bottoms. A radiant thermal stimulus (beam of light) was then focused on the plantar surface of each hind paw in turn, and an initial (baseline) response time to a thermal stimulus was recorded for each animal. The light stimulus was automatically shut off by a photoelectric relay when the foot moved or when the cut-off time was reached (20 seconds for radiant heat @ 5 Amps). Rats were injected with Zymosan A (100 μL at 25 mg/mL) subcutaneously into the sub-plantar tissue of the left hind paw to stimulate an acute inflammatory reaction.

Three hours later, the response time of the animal to the thermal stimulus was then evaluated and compared to the animal's baseline response time. It was typically shorter, and this was recorded as percent hyperalgesia (% H). A cut-off value for % H (~75%) was used during analysis to ensure that the animals were hyperalgesic. Animals were then dosed with test drug or vehicle. At some time(s) later (typically 60 minutes), the response time of the animal to the thermal stimulus was again evaluated.

CFA Thermal Hyperalgesia

Intraplantar injection of Complete Freund's Adjuvant (CFA) in rodents results in a strong, long-lasting inflammatory reaction, characterized by a chronic and pronounced hyperalgesia to both thermal and mechanical stimuli. These effects peak between 24-72 hours following injection and can last for from several days to a few weeks. To assess the ability of JNJ compounds to reverse thermal hyperalgesia, male Sprague-Dawley rats (200-350 g) were given an intraplantar injection of CFA (1:1 CFA:saline, 100 μL) into their left hindpaw. Following a 24-hour incubation period, response latencies on the Radiant Heat Paw Stimulator (RH) were obtained and compared to baseline (pre-CFA) latencies. The response is automatically registered by the RH device when the rat lifts its paw from the surface of the glass. Only rats that exhibited at least a 25% reduction in response latency from baseline (i.e. hyperalgesia) were included in further analysis. Following the postCFA latency assessment, rats were dosed orally (2.5 mL/kg) with test compound or vehicle (hydroxypropylmethylcellulose, HPMC). Percent Reversal of hyperalgesia was calculated for each animal as (Treatment Response−postCFA Response)/(preCFA Response−postCFA Response)×100. Therefore, a return to normal pre-CFA thresholds was defined as 100% efficacy, whereas no change from post-CFA thresholds was 0% efficacy. Average % Reversal of hyperalgesia was then calculated for each treatment group (n=6-8 rats/group). Dose response curves were subsequently obtained at the time of peak effect. $ED_{50}$ values and associated statistics were calculated using PharmTools Plus software (The McCary Group).

Biological and Mass Spectral Data

TABLE 2

| Cmpd No. | rDOR Ki (nM) | rMOR Ki (nM) | hDOR GTPγS $EC_{50}$(nM) | hMOR GTPγS % I @10 μM | DOR GTPγS $EC_{50}$ (nM) | MAIT % I @ 150 μmol | Parent Peak obs | MS calcd |
|---|---|---|---|---|---|---|---|---|
| 1 | 25.5 | 6410 | >10,000 | | | 30.8 | 391.28 | 390.230 |
| 2 | 0.91 | 2630 | 58.6 | | | 100 | 377.24 | 376.215 |
| 3 | 0.95 | 6790 | 47.0 | 1.00 | | 50 | 363.22 | 362.199 |
| 4 | 0.39 | 301 | 552 | 9.00 | | 7.1 | 511.34 | 510.252 |
| 5 | 25.3 | 1290 | >10,000 | | | 40 | 481.35 | 480.278 |
| 6 | 4.25 | 7914.5 | 128 | | | 73.3 | 417.33 | 416.246 |
| 7 | 25.7 | 9190 | 1.400 | 1.00 | | 76.9 | 377.26 | 376.215 |
| 8 | 2.1 | 2820 | 620 | 1.00 | | 63.6 | 403.28 | 402.231 |
| 9 | >100000 | >100000 | | | | | 363.00 | 362.199 |
| 10 | >100000 | 92530 | | | | | 523.0 | 522.088 |
| 11 | 317.35 | 5659 | | | | | 349.0 | 348.184 |
| 12 | 271.25 | 1805.5 | | | | | 417.1 | 416.246 |
| 13 | 143.35 | 1902.5 | | | | | 445.1 | 444.187 |
| 14 | 432.45 | 4822.5 | | | | | 403.1 | 402.231 |
| 15 | 2043.5 | 4753 | | | | | 403.1 | 402.231 |
| 16 | 60.93 | 1145.5 | | | | | 440.1 | 439.226 |
| 17 | 218.5 | 2477 | | | | | 429.1 | 428.221 |
| 18 | 1997 | 2421.5 | | | | | 485.1 | 484.236 |
| 19 | 368.25 | 2873.5 | | | | | 389.1 | 388.215 |
| 20 | 23335 | 247.7 | | | | | 453.2 | 452.246 |
| 22 | 45.4 | 2130.0 | >10,000 | 2.00 | | | 467.33 | 466.262 |
| 23 | 48.38 | 5555.5 | 245 | | | | 403.2 | 402.231 |
| 24 | 0.57 | 5692.5 | 10.2 | 1.00 | | | 389.3 | 388.215 |
| 25 | 0.01 | 879.4 | 1.39 | 74.00 | | 30(@30) | 469.0 | 468.241 |
| 26 | 5479 | 15.62 | | 41.00 | | | 479.1 | 478.262 |
| 27 | 209 | 189 | | | | | 465.1 | 464.246 |
| 28 | 0.07 | 811 | 70.3 | 24.00 | | 40 | 443.1 | 442.226 |
| 29 | 0.05 | 362 | 31.6 | 34.00 | | 30 | 454.5 | 453.242 |
| 30 | 10.89 | 912 | 2,480 | 24.00 | | | 469.2 | 468.241 |
| 31 | 29.8 | 564 | 253 | 14.00 | | | 405.1 | 404.221 |
| 32 | 72.99 | 1493.75 | | | | | 335.4 | 334.168 |
| 33 | 16.53 | 5423.75 | | | | | 401.4 | 400.215 |
| 34 | >10000 | >10000 | | | | | 420.3 | 419.221 |
| 35 | 7.01 | >10000 | 271 | 17.00 | | | 407.0 | 406.226 |
| 36 | 0.79 | >10000 | 42.5 | 14.00 | | | 466.3 | 465.242 |

TABLE 2-continued

| Cmpd No. | rDOR Ki (nM) | rMOR Ki (nM) | hDOR GTPγS EC$_{50}$(nM) | hMOR GTPγS % I @10 μM | DOR GTPγS EC$_{50}$ (nM) | MAIT % I @ 150 μmol | Parent Peak obs | MS calcd |
|---|---|---|---|---|---|---|---|---|
| 37 | 2.02 | >10000 | 921 | 5.00 | | | 406.9 | 406.171 |
| 38 | 31.82 | 5518 | 342 | | | | 429.0 | 428.246 |
| 39 | 8.43 | 1682.5 | 94.9 | | | | 447.4 | 446.257 |
| 40 | 11.98 | >10000 | 267 | | | | 463.8 | 462.234 |
| 41 | 5198.15 | >10000 | | | | | 435.0 | 433.236 |
| 42 | 14.67 | 8792 | 266 | 4.00 | | | 364.9 | 364.22 |
| 43 | 10000 | >10000 | | | | | 379.2 | 378.231 |
| 44 | 0.15 | 77.17 | 0.873 | 28.00 | | | 480.3 | 479.13 |
| 45 | 4.57 | >100.00 | 14.3 | | | | 433.4 | 432.57 |
| 46 | 0.88 | >100.00 | 4.79 | | | | 468.60 | 468.60 |
| 47 | 4.5 | 48.30 | 125 | 59.23 | | | 539.4 | 538.71 |
| 48 | 0.90 | >100.00 | 18.8 | | | 66.7 | 405.4 | 404.58 |
| 49 | 25.0 | >100.00 | 252 | | | | 459.7 | 458.67 |
| 50 | 10.2 | >100.00 | 236 | | | | 493.5 | 492.75 |
| 51 | 4.85 | >100.00 | 62.8 | | | | 449.2 | 448.63 |
| 52 | 0.61 | >100.00 | 4.44 | | 66 | 50 | 389.3 | 388.22 |
| 53 | 50.09 | >100.00 | 257 | | 2059 | 60 | 389.3 | 388.22 |
| 54 | 68.45 | 715 | | | | 20 | 361.2 | 360.46 |
| 55 | 66.48 | 1855 | | | >1000 | 20 | 361.2 | 360.46 |
| 56 | 161.375 | 711.95 | | | | 40 | 361.2 | 360.46 |
| 57 | 396.67 | 5262 | | | | | 361.3 | 360.46 |
| 58 | 1160.2 | 2978 | | | | | 375.3 | 374.48 |
| 59 | 10.56 | 3336.5 | | | | | 403 | 402.54 |
| 60 | 4.621 | 835.8 | | | | | 416.9 | 416.57 |
| 61 | 133.3 | 7180 | | | 188 | 40 | 404.9 | 404.58 |
| 62 | 2.958 | 739.1 | | | 8.35 | 33.3 | 404.9 | 404.58 |
| 63 | 107.5 | 1729 | | | | | 375.2 | 374.48 |
| 64 | 117.635 | 711.4 | | | | | 347.1 | 346.43 |
| 65 | 197.345 | 857.7 | | | | | 333.1 | 332.40 |
| 66 | 3.1205 | 2954 | | | | | 403.2 | 402.54 |
| 67 | 54.39 | 10887 | | | | | 403.2 | 402.54 |
| 68 | 0.740 | 1294 | | | 22 | | 419.1 | 418.54 |
| 69 | 4.99 | 5830 | | | 126 | | 407.1 | 406.50 |
| 70 | 2.31 | 5742.5 | | | | | 419.1 | 418.54 |
| 71 Enant. A | 5.43 | 2771.5 | | | | | 468.9 | 468.60 |
| 72 Enant. B | 0.170 | 375.03 | | | | | 468.9 | 468.60 |
| 73 | 11.98 | 884 | | | 77.9 | | 403.4 | 402.54 |
| 74 | 3.79 | 848.15 | | | | | 485.0 | 484.67 |
| 75 | 0.122 | 200.34 | | | | | 485.0 | 484.67 |
| 76 | 1.70 | 284.5 | | | 5.91 | | 405.1 | 404.51 |
| 77 | 1023 | >10000 | | | | | 419.1 | 418.54 |
| 78 | | | | | | | 473 | 472.53 |
| 79 | | | | | | | 473.1 | 472.53 |
| 80 | 259.65 | 472.6 | | | | | 377.3 | 376.52 |
| 81 | 77.565 | 837.65 | | | | | 377.4 | 376.52 |
| 82 | 44.4 | 3098 | | | | | 405.0 | 404.51 |
| 83 | 138.56 | 17720 | | | | | 467 | 467.41 |
| 84 | 2890 | 37790 | | | | | 465.2 | 464.61 |
| 85 | 3004.5 | 10700 | | | | | 466.1 | 465.60 |
| 86 | 1755 | 12525 | | | | | 455.1 | 454.57 |
| 87 | 12060 | 29025 | | | | | 421.1 | 520.70 |
| 88 | 1082.5 | 15250 | | | | | 554.2 | 553.70 |
| 89 | 1953 | 18670 | | | | | 466.2 | 465.60 |
| 90 | 836.15 | 12360 | | | | | 471.1 | 470.64 |
| 91 | 1351.5 | 6702 | | | | | 484.1 | 483.61 |
| 92 | 2.0925 | 2.093 | | | 55.3 | | 389.2 | 388.51 |
| 93 | >10000 | >10000 | | | | | 454.4 | 453.59 |
| 94 | 2.279 | 674.2 | | | 14.1 | | 467 | 467.41 |
| 95 | 25.45 | 6516.5 | | | | | 465.3 | 464.61 |
| 96 | 1.692 | 4224 | | | 35.3 | | 466.1 | 465.60 |
| 97 | 1.7785 | 1806 | | | 13.3 | | 455.1 | 454.57 |
| 98 | 24.54 | 7355 | | | | | 516.2 | 515.66 |
| 99 | 19.335 | 3488 | | | 12.5 | | 471.0 | 470.64 |
| 100 | 0.27385 | 5.854 | | | 0.452 | | 405.0 | 404.51 |
| 101 | 9.14235 | 532.3 | | | 19.3 | | 466 | 465.60 |
| 102 | 68.03 | 2860 | | | | | 407.1 | 406.50 | rDOR Ki: Rat brain delta opioid receptor binding
rMOR Ki: Rat brain mu opioid receptor binding
hDOR gtp: human delta opioid receptor GTPγS functional assay
hMOR gtp: human mu opioid receptor GTPγS functional assay
DOR gtp: delta opioid receptor GTPγS functional assay
MAIT: Mouse Abdominal Irritant Test Compounds 1 and 5, at 10 uM, did not significantly stimulate GTP binding. However, at 10 uM they inhibited GTP binding induced with 1 uM DPDPE by 61% and 19%, respectively. The results indicate that these two compounds may be delta opioid receptor antagonists.

The invention claimed is:

1. A compound of Formula (I):

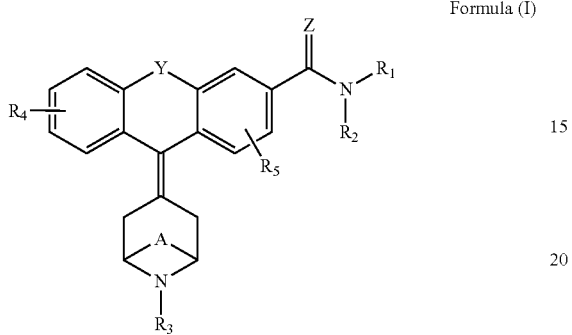

Formula (I)

wherein:

$R_1$ and $R_2$ are substituents independently selected from the group consisting of hydrogen and $C_{1-8}$alkanyl;

$R_3$ is selected from the group consisting of hydrogen, $C_{1-8}$alkanyl, $halo_{1-3}(C_{1-8})$alkanyl, $C_{2-8}$alkenyl, $C_{2-8}$alkynyl, $C_{3-8}$cycloalkanyl, cycloalkanyl($C_{1-8}$)alkanyl, $C_{1-8}$alkanyloxy($C_{1-8}$)alkanyl, $C_{1-8}$alkanylthio($C_{1-8}$)alkanyl, hydroxy$C_{1-8}$alkanyl, $C_{1-8}$alkanyloxycarbonyl, $halo_{1-3}(C_{1-8})$alkanylcarbonyl, formyl, thioformyl, carbamimidoyl, phenylimino($C_{1-8}$)alkanyl, phenyl($C_{1-8}$)alkanyl, phenyl($C_{1-8}$)alkenyl, phenyl($C_{1-8}$)alkynyl, naphthyl($C_{1-8}$)alkanyl and heteroaryl($C_{1-8}$)alkanyl; wherein phenyl, naphthyl and heteroaryl are optionally substituted with one to three substituents independently selected from the group consisting of $C_{1-6}$alkanyl, $C_{2-6}$alkenyl, $C_{1-6}$alkanyloxy, amino, $C_{1-6}$alkanylamino, di($C_{1-6}$alkanyl)amino, $C_{1-6}$alkanylcarbonyl, $C_{1-6}$alkanylcarbonyloxy, $C_{1-6}$alkanylcarbonylamino, $C_{1-6}$alkanylthio, $C_{1-6}$alkanylsulfonyl, halogen, hydroxy, cyano, fluoroalkanyl, thioureido, and fluoroalkanyloxy; or optionally, when phenyl and heteroaryl are optionally substituted with two substituents attached to adjacent carbon atoms, the two substituents together form a single fused moiety; wherein the fused moiety is selected from the group consisting of —(CH$_2$)$_{3-5}$— and —O(CH$_2$)$_{1-3}$O—;

$R_4$ is one to three substituents independently selected from the group consisting of hydrogen, $C_{1-6}$alkanyl, $C_{2-6}$alkenyl, $C_{1-6}$alkanyloxy, amino, $C_{1-6}$alkanylamino, di($C_{1-6}$alkanyl)amino, $C_{1-6}$alkanylcarbonyl, $C_{1-6}$alkanylcarbonyloxy, $C_{1-6}$alkanyloxycarbonyl, $C_{1-6}$alkanylaminocarbonyl, di($C_{1-6}$alkanyl)aminocarbonyl, $C_{1-6}$alkanylcarbonylamino, $C_{1-6}$alkanylthio, $C_{1-6}$alkanylsulfonyl, halogen, hydroxy, cyano, hydroxycarbonyl, $C_{6-10}$aryl, chromanyl, chromenyl, furanyl, imidazolyl, indazolyl, indolyl, indolinyl, isoindolinyl, isoquinolinyl, isothiazolyl, isoxazolyl, naphthyridinyl, oxazolyl, pyrazinyl, pyrazolyl, pyridazinyl, pyridinyl, pyrimidinyl, pyrrolyl, quinazolinyl, quinolinyl, quinolizinyl, quinoxalinyl, tetrazolyl, thiazolyl, thiophenyl and fluoroalkanyl and fluoroalkanyloxy; or optionally, when $R_4$ is two substituents attached to adjacent carbon atoms, the two substituents together form a single fused moiety; wherein the fused moiety is selected from the group consisting of —(CH$_2$)$_{3-5}$— and —O(CH$_2$)$_{1-3}$O—;

$R_5$ is one to two substituents independently selected from the group consisting of hydrogen, $C_{1-6}$alkanyl, $C_{2-6}$alkenyl, $C_{1-6}$alkanyloxy, amino, $C_{1-6}$alkanylamino, di($C_{1-6}$alkanyl)amino, $C_{1-6}$alkanylcarbonyl, $C_{1-6}$alkanylcarbonyloxy, $C_{1-6}$alkanyloxycarbonyl, $C_{1-6}$alkanylaminocarbonyl, $C_{1-6}$alkanylcarbonylamino, $C_{1-6}$alkanylthio, $C_{1-6}$alkanylsulfonyl, halogen, hydroxy, cyano, fluoroalkanyl and fluoroalkanyloxy;

A is —(CH$_2$)$_m$—, wherein m is 0;

Y is S;

Z is O; and enantiomers, diastereomers, tautomers, and pharmaceutically acceptable salts thereof.

2. The compound according to claim 1 wherein $R_1$ and $R_2$ are substituents independently selected from the group consisting of hydrogen and $C_{1-4}$alkanyl.

3. The compound according to claim 1 wherein $R_1$ and $R_2$ are substituents independently selected from the group consisting of hydrogen, methyl, ethyl and propyl.

4. The compound according to claim 1 wherein $R_1$ and $R_2$ are substituents independently selected from the group consisting of hydrogen and ethyl.

5. The compound according to claim 1 wherein $R_3$ is selected from the group consisting of hydrogen, $C_{1-8}$alkanyl, $C_{2-8}$alkenyl, $C_{2-8}$alkynyl, $C_{1-8}$alkanyloxy($C_{1-8}$)alkanyl, $C_{1-8}$alkanylthio($C_{1-8}$)alkanyl, hydroxy$C_{1-8}$alkanyl, thioformyl, phenylimino($C_{1-8}$)alkanyl, phenyl($C_{1-8}$)alkanyl, and heteroaryl($C_{1-8}$)alkanyl; wherein phenyl and heteroaryl are optionally substituted with one to three substituents independently selected from the group consisting of $C_{1-6}$alkanyloxy and hydroxy; or optionally, when phenyl and heteroaryl are optionally substituted with two substituents attached to adjacent carbon atoms, the two substituents together form a single fused moiety; wherein the moiety is selected from O(CH$_2$)$_{1-3}$O.

6. The compound according to claim 1 wherein $R_3$ is selected from the group consisting of hydrogen, methyl, allyl, 2-methyl-allyl, propynyl, hydroxyethyl, thioformyl, phenyliminomethyl, phenethyl, and heteroaryl($C_{1-8}$)alkanyl; wherein the phenyl in any phenyl-containing substituent is optionally substituted with one hydroxyl group.

7. The compound according to claim 1 wherein $R_3$ is hydrogen or methyl, allyl, heteroarylmethyl.

8. The compound according to claim 1 wherein $R_4$ is one to three substituents independently selected from the group consisting of hydrogen, $C_{1-6}$alkanyl, $C_{1-6}$alkanyloxy, $C_{1-6}$alkanylaminocarbonyl, $C_{1-6}$alkanylcarbonylamino, halogen, 4ydroxyl, $C_{6-10}$aryl, chromanyl, chromenyl, furanyl, imidazolyl, indazolyl, indolyl, indolinyl, isoindolinyl, isoquinolinyl, isothiazolyl, isoxazolyl, naphthyridinyl, oxazolyl, pyrazinyl, pyrazolyl, pyridazinyl, pyridinyl, pyrimidinyl, pyrrolyl, quinazolinyl, quinolinyl, quinolizinyl, quinoxalinyl, tetrazolyl, thiazolyl, and thiophenyl.

9. The compound according to claim 1 wherein $R_4$ is one to two substituents independently selected from the group consisting of hydrogen, $C_{1-4}$alkanyl, $C_{1-4}$alkanyloxy, halogen, phenyl, furanyl, imidazolyl, indazolyl, indolyl, indolinyl, isoindolinyl, isoquinolinyl, isothiazolyl, isoxazolyl, oxazolyl, pyrazinyl, pyrazolyl, pyridazinyl, pyridinyl, pyrimidinyl, pyrrolyl, quinolinyl, tetrazolyl, thiazolyl, thiophenyl, and hydroxyl.

10. The compound according to claim 1 wherein $R_4$ is one to two substituents independently selected from the group consisting of hydrogen, methyl, methoxy, bromo, fluoro, 5- or 6-phenyl, 5- or 6-pyridinyl, 5- or 6-furanyl, and hydroxyl.

11. The compound according to claim 1 wherein $R_5$ is one to two substituents independently selected from the group consisting of hydrogen and halogen.

12. The compound according to claim 1 wherein $R_5$ is hydrogen.

13. A compound of Formula (I):

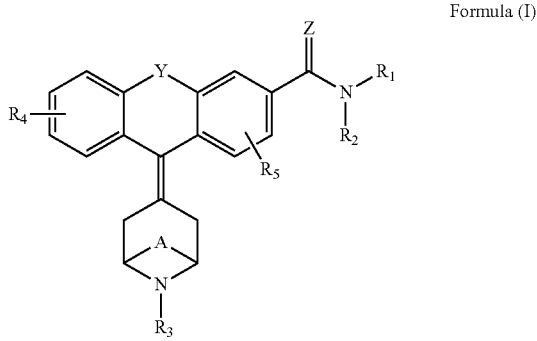

Formula (I)

wherein $R_1$ is $C_{1-3}$alkanyl;
$R_2$ is $C_{1-3}$alkanyl or hydrogen;
$R_3$ is selected from the group consisting of hydrogen, $C_{1-8}$alkanyl, $C_{2-8}$alkenyl, $C_{2-8}$alkynyl, $C_{1-8}$alkanyloxy $(C_{1-8})$alkanyl, $C_{1-8}$alkanylthio$(C_{1-8})$alkanyl, hydroxy$C_{1-8}$alkanyl, thioformyl, phenylimino$(C_{1-8})$alkanyl, phenyl$(C_{1-8})$alkanyl, and heteroaryl$(C_{1-8})$alkanyl; wherein phenyl and heteroaryl are optionally substituted with one to three substituents independently selected from the group consisting of $C_{1-6}$alkanyloxy and 5ydroxyl; or optionally, when phenyl and heteroaryl are optionally substituted with two substituents attached to adjacent carbon atoms, the two substituents together form a single fused moiety; wherein the moiety is selected from —O(CH$_2$)$_{1-3}$O—;
$R_4$ is one to three substituents independently selected from the group consisting of hydrogen, $C_{1-6}$alkanyl, $C_{1-6}$alkanyloxy, $C_{1-6}$alkanylaminocarbonyl, $C_{1-6}$alkanylcarbonylamino, halogen, 5ydroxyl, $C_{6-10}$aryl, chromanyl, chromenyl, furanyl, imidazolyl, indazolyl, indolyl, indolinyl, isoindolinyl, isoquinolinyl, isothiazolyl, isoxazolyl, naphthyridinyl, oxazolyl, pyrazinyl, pyrazolyl, pyridazinyl, pyridinyl, pyrimidinyl, pyrrolyl, quinazolinyl, quinolinyl, quinolizinyl, quinoxalinyl, tetrazolyl, thiazolyl, and thiophenyl;
$R_5$ is one to two substituents independently selected from the group consisting of hydrogen and halogen;
A is absent;
Y is S;
Z is O; and
enantiomers, diastereomers, tautomers, and pharmaceutically acceptable salts thereof.

14. The compound according to claim 13 wherein $R_1$ is ethyl; $R_2$ is ethyl or hydrogen; and $R_3$ is benzo[1,3]dioxol-5-ylmethyl, carbamimidoyl, 1-H-imidazol-4-yl methyl, phenyliminomethyl, 1-prop-2-ynyl, thioformyl, 2-hydroxyphenyl-methyl, hydroxyethyl, methoxyethyl, 2-methyl-allyl, 2-methyl-but-2-enyl, allyl, furan-3-yl methyl, H, Me, methylthioethyl, phenethyl, 6yridine-2-ylmethyl, or thiophen-2-ylmethyl.

15. The compound according to claim 13 wherein $R_1$ is ethyl; $R_2$ is ethyl; and $R_3$ is benzo[1,3]dioxol-5-ylmethyl, carbamimidoyl, 1-H-imidazol-4-ylmethyl, phenyliminomethyl, 1-prop-2-ynyl, thioformyl, 2-hydroxyphenyl-methyl, hydroxyethyl, methoxyethyl, allyl, furan-3-ylmethyl, H, Me, methylthioethyl, or phenethyl.

16. The compound according to claim 13 wherein $R_1$ is ethyl; $R_2$ is ethyl; and $R_3$ is H, benzo[1,3]dioxol-5-ylmethyl, 1-H-imidazol-4-ylmethyl, furan-3-ylmethyl, 6yridine-2-ylmethyl, or phenyliminomethyl.

17. The compound according to claim 13 wherein $R_3$ is hydrogen, methyl, allyl, or heteroarylmethyl.

18. The compound according to claim 13 wherein $R_3$ is hydrogen, methyl, allyl, or heteroarylmethyl; and $R_4$ is one to two substituents independently selected from the group consisting of hydrogen, methyl, methoxy, bromo, fluoro, 5- or 6-phenyl, 5- or 6-pyridinyl, 5- or 6-furanyl, and hydroxy; and $R_5$ is hydrogen.

19. A pharmaceutical composition comprising a compound or salt according to claim 1 admixed with a pharmaceutically acceptable carrier, excipient or diluent.

20. A veterinary composition comprising a compound, salt or solvate according to claim 1 admixed with a veterinarily acceptable carrier, excipient or diluent.

21. A pharmaceutical composition comprising a compound, salt or solvate according to claim 13 admixed with a pharmaceutically acceptable carrier, excipient or diluent.

22. A veterinary composition comprising a compound or salt according to claim 13 admixed with a veterinarily acceptable carrier, excipient or diluent.

* * * * *